United States Patent
Nakatsuru et al.

(10) Patent No.: US 9,334,376 B2
(45) Date of Patent: May 10, 2016

(54) WATER-ABSORBABLE POLYACRYLIC ACID RESIN POWDER, AND PROCESS FOR PRODUCTION THEREOF

(75) Inventors: Reiko Nakatsuru, Himeji (JP); Shigeru Sakamoto, Himeji (JP); Kazushi Torii, Himeji (JP); Toshihiro Takaai, Himeji (JP)

(73) Assignee: NIPPON SHOKUBAI CO., LTD, Osaka-shi, Osaka (JP)

( * ) Notice: Subject to any disclaimer, the term of this patent is extended or adjusted under 35 U.S.C. 154(b) by 803 days.

(21) Appl. No.: 13/518,438

(22) PCT Filed: Dec. 23, 2010

(86) PCT No.: PCT/JP2010/073254
§ 371 (c)(1),
(2), (4) Date: Jun. 22, 2012

(87) PCT Pub. No.: WO2011/078298
PCT Pub. Date: Jun. 30, 2011

(65) Prior Publication Data
US 2012/0258851 A1    Oct. 11, 2012

(30) Foreign Application Priority Data

Dec. 24, 2009  (JP) .................................. 2009292318
Apr. 7, 2010   (JP) .................................. 2010088993
Jun. 30, 2010  (JP) .................................. 2010149907
Aug. 10, 2010  (JP) .................................. 2010179515

(51) Int. Cl.
*B01J 20/26* (2006.01)
*C08J 3/12* (2006.01)
(Continued)

(52) U.S. Cl.
CPC .. *C08J 3/12* (2013.01); *A61L 15/48* (2013.01); *A61L 15/60* (2013.01); *C08F 20/06* (2013.01); *C08F 220/06* (2013.01); *C08J 2333/08* (2013.01); *C08J 2333/10* (2013.01)

(58) Field of Classification Search
None
See application file for complete search history.

(56) References Cited

U.S. PATENT DOCUMENTS 4,656,232 A    4/1987  Nakaki et al.
4,703,067 A   10/1987  Mikita et al.
(Continued)

FOREIGN PATENT DOCUMENTS

EP    0450922    10/1991
EP    0595803    10/1991
(Continued)

OTHER PUBLICATIONS

EP Search Report mailed Apr. 24, 2013, EP Patent Application No. 10839528.6.
(Continued)

*Primary Examiner* — Melvin C Mayes
*Assistant Examiner* — Michael Forrest
(74) *Attorney, Agent, or Firm* — Casimir Jones, SC

(57) ABSTRACT

A process according to the present invention for production of water-absorbable polyacrylic acid resin powder, including: (a) polymerizing an acrylic acid-based monomer aqueous solution containing bubbles, and (b) drying a hydrogel crosslinked polymer thus obtained in the step of polymerizing, further includes (c) lowering solubility of dissolved gas in a monomer aqueous solution in the presence of a surfactant and/or a dispersing agent, so as to generate the bubbles in the acrylic acid-based monomer aqueous solution. With this arrangement, it is possible to provide white water-absorbable resin with better water absorbing rate, keeping or without significantly losing the other properties (permeability potential, bulk specific gravity, surface tension, absorbency against pressure, impact resistance, etc.)

12 Claims, 14 Drawing Sheets

WATER-ABSORBABLE RESIN POWDER (2)

COMPARATIVE WATER-ABSORBABLE RESIN POWDER (2)

(51) Int. Cl.
*C08F 220/06* (2006.01)
*A61L 15/48* (2006.01)
*A61L 15/60* (2006.01)
*C08F 20/06* (2006.01)

(56) References Cited

U.S. PATENT DOCUMENTS

| | | |
|---|---|---|
| 4,857,610 A | 8/1989 | Chmelir et al. |
| 4,893,999 A | 1/1990 | Chmelir et al. |
| 4,954,562 A | 9/1990 | Anderson |
| 4,985,518 A | 1/1991 | Alexander et al. |
| 5,002,986 A | 3/1991 | Fujiura et al. |
| 5,118,719 A | 6/1992 | Lind |
| 5,124,188 A | 6/1992 | Roe et al. |
| 5,145,906 A | 9/1992 | Chambers et al. |
| 5,154,713 A | 10/1992 | Lind |
| 5,314,420 A | 5/1994 | Smith et al. |
| 5,338,766 A | 8/1994 | Phan et al. |
| 5,380,808 A | 1/1995 | Sumiya et al. |
| 5,399,591 A | 3/1995 | Smith et al. |
| 5,451,452 A | 9/1995 | Phan et al. |
| 5,451,613 A | 9/1995 | Smith et al. |
| 5,462,972 A | 10/1995 | Smith et al. |
| 5,562,646 A | 10/1996 | Goldman et al. |
| 5,624,967 A | 4/1997 | Hitomi et al. |
| 5,712,316 A | 1/1998 | Dahmen et al. |
| 5,837,789 A | 11/1998 | Stockhausen et al. |
| 5,856,370 A | 1/1999 | Chmelir |
| 5,985,944 A | 11/1999 | Ishizaki et al. |
| 6,071,976 A | 6/2000 | Dairoku et al. |
| 6,100,305 A | 8/2000 | Miyake |
| 6,107,358 A * | 8/2000 | Harada et al. ............... 521/133 |
| 6,136,873 A | 10/2000 | Hahnle et al. |
| 6,174,929 B1 | 1/2001 | Hahnle et al. |
| 6,359,049 B1 | 3/2002 | Carrico et al. |
| 6,414,214 B1 | 7/2002 | Engelhardt et al. |
| 6,562,879 B1 | 5/2003 | Hatsuda et al. |
| 6,710,141 B1 | 3/2004 | Heide et al. |
| 6,750,262 B1 | 6/2004 | Hahnle et al. |
| 6,939,914 B2 | 9/2005 | Qin et al. |
| 7,091,253 B2 | 8/2006 | Dairoku et al. |
| 7,169,843 B2 | 1/2007 | Smith et al. |
| 7,173,086 B2 | 2/2007 | Smith et al. |
| 7,265,190 B2 | 9/2007 | Dairoku et al. |
| 7,473,739 B2 | 1/2009 | Dairoku et al. |
| 7,582,705 B2 | 9/2009 | Dairoku et al. |
| 2005/0176834 A1 | 8/2005 | Hintz et al. |
| 2005/0209352 A1 | 9/2005 | Dairoku et al. |
| 2005/0256469 A1 | 11/2005 | Qin et al. |
| 2006/0036043 A1 | 2/2006 | Nestler |
| 2007/0015860 A1 | 1/2007 | Frank |
| 2007/0088093 A1 | 4/2007 | Joy et al. |
| 2007/0197749 A1 | 8/2007 | Matsuda et al. |
| 2007/0225422 A1* | 9/2007 | Sakamoto et al. ........... 524/458 |
| 2008/0227933 A1 | 9/2008 | Funk |
| 2008/0269372 A1* | 10/2008 | Dairoku et al. ............. 523/149 |
| 2009/0234314 A1* | 9/2009 | Nakamura et al. ........... 604/367 |
| 2010/0234531 A1 | 9/2010 | Frank |
| 2010/0240808 A1 | 9/2010 | Wada et al. |
| 2010/0268181 A1 | 10/2010 | Ziemer et al. |
| 2011/0015285 A1 | 1/2011 | Aulenta et al. |
| 2011/0313113 A1 | 12/2011 | Sakamoto et al. |

FOREIGN PATENT DOCUMENTS

| | | |
|---|---|---|
| EP | 0496067 | 7/1992 |
| EP | 0827753 | 3/1998 |
| EP | 0827753 A2 | 3/1998 |
| EP | 0876888 | 11/1998 |
| EP | 1521601 | 4/2005 |
| EP | 1837348 A1 | 9/2007 |
| EP | 2116571 | 11/2009 |
| EP | 1957188 | 2/2010 |
| JP | 57-034101 | 2/1982 |
| JP | 62-156102 | 7/1987 |
| JP | 1-126310 | 5/1989 |
| JP | 1-318021 | 12/1989 |
| JP | 3-115313 | 5/1991 |
| JP | 3-174414 | 7/1991 |
| JP | 4-175319 | 6/1992 |
| JP | 4-236203 | 8/1992 |
| JP | 5-237378 | 9/1993 |
| JP | 9-124879 | 5/1997 |
| JP | 10-57805 | 3/1998 |
| JP | 10-114801 | 5/1998 |
| JP | 10-119042 | 5/1998 |
| JP | 10-168129 | 6/1998 |
| JP | 10-251310 | 9/1998 |
| JP | 11-035691 | 2/1999 |
| JP | 11-147902 | 6/1999 |
| JP | 2000-506911 | 6/2000 |
| JP | 2005-162834 | 6/2005 |
| JP | 2007/284675 | 11/2007 |
| JP | 2008-024943 | 2/2008 |
| JP | 2008-237430 | 10/2008 |
| WO | 91/15368 | 10/1991 |
| WO | 92/18171 | 10/1992 |
| WO | 94/22502 | 10/1994 |
| WO | 95/02002 | 1/1995 |
| WO | 97/17397 | 5/1997 |
| WO | 97/19116 | 5/1997 |
| WO | 00/52087 | 9/2000 |
| WO | 2004/052949 | 6/2004 |
| WO | 2005/007713 A1 | 1/2005 |
| WO | 2005/012406 | 2/2005 |
| WO | 2005/063313 | 7/2005 |
| WO | 2005/075070 | 8/2005 |
| WO | 2006/008905 | 1/2006 |
| WO | 2006109844 | 10/2006 |
| WO | 2007/025921 | 3/2007 |
| WO | 2009/048145 | 4/2009 |
| WO | 2009/062902 | 5/2009 |
| WO | 2009/092714 | 7/2009 |

OTHER PUBLICATIONS

U.S. Office Action mailed Jul. 2, 2013, U.S. Appl. No. 13/201,701.
Decision to Grant JP Patent Application No. 2011-547617 mailed Oct. 28, 2014, 5 pages (English translation attached).
Buchholz F., et al., "Modern Superabsorbent Polymer Technology" (WILEY-VCH, 1998, especially p. 39-44, p. 197-199).
International Search Report for PCT/JP2010/001004 dated Jun. 1, 2010.
International Search Report for PCT/JP2010/073254 dated Mar. 29, 2011.
Decision to Grant JP Patent Application No. 2011-500511 mailed Jul. 22, 2014.
EP Search Report mailed Mar. 22, 2013, EP Patent Application No. 10743557.0.
Final Office Action mailed Nov. 4, 2013, U.S. Appl. No. 13/201,701.
Notification of Information Offer Form against the Japanese patent application No. 2014-166146 dated Jun. 16, 2015 of related U.S. Appl. No. 13/201,701.
Office Action for co-pending U.S. Appl. No. 14/301,773, mailed Jun. 19, 2015.
Notification of Information Offer Form of Corresponding Japanese Patent Application No. 2014-044309, mailed May 7, 2015, English translation provided.

* cited by examiner

WATER-ABSORBABLE POLYACRYLIC ACID RESIN POWDER, AND PROCESS FOR PRODUCTION THEREOF

CROSS-REFERENCE TO RELATED APPLICATIONS

The present application is a Section 371 U.S. national stage entry of pending International Patent Application No. PCT/JP2010/073254, International Filing Date Dec. 23, 2010, which published on Jun. 30, 2011 as Publication No. WO 2011/078298, which claims the benefit of Japanese Patent Application No. 2009-292318, filed Dec. 24, 2009, Japanese Patent Application No. 2010-088993, filed Apr. 7, 2010, Japanese Patent Application No. 2010-149907, filed Jun. 30, 2010, and Japanese Patent Application No. 2010-179515, filed Aug. 10, 2010, the contents of which are incorporated by reference in their entireties.

TECHNICAL FIELD

The present invention relates to water-absorbable polyacrylic acid resin powder and a process for production thereof. More specifically, the present invention relates to water-absorbable polyacrylic acid resin powder having excellent water absorbing ability (especially having a high water absorbing rate) and a process for production thereof, which water-absorbable polyacrylic acid resin powder is water-absorbable resin powder for use in sanitary goods such as disposable diaper, sanitary napkins etc.

BACKGROUND ART

Water-absorbable resin (SAP/Super Absorbent Polymer) is a polymer gelling agent which is swellable with water but insoluble with water. The Water-absorbable resin is widely used, mainly disposably, for absorbing products such as disposable diapers, sanitary napkins, etc., and further for agriculture/horticulture water retaining agent, an industrial waterproofing agent, and the like. For such Water-absorbable resin, many monomers and hydrophilic polymers have been proposed as raw materials. Especially, water-absorbable polyacrylic acid resin in which acrylic acid and/or its salt is used as its monomer is most popular in industries because of its high water absorbing ability (Non-Patent Literature 1).

The water-absorbable resin is produced via a polymerizing step, a drying step, and if necessary, a non-dried matter removing step, a grinding step, a classifying step, a surface cross-linking step, and/or the like (Patent Literatures 1 to 5).

Meanwhile, the water-absorbable resin is required to have many functions in order to cope with functional sophistication of disposable diapers which are one major application of the water absorbable resin. More specifically, the water-absorbable resin is required to satisfy many properties such as, not only a high water absorbing coefficient, but also gel strength, water soluble content, water absorbing rate, an absorbency against pressure, permeability potential, particle diameter distribution, an anti-urine property, an anti microbial property, an impact resistance (anti-damage property), a fluidity, an deodorant property, an anti-coloring (degree of whiteness), low dustiness, etc. Therefore, many crosslinking techniques, additives, modifications in steps in the production, etc. have been proposed in Patent Literatures above or below.

Among these properties, the permeability potential is considered as a more important factor in association with a recent increase (for example, 50 wt % or more) in an amount of the water-absorbable resin in disposable diapers. Furthermore, methods and techniques for improving permeability potential against pressure and permeability potential without pressure, such as SFC (Saline Flow Conductivity, see Patent Literature 6) or GBP (Gel Bed Permeability, see Patent Literatures 7 to 9), etc., have been proposed.

Moreover, in addition to the permeability potential, the water absorbing rate is also a basic property for the water-absorbable resin. As one method for improving the water absorbing rate, a technique to increase a specific surface area in order to attain a greater water absorbing rate is known. More specifically, a technique for controlling to attain fine particle diameters (Patent Literature 10), techniques for granulating fine particles with a large surface area (Patent Literatures 11 to 13), a technique for freeze-drying a hydrogel to cause the hydrogel to be porous (Patent Literature 14), techniques for performing granulation and surface crosslinking of particles simultaneously (Patent Literatures 15 to 17), techniques for foaming polymerization (Patent Literatures 18 to 35), and a technique for post-polymerization foaming and crosslinking (Patent Literature 36), etc. have been proposed.

More specifically, as to the foaming polymerization, the following techniques have been known regarding a foaming agent for treating a monomer(s): techniques for using a carbonate (Patent Literatures 18 to 25), techniques for using an organic solvent (Patent Literatures 26 and 27), a technique for using an inert gas (Patent Literatures 28 to 30), techniques for using an azo compound (Patent Literatures 31 and 32), techniques for using insoluble inorganic powder or water-insoluble particles (Patent Literatures 33 and 34). Furthermore, a technique for polymerizing, without stirring, a slurry in which sodium acrylate fine precipitates are contained by 45 to 60 wt % with micro bubbles of inert gas (Patent Literature 35). Further, a technique for post-polymerization foaming and crosslinking (Patent Literature 36), etc. has been proposed.

These techniques described in Patent Literatures 10 to 36 etc. are successful in improving the water absorbing rate to some extent by increasing the surface area, etc. However, the improvement in the water absorbing rate is not so sufficient, and a special device or a costly raw material (a large amount of surfactant or foaming agent) is necessary. Further, these techniques described in Patent Literatures 10 to 36 etc. have a problem, for example, that they deteriorate the permeability potential (Patent Literatures 6 to 9), impact resistance (Patent Literature 37), bulk specific gravity (Patent Literatures 38 and 39), etc.

That is, the water absorbing rate and the specific surface area are, in general, in positive interaction relationship, but the permeability potential and the specific surface area are in negative interaction relationship. This makes it very difficult to improve both of the water absorbing rate and the permeability potential, which are largely dependent from the surface area.

Further, dispersion of the bubble by use of a large amount of surfactant as in Patent Literatures 28 and 29 leads to not only a cost increase associated with the surfactant but also to a lower surface tension of the water-absorbable resin, thereby causing an increase in amount of rewetting.

Further, the water-absorbable resin for absorbing products such as disposable diapers and sanitary napkins are used in combination with white pulps in many cases. Thus, for the sake of giving a sensation of cleanness, the water-absorbable resin is required to be white in color. Therefore, many modifying techniques in coloring have been proposed for the degree of whiteness for the water-absorbable resin (Patent Literature 40 to 42). However, at this moment, these techniques are again insufficient in terms of an anti-coloring agent cost, safety, complicate process, and further degree of their effect.

CITATION LIST

Patent Literatures

Patent Literature 1
EP Patent No. 1957188 B, Specification
Patent Literature 2
U.S. Pat. No. 7,265,190 B, Specification
Patent Literature 3
Japanese Patent Application Publication, Tokukai, No. 2005-162834 A
Patent Literature 4
U.S. Pat. No. 6,710,141 B, Specification
Patent Literature 5
U.S. Pat. No. 7,091,253 B, Specification
Patent Literature 6
U.S. Pat. No. 5,562,646 B, Specification
Patent Literature 7
US Patent Application Publication No. 2005/0256469 A, Specification
Patent Literature 8
U.S. Pat. No. 7,169,843 B, Specification
Patent Literature 9
U.S. Pat. No. 7,173,086 B, Specification
Patent Literature 10
PCT International Publication No. 92/18171 A, Pamphlet
Patent Literature 11
U.S. Pat. No. 5,624,967 B, Specification
Patent Literature 12
PCT International Publication No. 2005/012406 A, Pamphlet
Patent Literature 13
U.S. Pat. No. 5,002,986 B, Specification
Patent Literature 14
U.S. Pat. No. 6,939,914 B, Specification
Patent Literature 15
U.S. Pat. No. 5,124,188 B, Specification
Patent Literature 16
EP Patent No. 0595803 B, Specification
Patent Literature 17
EP Patent No. 0450922 B, Specification
Patent Literature 18
PCT International Publication No. 91/15368 A, Pamphlet
Patent Literature 19
U.S. Pat. No. 5,154,713 B, Specification
Patent Literature 20
U.S. Pat. No. 5,314,420 B, Specification
Patent Literature 21
U.S. Pat. No. 5,399,591 B, Specification
Patent Literature 22
U.S. Pat. No. 5,451,613 B, Specification
Patent Literature 23
U.S. Pat. No. 5,462,972 B, Specification
Patent Literature 24
PCT International Publication No. 95/02002 A, Pamphlet
Patent Literature 25
PCT International Publication No. 2005/063313 A, Pamphlet
Patent Literature 26
PCT International Publication No. 94/022502 A, Pamphlet
Patent Literature 27
U.S. Pat. No. 4,703,067 B, Specification
Patent Literature 28
PCT International Publication No. 97/017397 A, Pamphlet
Patent Literature 29
PCT International Publication No. 00/052087 A, Pamphlet
Patent Literature 30
U.S. Pat. No. 6,107,358 B, Specification
Patent Literature 31
U.S. Pat. No. 5,856,370 B, Specification
Patent Literature 32
U.S. Pat. No. 5,985,944 B, Specification
Patent Literature 33
PCT International Publication No. 2009/062902 A, Pamphlet
Patent Literature 34
US Patent Application Publication, No. 2007/0225422 A, Specification
Patent Literature 35
Japanese Patent Application Publication, Tokukaihei, No. 1-318021 A
Patent Literature 36
EP Patent No. 1521601 B, Specification
Patent Literature 37
U.S. Pat. No. 6,414,214 B, Specification
Patent Literature 38
U.S. Pat. No. 6,562,879 B, Specification
Patent Literature 39
U.S. Pat. No. 7,582,705 B, Specification
Patent Literature 40
U.S. Pat. No. 6,359,049 B, Specification
Patent Literature 41
PCT International Publication No. 2006/008905 A, Pamphlet
Patent Literature 42
PCT International Publication No. 2004/052949 A, Pamphlet Non-Patent Literatures Non-Patent Literature 1
Modern Superabsorbent Polymer Technology (1998), (especially, p. 39 to 44, and p. 197 to 199, etc.)

SUMMARY OF INVENTION

Technical Problem

One object to be attained by the present invention is to provide white water-absorbable resin powder in which a higher water absorbing rate (for example, FSR) is attained with no sacrificing or almost no sacrificing other properties of the water-absorbable resin (permeability potential, bulk specific gravity, surface tension, water absorbency against pressure, impact resistance, etc.), and further without requiring a costly expensive raw material or device, especially to provide white water-absorbable resin powder in which both of a high permeability potential (for example, SFC) and a high water absorbing rate (for example, FSR) are attained.

Solution to Problem

In order to attain the object, the inventor of the present invention noticed that it is important how to disperse the bubbles in the monomer(s) to be polymerized. The inventor found that the object can be attained by using a particular method, thereby making it possible to obtain water-absorbable resin powder having no deterioration in bulk specific gravity and surface tension, and further preferably being excellent in degree of whiteness, permeability potential, and impact resistance (or anti-damaging property). Thereby, the present invention was accomplished. Moreover, for better water absorbing rate, the aforementioned patent literatures have proposed to increase the surface area, foaming polymerization, and obtaining porous polymer. The present invention firstly points out the importance of the closed cells (or internal cells), which has not been noticed previously. The inventor found that the object can be attained by controlling the closed-cell rate of the water-absorbable resin within a particular range. Thereby, the present invention was accomplished.

In order to attain the object, a process (first process) according to the present invention for production of water-absorbable polyacrylic acid resin powder, comprising (a) polymerizing an acrylic acid-based monomer aqueous solution containing bubbles, and (b) drying a hydrogel crosslinked polymer thus obtained in the step of polymerizing, the process further comprises: (c) lowering solubility of dissolved gas in a monomer aqueous solution in the presence of a surfactant and/or a dispersing agent, so as to generate the bubbles in the acrylic acid-based monomer aqueous solution.

Moreover, in order to attain the object, a process (second process) according to the present invention for production of water-absorbable polyacrylic acid resin powder, comprising: (a) polymerizing an acrylic acid-based monomer aqueous solution containing bubbles, and (b) drying a hydrogel crosslinked polymer thus obtained in the step of polymerizing, further comprises (d) heating the acrylic acid-based monomer aqueous solution in the presence of a surfactant and/or a dispersing agent.

Moreover, in order to attain the object, a process (third process) according to the present invention for production of water-absorbable polyacrylic acid resin powder, comprising (a) polymerizing an acrylic acid-based monomer aqueous solution containing bubbles, and (b) drying a hydrogel crosslinked polymer thus obtained in the step of polymerizing, further comprises: (e) mixing a water soluble organic material into the acrylic acid-based monomer aqueous solution in the presence of a surfactant and/or a dispersing agent.

In order to attain the object (especially, to attain both the permeability potential and water absorbing rate, and to attain the anti-damaging property), water-absorbable resin (first water-absorbable resin) according to the present invention is water-absorbable polyacrylic acid resin powder in which particles having a particle diameter of 850 μm to 150 μm accounts for 95 wt % or more, and having an internal cell rate of 2.8% to 6.6%, the internal cell rate being defined by the following equation:

$$\text{(Closed-cell rate [\%])} = \{(\text{Real Density [g/cm}^3\text{])} - (\text{Apparent Density [g/cm}^3\text{])}\}/(\text{Real Density [g/cm}^3\text{])} \times 100$$

In order to attain the object (especially, to attain the anti-damaging property), water-absorbable resin (second water-absorbable resin) according to the present invention is water-absorbable polyacrylic acid resin powder comprising a surfactant and/or a dispersing agent inside thereof, wherein: the water-absorbable resin powder has a surface tension of 60 [mN/m] or greater, and a particle surface being coated with a/the surfactant.

Advantageous Effects of Invention

According to a process according to the present invention for the production of the water-absorbable resin powder, it is possible to produce water-absorbable resin powder having a high water absorbing rate, without using a large amount of surfactant, but with good productivity and efficiency. Moreover, for example the water-absorbable resin powder according to the present invention obtained by a process according to the present invention (one example of process according to the present invention) is novel water-absorbable resin powder having both the water absorbing rate and permeability potential, and further being excellent in impact resistance.

DESCRIPTION OF EMBODIMENTS

Figure 1:
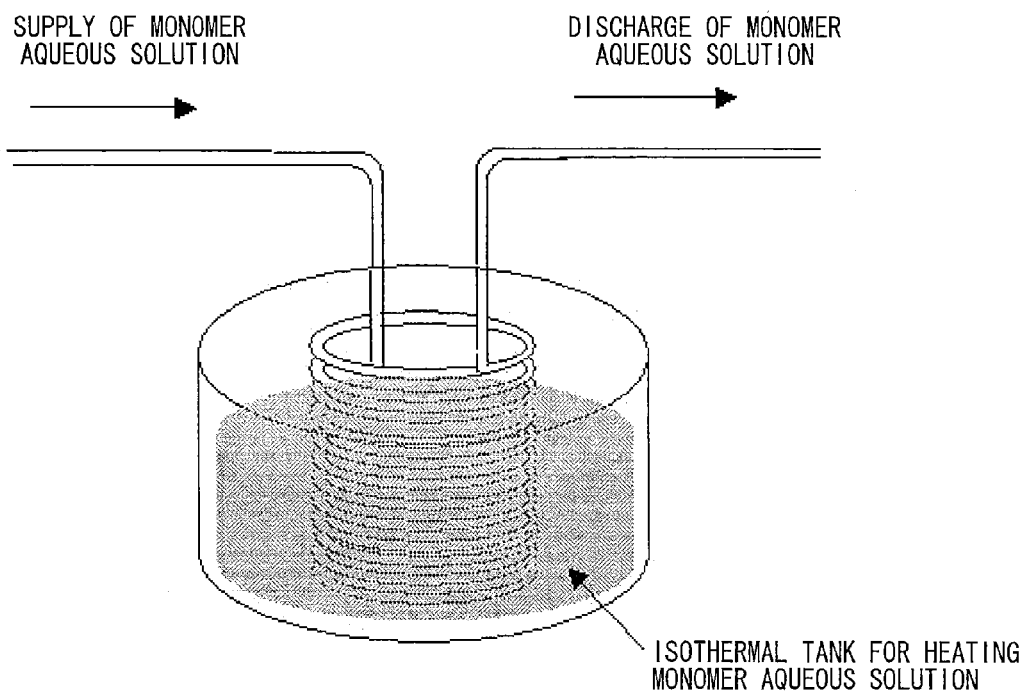
FIG. 1 is a perspective view illustrating one example of a device for use in a continuous heating method in which an acrylic acid-based monomer aqueous solution is heated according to a first method and a second method of the present invention are employed.

In the following, water-absorbable polyacrylic acid resin powder and a process for production thereof according to the present invention are described in detail. It should be noted that the scope of the present invention is not limited to the description and can be embodied with modifications other than the following exemplary embodiments but not departing from the gist of the present invention.

More specifically, the present invention shall not be construed as being limited to the following embodiments, may be modified in many ways within the scope of the following claims. The technical scope of the present invention can encompass any modifications obtainable by appropriately combining technical means disclosed in different embodiments.

[1] DEFINITION OF TERMS (1-1) "Water-Absorbable Resin Powder"

What is meant by the wording "water-absorbable resin powder" in the present invention is water-swellable water-insoluble polymer gelling agent. Note that being "water swellable" is to have CRC (centrifuge retention capacity, defined in ERT 441.2-02) of 5 [g/g] or more. Being "water insoluble" is to have Ext (water soluble content, defined in ERT 470.2-02) of 0 to 50 wt %.

The water-absorbable resin powder can be designed as suitable for its purposes, and is not limited to a particular structure. The water-absorbable resin powder is not limited to an embodiment in which the water-absorbable resin powder is totally a polymer (100 wt %). As long as the above properties are ensured, the water-absorbable resin powder may contain an additive or the like. In the present invention, a water-absorbable resin composition containing a small amount of additive is also referred to as the water-absorbable resin powder, collectively. Moreover, the water-absorbable resin powder may or may not be crosslinked. The water-absorbable resin may be in the form of sheet, fiber, film, gel, etc. Preferably, the water-absorbable resin is in the form of powder, more preferably in the form of powder having the following particle diameter and moisture content.

(1-2) "Water-Absorbable Polyacrylic Acid Resin Powder"

In the present invention, the wording "water-absorbable polyacrylic acid resin powder" means a polymer, which may contain a graft component as appropriate, and whose main component is acrylic acid and/or its salt (hereinafter, referred to acrylic acid (salt)) as its repeating unit.

More specifically, what is meant by the "water-absorbable polyacrylic acid resin powder" is a polymer in which acrylic acid (salt) accounts for 50 mol % to 100 mol % in the total monomer content (except a crosslinking agent) to be polymerized, preferably water-absorbable resin powder in which acrylic acid (salt) accounts for 70 mol % to 100 mol % in the total monomer content, more preferably water-absorbable resin powder in which acrylic acid (salt) accounts for 90 mol % to 100 mol % in the total monomer content, and especially preferably water-absorbable resin powder in which acrylic acid (salt) accounts for substantially 100 mol % in the total monomer content. Moreover, in the present invention, a polyacrylate (neutralized) polymer is also referred to as polyacrylic acid, collectively.

(1-3) "EDANA" and "ERT"

"EDANA" is abbreviation of European Disposables and Nonwovens Associations. "ERT" is abbreviation of EDANA Recommended Test Methods, which is a water-absorbable resin measuring method adopted as the European standard (substantially global standard). In the present invention, unless otherwise specified, the properties of the water-absorbable resin powder are measured according to the ERT master copy (Known Literature: 2002 revised version).

(a) "CRC" (ER 441. 2-02)

"CRC" stands for Centrifuge Retention Capacity, and means absorbency without pressure (hereinafter, may be refereed to as "absorbency". More specifically, CRC is absorbency (unit; g/g) measured by allowing 0.200 g of water-absorbable resin wrapped in unwoven cloth to freely swell with 0.9 wt % sodium chloride aqueous solution for 30 minutes and then draining the water-absorbable resin by using a centrifugal device.

(b) "AAP" (ERT 442.2-02)

"AAP" stands for Absorption Against Pressure, and means absorbency measured under load. More specifically, AAP is absorbency (unit; g/g) measured by allowing 0.900 g of water-absorbable resin wrapped to swell with 0.9 wt % sodium chloride aqueous solution for 1 hour under load of 2.06 kPa. Note that AAP is referred to as Absorption Under Pressure in ERT 442.2-02. AAP and AUP are substantially identical with each other. Sometime AAP is measured with load of 4.83 kPa (0.7 psi).

(c) "Ext" (ERT 470.2-02)

"Ext" stands for Extractables, and means water soluble content (water soluble component amount). More specifically, Ext is water soluble content (unit; wt %) measured by mixing 1 g of water-absorbable resin powder in 200 g of 0.9 wt % sodium chloride aqueous solution for 16 hours, and measuring an amount of polymer dissolved therein by pH titration.

(d) "PSD" (ERT 420.2-02)

"PSD" stands for Particle diameter Distribution, and means a particle diameter distribution measured by classification by sieving. Here, a weight average particle diameter (D50) and particle diameter distribution range is performed by the same method as one described in "(1) Average Particle Diameter and Distribution of Particle Diameter" in US patent 2006-204755.

(1-4) "Permeability Potential"

The "permeability potential" regards flowing of a liquid between particles of swollen water-absorbable resin powder under load or without load. The "permeability potential" is measured typically as SFC (Saline Flow Conductivity) or GBP (Gel Bed Permeability).

"SFC" is permeability potential of water-absorbable resin powder for 0.69 wt % sodium chloride aqueous solution under load of 2.07 kPa, and measured according to the SFC test method described in the Specification of U.S. Pat. No. 5,669,894. Moreover, "GBP" is permeability potential of water-absorbable resin powder for 0.69 wt % sodium chloride aqueous solution wherein the water-absorbable resin powder is under load or allowed to freely swell. GBP is measured according to the GBP test method described in pamphlet of the PCT international publication No. 2005/016393.

(1-5) Others

In this Specification, the expression "X to Y" for expression a range means "not less than X and not more than Y". The weight unit "t (ton)" means "Metric ton". Further, unless otherwise specified, "ppm" means "ppm by weight". Moreover, "weight" and "mass", "wt %" and "mass %", and "parts by weight" and "parts by mass" are synonymous with each other correspondingly herein. Further, the wording " . . . acid (salt)" means " . . . acid and/or salt thereof". The wording "(meth)acrylic" means "acrylic and/or methacrylic".

[2] PROCESS FOR PRODUCTION OF WATER-ABSORBABLE POLYACRYLIC ACID RESIN POWDER

A production process according to the present invention for production of the water-absorbable resin powder is a method performing foaming polymerization in order to attain a higher water absorbing rate, and is characterized in how to include cells, compared with the aforementioned Patent Literatures. By this method, bubbles are dispersed uniformly in a pre-polymerization monomer aqueous solution, thereby improving the resultant water-absorbable resin powder not only in water absorbing rate but also in degree of whiteness. Furthermore, the water-absorbable resin powder is attained by not sacrificing or almost not sacrificing the other properties of water-absorbable resin powder (such as permeability potential, bulk specific gravity, surface tension, absorbency against pressure, impact resistance (anti-damaging property) etc.), and further without requiring a costly raw material or device.

That is, a process (first method) according to the present invention is a process for producing water-absorbable polyacrylic acid resin powder, comprising (i) polymerizing an acrylic acid-based monomer aqueous solution containing bubbles, (ii) grinding hydrogel crosslinked polymer to fine gel particles during or after the polymerization, if necessary, and (iii) drying the hydrogel crosslinked polymer, the process further comprising bubbling by lowering solubility of a dissolved gas in the acrylic acid-based monomer aqueous solution in the presence of a surfactant and/or a dispersing agent so as to cause the acrylic acid-based monomer aqueous solution to contain the bubbles.

Here, the surfactant is added before the step of bubbling. Thus, the surfactant may be added after the step of polymerizing but it is preferable that the surfactant is added before the step of polymerizing.

That is, the production process according to the present invention is a process for production, comprising bubbling by lowering solubility of the dissolved gas in the acrylic acid-based monomer aqueous solution which may be partly prepared or may be fully prepared but which contains the surfactant and/or the dispersing agent by addition of the surfactant and/or the dispersing agent therein preferably before the step of polymerizing. The solubility of the dissolved gas may be carried out by, for example, heating the acrylic acid-based monomer aqueous solution, and/or adding a water soluble organic material to the acrylic acid-based monomer aqueous solution.

The step of bubbling should be performed at least before the step of polymerizing ends. Thus, the step of bubbling may be performed after the step of polymerizing starts. It is preferable that the step of bubbling be performed before the step of polymerizing.

In other words, a production process according to the present invention for production of water-absorbable resin powder is preferably arranged to comprise (i) polymerizing an acrylic acid-based monomer aqueous solution containing bubbles, (ii) grinding hydrogel crosslinked polymer to fine gel particles during or after the polymerization, if necessary, and (iii) drying the hydrogel crosslinked polymer, the process further comprising before the step of polymerizing, (A) (second method) heating the acrylic acid-based monomer aqueous solution which may be partly prepared or may be fully prepared but which contains the surfactant and/or the dispersing agent by addition of the surfactant and/or the dispersing agent therein preferably before the step of polymerizing, and/or (B) (third method) adding a water soluble organic material to the acrylic acid-based monomer aqueous solution which may be partly prepared or may be fully prepared but which contains the surfactant and/or the dispersing agent by addition of the surfactant and/or the dispersing agent therein preferably before the step of polymerizing.

In the first or third method, it is preferable that the water soluble organic material is acrylic acid, especially, non-neutralized acrylic acid. The water soluble organic material has a water content of preferably 20 wt % or less, more preferably 2 wt % or less, and further preferably 0.5 wt % or less. By adding acrylic acid low in water content to the acrylic acid-based monomer aqueous solution, acrylic acid, which is a power solvent for gas, lowers the solubility of the gas dissolved in the aqueous solution, thereby causing bubbling. A mixing ratio between the water soluble organic material and the acrylic acid-based monomer aqueous solution containing the surfactant and/or the dispersing agent may be determined as appropriate. The mixing ratio is preferably 1:9 to 9:1, more preferably 2:8 to 8:2, and especially preferably 3:7 to 7:3 by weight.

In the first to third methods, the step of bubbling by lowering the solubility of the dissolved gas so as to cause the acrylic acid-based monomer aqueous solution to contain the bubbles, the step of heating the acrylic acid-based monomer aqueous solution, and the step of adding the water soluble organic material to the acrylic acid-based monomer aqueous solution may be carried out under increased pressure or under reduced pressure. However, for the sake of easy operation, concise process, and simple device, these steps are carried out under substantial atmospheric pressure. Here, what is meant by the wording "substantial atmospheric pressure" is atmospheric pressure±10%, preferably ±5%, more preferably ±2%, further preferably ±1%, and especially preferably 0% (substantially identical with atmospheric pressure). In these methods, it is preferable that the pressure is not intentionally increased or reduced to change the pressure. However, releasing the monomer aqueous solution from piping, and heating are naturally cause a pressure change in the environment and such a pressure change is substantially 0%.

The first to third methods cause the acrylic acid-based monomer aqueous solution to contain the bubbles in the ways described above. It is preferable for the first to third methods to include introducing inert gas into the acrylic acid-based monomer aqueous solution before or after the step of lowering the solubility of the dissolved gas.

For the sake of stability of the bubbles thus generated, the first to third methods are preferably arranged such that a time period between the end of the step of lowering the solubility of the dissolved gas (i.e., the bubbling step) and the start of the start of polymerization in the step of polymerizing is more than 0 but not more than 300 seconds. It is more preferable that the time period is not more than 120 seconds. It is further preferable that the time period is not more than 60 seconds. It is especially preferable that the time period is not more than 30 seconds. If the time period exceeds 300 sections, the bubbles thus generated would merge together or disappear, thereby likely causing a failure to attain much improvement in the water absorbing rate.

(Pre-Polymerization Fully or Partly Prepared Acrylic Acid-Based Monomer Aqueous Solution)

In the present invention, the "acrylic acid-based monomer aqueous solution" is an aqueous solution of a monomer(s) which are mainly acrylic acid and/or its salt described later, and may contain, if necessary, a crosslinking agent, a graft component, a minute component (chelating agent, surfactant, a dispersing agent), etc., so as to contain constituents of the water-absorbable resin. It is possible to perform the polymerization with the acrylic acid-based monomer aqueous solution as such and a polymerization starter added thereto.

The acrylic acid may be not neutralized or may be a salt (fully neutralized or partially neutralized). Moreover, the monomer aqueous solution may exceed its saturation concentration. The acrylic acid-based monomer aqueous solution in the present invention encompasses a supersaturated aqueous solution or a slurry aqueous solution (aqueous dispersion solution) of the acrylic acid (salt). However, for better properties of the resultant water-absorbable resin powder, it is preferable that the acrylic acid-based monomer aqueous solution not saturated is used.

Moreover, a polymerization solvent for the monomer(s) is water, and therefore the acrylic acid-based monomer(s) are prepared as an aqueous solution thereof. Here, the aqueous solution is not limited to one whose solvent is water by 100 wt %. In the present invention, the aqueous solution encompasses ones containing another water soluble organic solvent(s) (e.g., alcohol), preferably by 0 to 30 wt %, and more preferably 0 to 5 wt %.

In the present invention, the acrylic acid aqueous solution is subjected to the lowering the solubility of the gas (first method), which is preferably the heating (second method) or the addition of the water soluble organic material (third method). The first to third methods according to the present invention encompass cases where 100 wt % acrylic acid (water-free or low-water-content acrylic acid, for example acrylic acid with water content of 2 wt % or less) is neutralized, because mixing a basis aqueous solution (for example, sodium hydroxide aqueous solution) into 100 wt % acrylic acid produces an acrylic acid aqueous solution (acrylic acid+ NaOH aqueous solution) right at beginning of the mixing of the basis aqueous solution.

In the present invention, the pre-polymerization fully prepared acrylic acid-based monomer aqueous solution is an acrylic acid-based monomer aqueous solution that has not been introduced into a polymerizer, or an acrylic acid-based monomer aqueous solution that has been introduced into the polymerizer but whose polymerization has not been started yet.

In the present invention, the partly-prepared (or work-in-process) acrylic acid-based monomer aqueous solution is an aqueous solution of acrylic acid and/or its salt, which is to be prepared as a monomer aqueous solution whose main component is acrylic acid and/or its salt, but to which not all components have been added. Typically, the partly-prepared acrylic acid-based monomer aqueous solution is an acrylic acid aqueous solution, a partly or fully neutralized acrylic acid salt aqueous solution, etc. The partly-prepared acrylic acid-based monomer aqueous solution is to be further neutralized, mixed with water as a solvent, or mixed with the minute component(s), thereby being prepared as the fully prepared acrylic acid-based monomer aqueous solution.

(Heating)

In the first or second method according to the present invention, the step of lowering the solubility of the dissolved gas so as to generate the bubbles and cause the acrylic acid-based monomer aqueous solution to contain the bubbles, that is, the step of heating the acrylic acid-based monomer aqueous solution lowers the solubility of the gas by heating the acrylic acid-based monomer aqueous solution. A heating range of the heating is +5° C. or more, more preferably in a range of +10° C. to +100° C., further preferably +20° C. to +90° C., and especially preferably +30° C. to +80° C., in consideration of an amount of the bubbles to be generated.

If the heating range is too large, this would result in poor stability of the bubbles before the polymerization. If the heating range is too small, the amount of the bubbles before the polymerization would be small. Either case would possibly result in insufficient improvement in water absorbing rate. In consideration of the water absorbing rate and the other properties, the monomer aqueous solution has a pre-heating temperature of preferably 0° C. to 60° C., and further preferably 20° C. to 50° C. Moreover, by the heating through the heating range, the monomer aqueous solution reaches a post-heating temperature of preferably 40° C. to 100° C. The post-heating temperature is more preferably within a later described range.

Figure 2:
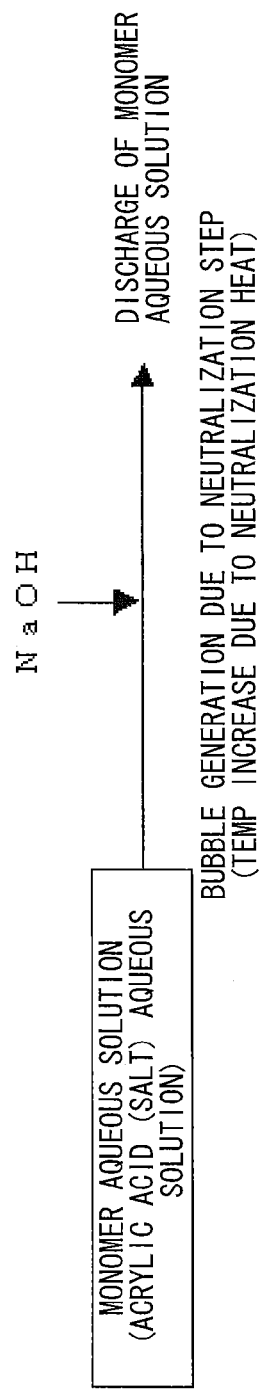
FIG. 2 is a flow diagram schematically illustrating a thermal bubbling method using neutralization of the acrylic acid-based monomer aqueous solution according to the first method and the second method of the present invention are employed.
Figure 4:
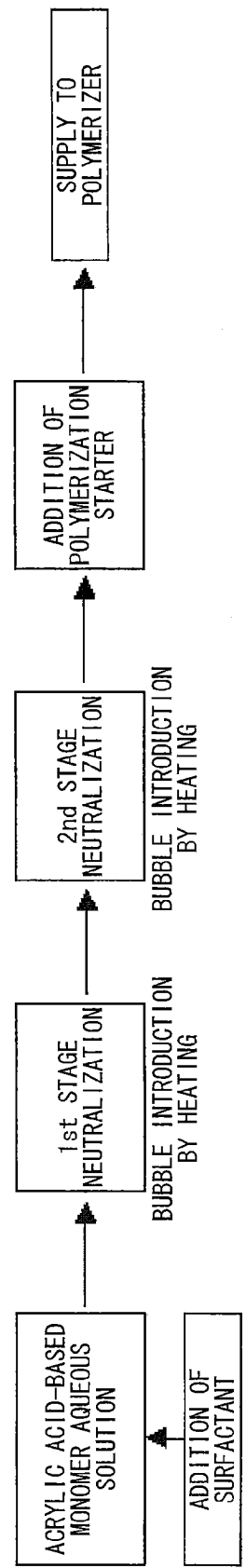
FIG. 4 is a flow diagram schematically illustrating a thermal bubbling method utilizing neutralization of the acrylic acid-based monomer aqueous solution, under the presence of the surfactant in Example 2.
Figure 5:
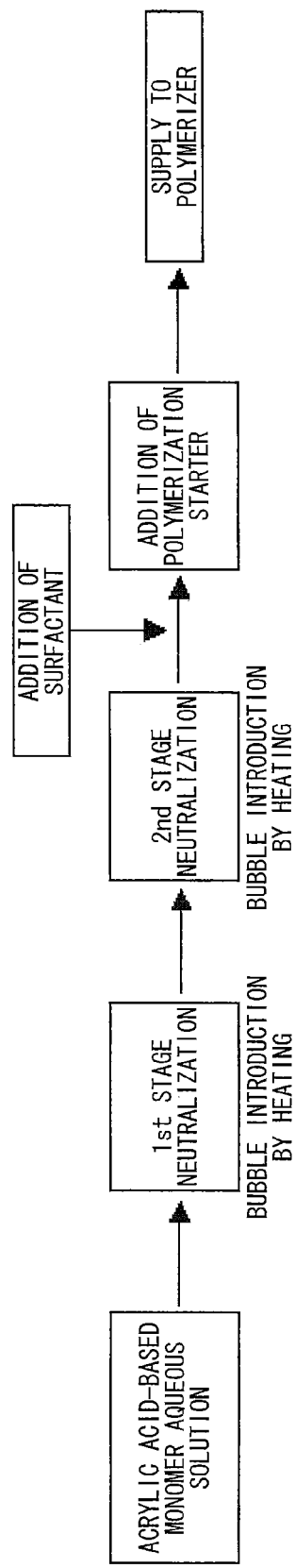
FIG. 5 is a flow diagram schematically illustrating a heating method using neutralization of an acrylic acid-based monomer aqueous solution in Comparative Example 3.
Figure 6:
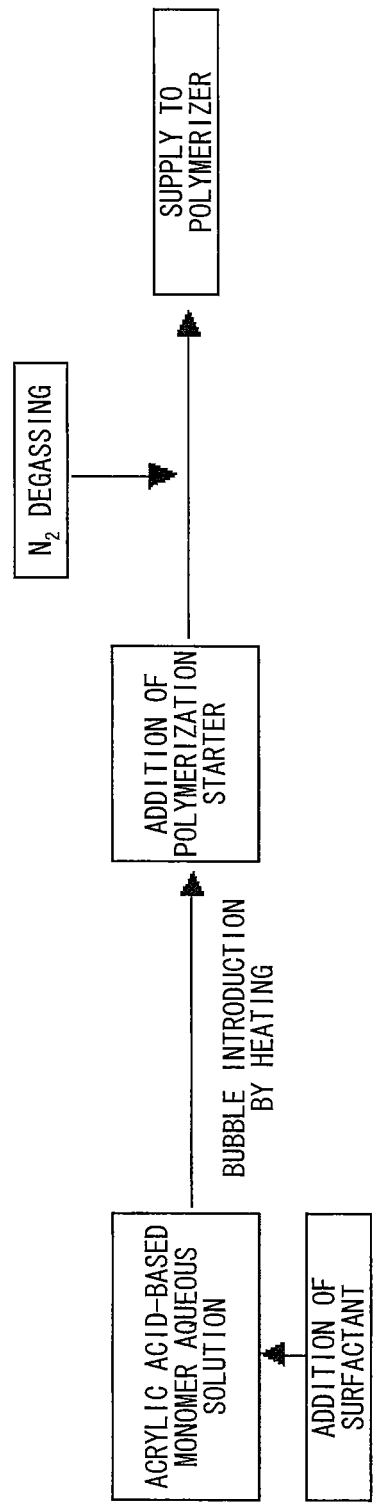
FIG. 6 is a flow diagram schematically illustrating an embodiment in which deoxidation is further carried out by using inert gas (for example, nitrogen) before the polymerization of the monomer aqueous solution in a thermal bubbling method for the acrylic acid-based monomer aqueous solution, as one preferable embodiment of the present invention, which can be applied to the first and second methods of the present invention.
Figure 7:
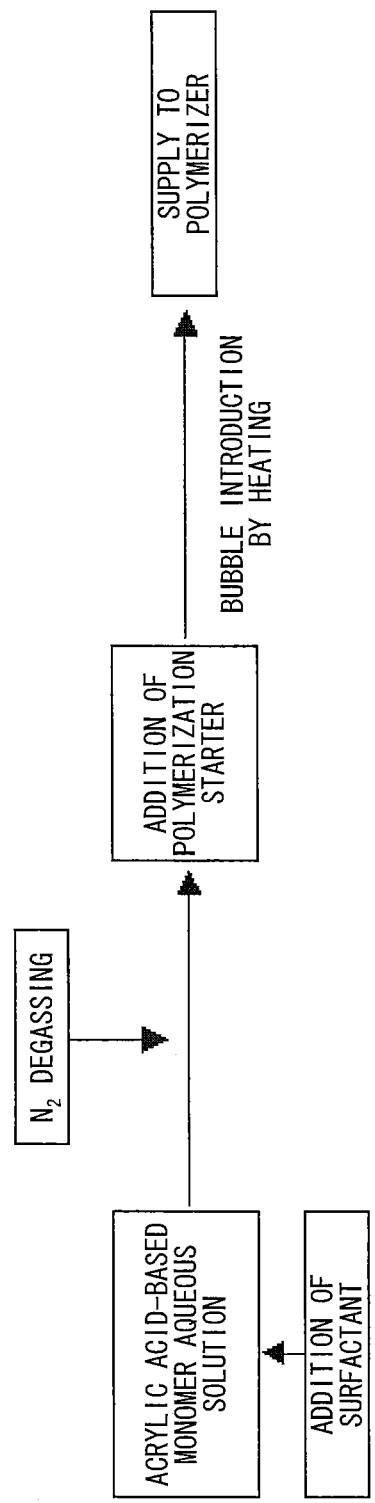
FIG. 7 is a flow diagram schematically illustrating an embodiment in which deoxidation is further carried out by using inert gas (for example, nitrogen) before the polymerization of the monomer aqueous solution in the thermal bubbling method for the acrylic acid-based monomer aqueous solution, as one preferable embodiment of the present invention, which can be applied to the first and second methods of the present invention.
Figure 8:
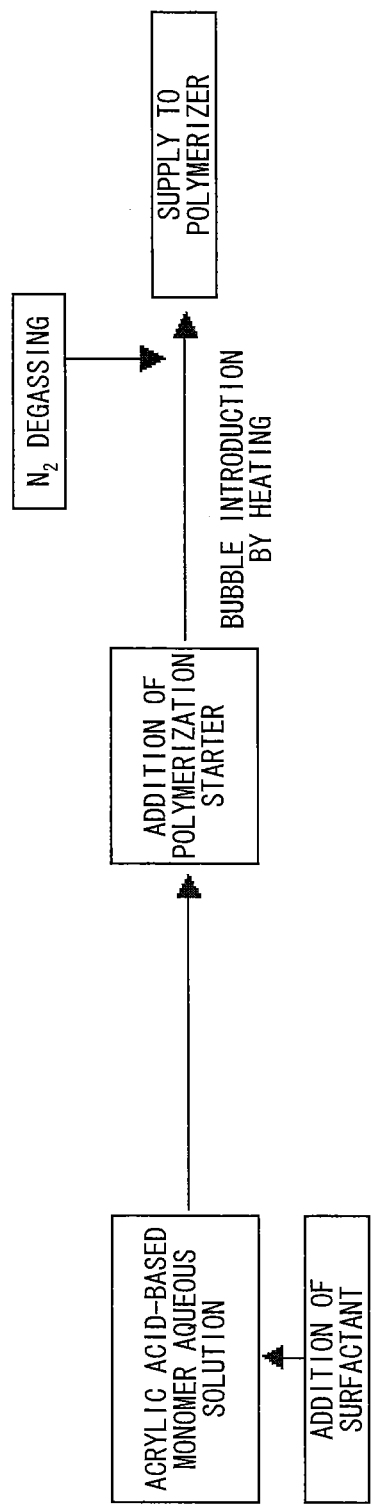
FIG. 8 is a flow diagram schematically illustrating an embodiment in which deoxidation is further carried out by using inert gas (for example, nitrogen) before the polymerization of the monomer aqueous solution in the thermal bubbling method for the acrylic acid-based monomer aqueous solution, as one preferable embodiment of the present invention, which can be applied to the first and second methods of the present invention.
Figure 9:
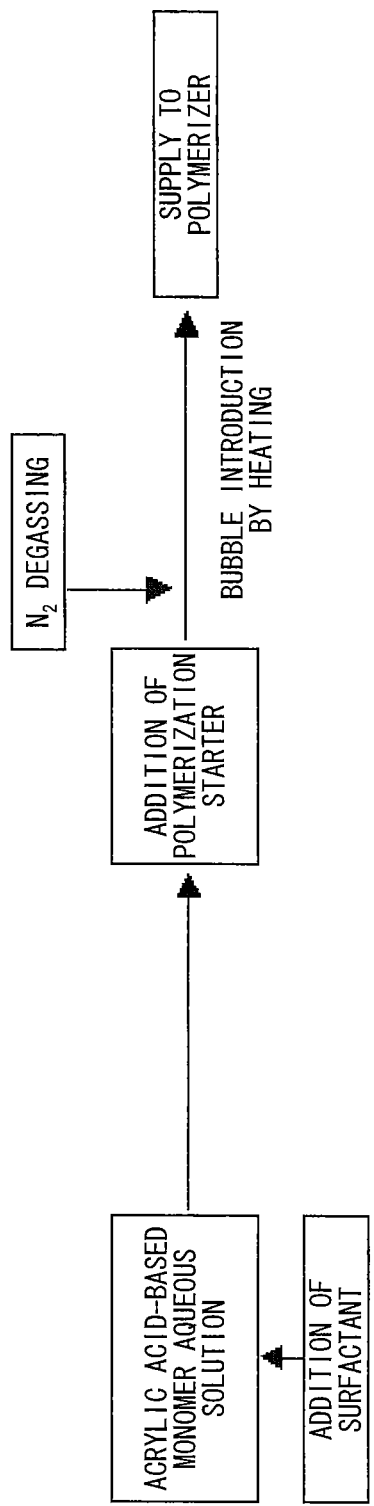
FIG. 9 is a flow diagram schematically illustrating an embodiment in which deoxidation is further carried out by using inert gas (for example, nitrogen) before the polymerization of the monomer aqueous solution in the thermal bubbling method for the acrylic acid-based monomer aqueous solution, as one preferable embodiment of the present invention, which can be applied to the first and second methods of the present invention.
Figure 10:
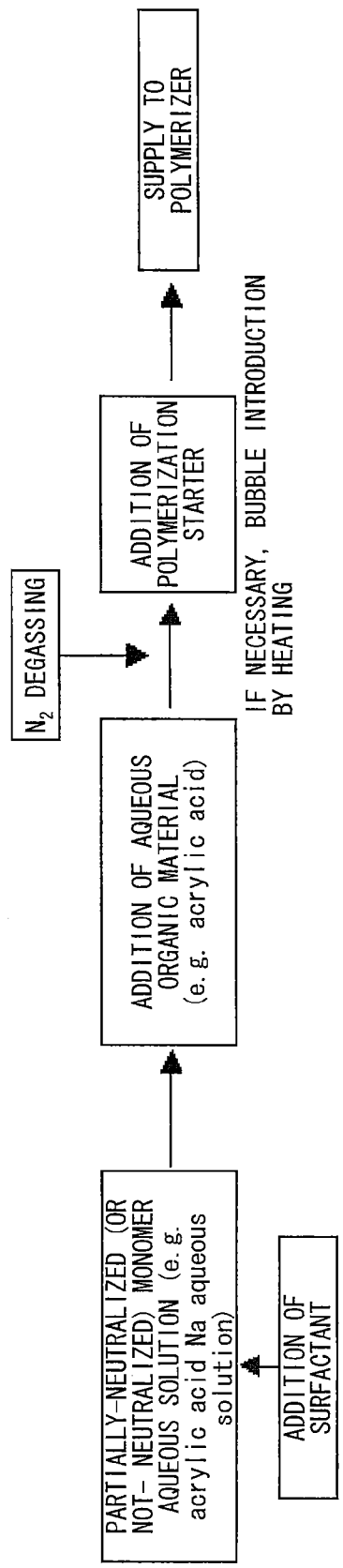
FIG. 10 is a flow diagram schematically illustrating how to lower gas solubility and perform the bubbling due to mixing a water-soluble organic compound in the acrylic acid-based monomer aqueous solution, which can be applied to the first method and a third method of the present invention.
Figure 11:
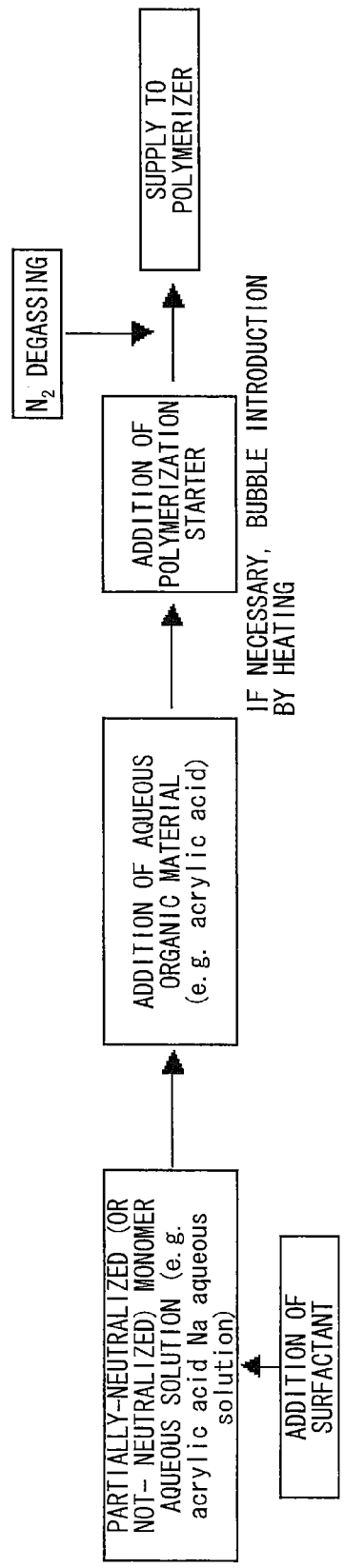
FIG. 11 is a flow diagram schematically illustrating how to lower gas solubility and perform the bubbling due to mixing a water-soluble organic compound in the acrylic acid-based monomer aqueous solution, which can be applied to the first method and a third method of the present invention.

For concise process and greater effect, the heating is preferably carried out by use of neutralization heat of acrylic acid containing the surfactant, or the acrylic acid aqueous solution containing the surfactant. FIGS. 2 and 4 are schematic flow diagram illustrating typical heating and bubbling, which are carried out by use of neutralization heat.

The neutralization heat of acrylic acid is 13.9 [kcal/mol] (at 25° C.). Specific heat of water is 1 [cal/° C./g] (at 25° C.). Specific heat of acrylic acid is 0.66 [cal/° C./g] (at 25° C.). More preferably, neutralization heat of acrylic acid heats up the acrylic acid aqueous solution. The heating range can be predicated from the neutralization heat and the specific heat.

Moreover, the heating by use of the neutralization heat (13.9 [kcal/mol] (at 25° C.)) of acrylic acid may be carried out in such a way that the acrylic acid aqueous solution is heated or cooled during neutralization reaction in order to control the heating range, or that the neutralization reaction is carried out with a reaction system that is thermally insulated.

In the first and second methods according to the present invention, the heating lowers the solubility of the gas, thereby generating bubbles in the acrylic acid aqueous solution. Such a system (which does not particularly limit the present invention) generates bubbles much finer than those prepared by the conventional bubbling methods described in Patent Literatures 18 to 35, etc. It is deduced that the object of the present invention is achieved by further stabilizing the bubbles with the surfactant and/or the dispersing agent.

Moreover, one example of heating other than the heating by use of the neutralization heat is heating carried out by heating the acrylic acid-based monomer aqueous solution. The acrylic acid-based monomer aqueous solution may be heated by means of a jacket or the like.

FIG. 1 is a view (schematic view) of a device for a continuous heating method for heating the acrylic acid-based monomer aqueous solution, to which method the first and the second method of the present invention is applicable. The device illustrated in FIG. 1 is a device employable in one embodiment of the step of bubbling carried out by heating the acrylic acid-based monomer aqueous solution.

Moreover, FIGS. 6 to 9 are flow diagram schematically illustrating some embodiments of the present invention for the lowering the solubility of the gas by heating in order to cause bubbling. The heating methods may be used in combination, and the heating may be carried out by a method other than these methods.

The production process according to the present invention for production of the water-absorbable resin powder can provide water-absorbable resin powder whose water absorbing rate (for example, FSR) is improved while maintaining the permeability potential (for example SFC). Therefore, preferably, the production process according to the present invention can provide water-absorbable resin powder whose FSR and SFC are excellent without sacrificing the other properties. Preferably ranges of the properties will be described later. Especially, SFC of the water-absorbable resin powder is preferably 20 [×10$^{-7}$·cm$^3$·sec·g$^{-1}$] or more, and FSR is 0.25 [g/g/sec) or more. Further preferably ranges of SFC and FSR will be described in "(3-3) SFC (Saline Flow Conductivity)" and "(3-5) FSR (water absorbing rate)".

(2-1) Step of Preparing Acrylic Acid-Based Monomer Aqueous Solution (Step of Dissolving and Dispersing)

The step of preparing acrylic acid-based monomer aqueous solution is a step for obtaining acrylic acid-based monomer aqueous solution in which the gas is dispersed. Hereinafter, this step is described more specifically.

(2-1-1) Monomer Composition

Any acrylic acid-based monomer may be used in the present invention, provided that the water-absorbable resin powder can be produced therefrom by polymerization. The followings can be exemplified as such an acrylic acid-based monomer: anion type unsaturated monomers and salt thereof such as (meth)acrylic acid, (anhydrous)maleic acid, itaconic acid, cinnamic acid, vinylsulfonic acid, allyltoluenesulfonic acid, vinyltoluene sulfonic acid, styrene sulfonic acid, 2-(meth)acrylamide-2-methylpropanesulfonic acid, 2-(meth)acryloyl ethanesulfonic acid, 2-(meth)acryloyl propanesulfonic acid, and 2-hydroxyethyl(meth)acryloyl phosphate; mercapto group-containing unsaturated monomers; phenol hydroxide group-containing unsaturated monomers; amide group-containing unsaturated monomers such as (meth)acrylamide, N-ethyl(meth)acrylamide, N,N-dimethyl (meth)acrylamide; amino group-containing unsaturated monomers such as N,N-dimethylamino ethyl (meth)acrylate, N,N-dimethylaminopropyl(meth)acrylate, and N,N-dimethylaminopropyl(meth)acrylamide; and the other monomers.

For the water-absorbable polyacrylic acid resin powder, the amount of acrylic acid and/or its salt is used is 50 mol % or more, preferably 70 mol % or more, more preferably 80 mol % or more, further preferably 90 mol % or more, and especially preferably 95 mol % or more (upper limit is 100 mol %) with respect to total monomer content (except an internal crosslinking agent later described). It should be noted that the "polyacrylic acid" in the present invention is defined as encompassing polyacrylate (especially, monovalent polyacrylate).

There is no particular limitation as to neutralization rate of the monomer(s) and the polymer derived from the monomer(s). If necessary, the polymer gel may be neutralized after the polymerization. In application such as sanitary goods etc. which may touch a human body, the neutralization after the polymerization is not necessary. The neutralization rate is preferably in a range of 40 mol % to 90 mol %, more preferably 50 mol % to 80 mol %, and further preferably 60 mol % to 74 mol %. To achieve the object of the present invention, it is preferable that the neutralization rate is within these ranges, because a low neutralization rate tends to result in a low water absorbing rate (for example, FSR), and a high neutralization rate tends to lower reactivity of the surfactant, thereby resulting in low permeability potential (for example, SFC) or low absorbency against pressure (for example, AAP). That is, the acidic monomer such as acrylic acid or the like, or the polymer derived therefrom may be partly or totally salt in view of the absorbency without pressure (CRC) or the water absorbing rate (FSR). Preferably, the acidic monomer or the polymer derived therefrom may be monovalent salts such as sodium salt, lithium salt, potassium salt, ammonium salt, amine salt. Especially preferably, the acidic monomer or the polymer derived therefrom may be alkaline metal salt. Further preferably, the acidic monomer or the polymer derived therefrom may be sodium salt and/or potassium salt. Among them, sodium salt is more preferable than the others in terms of cost and property.

In the polymerization, an internal crosslinking agent is used if necessary. As such an internal crosslinking agent, a conventionally well-known internal crosslinking agent can be used. More specifically, for example, the following crosslinking agents may be used: N,N'-methylenebis(meth)acrylamide, (poly)ethylene glycol di(meth)acrylate, (poly)propyleneglycol di(meth)acrylate, trimethylolpropane tri(meth) acrylate, glycerine tri(meth)acrylate, glycerine acrylate methacrylate, ethyleneoxide modified trimethylol propane tri(meth)acrylate, pentaerythritol hexa(meth)acrylate, triallyl cyanurate, triallyl isocyanurate, triallyl phosphate, triallylamine, poly(meth)allyloxy alkanes, (poly) ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl(meth) acrylate; and the other cross linking agent. In consideration of reactivity, one or more among them can be used. Especially, it is desirable to use a compound which has two or more polymerizable unsaturated groups.

An amount of the internal crosslinking agent can be determined as appropriate, depending on desired properties of the water-absorbable resin. In general, the amount of the internal crosslinking agent is preferably in a range of 0.001 mol % to 5 mol %, more preferably in a range of 0.005 mol % to 2 mol %, further preferably in a range of 0.01 mol % to 1 mol %, with respect to a total amount of the acrylic acid-based monomer(s). If the amount of the internal crosslinking agent is less than 0.001 mol %, the resultant water-absorbable resin powder has a high water soluble content, thereby resulting in a risk of failing to ensure a sufficient absorbing amount under pressure. On the other hand, if the amount of the internal crosslinking agent exceeds 5 mol %, this would possibly result in a high crosslinking density, thereby resulting in an insufficient absorbing amount of the resultant water-absorbable resin powder. Note that the internal crosslinking agent may be added to the reaction system at once or by portions.

(2-1-2) Dispersion of Bubbling (Step of Bubbling)

A method of dispersing the bubbles in the acrylic acid-based monomer aqueous solution is a method for bubbling the dissolved gas in the aqueous solution in the presence of the surfactant and/or the dispersing agent and effectively dispersing the resultant bubbles as fine bubbles (micro bubbles or nano bubbles). Here, a gas (for example, inert gas) may or may not be introduced in the aqueous solution so as to cause the aqueous solution to contain the dissolved gas therein.

More specifically, the method of dispersing the bubbles in the acrylic acid-based monomer aqueous solution is at least one of methods (a) and (b).

(Method (a); Dispersing by Heating the Acrylic Acid-Based Monomer Aqueous Solution)

One method of dispersion the bubbles in the acrylic acid-based monomer aqueous solution is heating the fully-prepared acrylic acid-based monomer aqueous solution that have been prepared by mixing the monomer(s) and/or its salt, and the internal crosslinking agent and water if necessary, or heating the partially prepared acrylic acid-based monomer aqueous solution at its preparation stage. By either way, the solubility of the gas in the aqueous solution can be lowered.

The heating of the fully-prepared acrylic acid-based monomer aqueous solution may be carried out, for example, by passing the acrylic acid-based monomer aqueous solution through a heat exchanger including piping or a vessel, by electronic irradiation, or the like. It is preferable that the acrylic acid-based monomer aqueous solution is heated to a temperature high enough to lower the solubility of the gas. More specifically, the acrylic acid-based monomer aqueous solution is heated to a temperature in a range of 40° C. to a boiling point of the aqueous solution. More preferably, the acrylic acid-based monomer aqueous solution is heated to a temperature in a range of 50° C. to 100° C. Further preferably, the acrylic acid-based monomer aqueous solution is heated to a temperature in a range of 60° C. to 98° C. Most preferably, the acrylic acid-based monomer aqueous solution is heated to a temperature in a range of 70° C. to 95° C. Moreover, heating time is preferably 60 seconds or shorter, more preferably 30 seconds or shorter, and further preferably 10 seconds or shorter, in order to heat the monomer aqueous solution rapidly thereby to produce bubbles as much as possible.

The heating of the partly-prepared acrylic acid-based monomer aqueous solution is carried out by, for example, utilizing the neutralization heat (13.9 [kcal/mol] (at 25° C.)) generated in the step of increasing a degree of neutralization of the monomer(s). The utilization of the neutralization heat may be carried out by a single-staged neutralization or multi-staged neutralization (two-staged neutralization). Moreover, the neutralization may be carried out continuously or batch-wise. Furthermore, the neutralization may be carried out to reach a predetermined neutralization rate via a single stage or via multi stages (for example, two stages). The two-staged neutralization is carried out by adding a base by two portions. FIG. 4 and Example 2 etc. describe such neutralization. The gas may have been dissolved in or dispersed in the monomer aqueous solution before the heating, in order to generate a greater amount of gas by the heating.

(Method (b); Adding the Water Soluble Organic Material in the Monomer Aqueous Solution in Preparing the Acrylic Acid-Based Monomer Aqueous Solution)

One example of the method for dispersing the bubbles in the acrylic acid-based monomer aqueous solution is to lower the solubility of the gas by mixing a water soluble organic material to the acrylic acid-based monomer aqueous solution in preparing the acrylic acid-based monomer aqueous solution by mixing the monomer(s) and/or its salt, and if necessary the internal crosslinking agent and water, wherein an amount of the gas dissolved in the water soluble organic material is zero, little, or less than in the acrylic acid-based monomer aqueous solution or the water with which the water soluble organic material is to be mixed. The water soluble organic material is an organic compound with an oxygen solubility of preferably 0.02 [ml/ml] or less, more preferably 0.01 [ml/ml] or less, especially preferably 0.005 [ml/ml] or less. For example, a monomer (for example acrylic acid) containing no gas is mixing to the acrylic acid-based monomer aqueous solution which contains the gas (the dissolved gas), thereby vaporizing gas that cannot stay dissolved in the aqueous solution after the mixing, and dispersing fine bubbles of the gas in the aqueous solution.

The bubbles introduced in the acrylic acid-based monomer aqueous solution by the method (a) or (b) have a number average diameter (volume average particle diameter) of preferably 50 μm or less, more preferably 50 nm (more preferably 10 μm) to 500 μm, and further preferably 100 nm (more preferably 10 μm) to 100 μm.

If the average diameter of the bubbles is less than 50 nm, the surface area of the bubbles could not be large enough, thereby resulting in poor water absorbing rate. Moreover, if the average diameter of the bubbles exceeds 500 μm, the resultant water-absorbable resin powder will be poor in strength thereby being fragile.

The solubility of the gas in water is dependent on how much the temperature is and which kind of gas the gas is. For example, solubilities of some gases to 25° C. water are as follows: carbon dioxide gas (1.05 [ml/ml]), oxygen (0.0285 [ml/ml]), and nitrogen (0.0147 [ml/ml]). The solubility of these gases are lowered by heating or mixing the water soluble organic material (more preferably acrylic acid), thereby generating the bubbles, which are dispersed in the acrylic acid aqueous solution by the surfactant or the dispersing agent. The amount of the bubbles is determined by the kind of the gas and how to lower the solubility (i.e., the heating range and the mixing ratio of the water soluble organic material). the amount of the bubbles dispersed in the acrylic acid-based monomer aqueous solution is preferably such that the monomer aqueous solution is increased in volume by 1.01 to 1.1 times, more preferably by 1.02 to 1.08 times.

(2-1-3) Gas

The production process according to the present invention disperses the bubbles by lowering the solubility of the dissolved gas in the acrylic acid-based monomer aqueous solution. However, the bubbles may be generated by introducing a gas in the acrylic acid-based monomer aqueous solution from outside, so as to disperse the bubbles in the acrylic acid-based monomer aqueous solution. That is, the bubbles dispersed in the acrylic acid-based monomer aqueous solution are attained by lowering the solubility and, in some cases, further introducing a gas in the acrylic acid-based monomer aqueous solution from outside. In such a case, the gas to form the bubbles dispersed in the acrylic acid-based monomer aqueous solution may be oxygen, air, nitrogen, carbon dioxide gas, ozone, or a mixture thereof. Preferably, the gas is an inert gas such as nitrogen, carbon dioxide, or the like. Further preferably, in order to facilitate the polymerization and reduce the cost, air and nitrogen are more preferable. Pressure during or after the introduction of the gas may be atmospheric pressure, increased pressure, or reduced pressure, as appropriate. Moreover, one preferable method for introducing the gas from outside is described in Japanese Patent Application, Tokugan, No. 2009-292318 (Filing date: Dec. 24, 2009), and the PCT application PCT/JP2010/001004 filed claiming priority based thereon. The method will be described in "(2-1-4) Gas introducing method" below.

(2-1-4) Gas Introducing Method Additionally Employed as Needed

In the production process according to the present invention, the bubbles are dispersed by lowering the solubility of the dissolved gas in the acrylic acid-based monomer aqueous solution. However, the gas may be introduced from outside additionally. In this case, the gas introduced from outside is mixed with the acrylic acid-based monomer aqueous solution. The introduction of the gas may be carried out by well-known methods such as static mixer method, cavitation method, venturi method or the like, solely or in combination. Further, it is preferable to introduce micro bubbles (or nano bubbles), because the introduction of micro bubbles (or nano bubbles), can introduce the gas in a greater amount. That is, it is preferable to additionally employ the introduction of micro bubbles or nano bubbles, as in Examples 5 and 6 described below.

The dissolving and/or dispersing the gas in this way may be carried out before or after the step of bubbling described above. In order to introduce more stable bubble, it is preferable that the step of lowering the solubility according to the present invention is carried out after introducing the gas in advance, especially preferably after introducing micro bubbles or nano bubbles.

For example, the following methods of introducing micro bubbles are employable solely or in combination in the present invention: (a) pressuring the monomer aqueous solution and the gas; (b) creating a swirling flow of the monomer aqueous solution and the gas; (c) mixing the gas into the monomer aqueous solution via pores. At least one of these methods may be adopted. In the following, these methods are explained.

(a) Pressuring the Monomer Aqueous Solution and the Gas

As the method of introducing micro bubbles, a pressure dissolving method is preferably use, in which the micro bubbles are introduced by pressuring the monomer aqueous solution and the gas. More specifically, the gas is dissolved in the monomer aqueous solution by applying pressure of preferably 100 kPa to 1000 kPa (absolute pressure), more preferably 200 kPa to 400 kPa, and especially preferably 250 kPa to 350 kPa, approximately as absolute pressure. Then, flushing is carried out to release the monomer aqueous solution via a decompression valve, thereby causing decompression to cause the gas to be oversaturated and thereby released into the solution as micro bubbles. The solubility of the gas in the solution follows the Henry's law (p=HC) and determined by temperature and pressure. Via the pressuring, the bubbles of the dissolved gas are obtained and dispersed.

Moreover, in order to control the solubility or dispersion of the gas, it is preferable to further apply a shear force to the mixture of the monomer aqueous solution and the gas before or during the pressuring, if necessary. The shear force is applied by using a high-rotation pump or the like. It is preferable that the gas is finely dispersed by the shear force and then pressured. After the shear force is applied to the monomer aqueous solution and the gas, the pressure is increased to be in a range of 0.1 MPa to 1 MPa, and is then released as described above.

(Oversaturation)

One example of the pressure dissolving method is to oversaturate the monomer aqueous solution with the gas in preparing the acrylic acid-based monomer aqueous solution. Therefore, the gas content in the acrylic acid-based monomer aqueous solution in which the gas is dissolved and/or dispersed exceeds the saturation solubility of the gas at a certain temperature by preferably 1.01 to 10 times, more preferably 1.05 to 5 times, and further preferably 1.06 to 3 times.

(b) Forming a Swirling Flow of the Monomer Aqueous Solution and the Gas

Another preferable example of the method of introducing micro bubbles is to form a swirling flow of the monomer aqueous solution and the gas. This method swirls a gas-liquid two-phase flow and disperses the bubbles at an outlet (outlet of a mixing machine). A ratio between a gas flow rate and a liquid flow rate is preferably in a range of 1/7 to 1/15. A swirling rate is preferably at 10 rev to 10000 rev per second and more preferably at 100 rev to 1000 rev per second.

A swirling fine bubble generating device to use is not particularly limited and may be one exemplified in PCT international publication, No. 00/69550 A, Japanese patent application publication, Tokukai, No. 2003-205228, Japanese patent application publication, Tokukai, No. 2000-447 A, Japanese patent application publication, Tokukai, No. 2006-116365 A, etc.

(c) Mixing the Gas into the Monomer Aqueous Solution Via Pores

One method for introducing micro bubbles is to generate bubbles via pores of one of various kinds of porous material, films, filters, and the like. A porous glass ($Na_2O$—$CaO$—$Al_2O_3$—$B_2O_3$—$SiO_2$ glass) or the like is employed. Preferably a surfactant is used in a later-described range such as more than 0 but not more than 0.03 wt %, for example. This method may be performed by using Kinoshita-type glass ball filter (filter particle No. 4) made by Kinoshita Rika Kyogo Co. Ltd.

(Micro Bubble Generating Device)

In order to introduce the micro bubbles, it is possible to use a micro bubble generating device having a function of pressuring the monomer aqueous solution and the inert gas, or generating a swirling flow of the monomer aqueous solution and the inert gas. Operation of the micro bubble generating device can suspend and maintain the generated micro bubbles in the monomer aqueous solution until the polymerization is started.

The micro bubble generating device applicable to the present invention is not limited to a particular one, and may be one commercially available. Some examples of the commercially available micro bubble generating devices are listed below.

OHR Line Mixer (OHR Laboratory Corporation)

M-type micro bubble generating device (Nanoplanet Research Institute Corporation)

Heavy-use microbuble generating device SMB-450 (Ishimaru Shoko Inc.)

Microbubble generating device Mbelife (Kansai Automation Equipment Co. Ltd.)

In-build ball type bubble generating device MBG (Nishida Tekkou Co. Ltd.)

Ponparator (Teikokuk Electric MFG. Co. Ltd.)

The micro bubble generating device has a water inlet and a water outlet. When a liquid (water or monomer(s)) is introduced under pressure of a certain level or greater, the gas dissolved in the water is gathered in a center portion inside the micro bubble generating device due to density differences, thereby forming a gas axis. Consequently, a pressure gradient is formed between peripheries and the center portion inside the micro bubble generating device. In such a case, the gas axis is substantially in a vacuum state at its center portion. Meanwhile, pressured water moving to be ejected out abuts against water flowing into the vacuum state (super negative pressure state) of the gas axis. In addition, when the gas axis being swirling passes through between the pressured water moving to be ejected out and the water flowing into the vacuum state, the gas is sheared thereby being finely divided into micro bubbles.

In the present invention, the micro bubbles generated by the micro bubble generating device has a number average diameter preferably in a range of 50 nm (more preferably 10 μm) to 500 μm, and more preferably in a range of 100 nm (more preferably 10 μm) to 100 μm. If the bubbles had an average diameter less than 50 nm, they would fail to have a large surface area, thereby possibly resulting in poor water absorbing rate. Moreover, if the average diameter exceeded 500 μm, the resultant water-absorbable resin powder would be poor in strength, thereby being fragile.

Moreover, an amount that the micro bubble generating device processes can be set as appropriate according to the desired properties of the water-absorbable resin powder, etc. However, it is preferable that a flow rate of the monomer aqueous solution is larger. The flow rate of the monomer aqueous solution is preferably 500 [kg/hr], more preferably 1000 [kg/hr], and further preferably 2000 [kg/hr]. Such a production amount per hour is not restricted to the case where the micro bubble generating device is used. In an industrial large-scale production, the production process according to the present invention is generally applicable. An upper limit of the production amount can be determined as appropriate, but is preferably 300 ton/hr or less. Thus, the production process according to the present invention is preferably applied to a continuous production process, especially to a continuous production process with the production amount.

(Other Method Additionally Applicable if Necessary)

The production process according to the present invention may employ the following methods (1) to (8) in addition to the methods (a) to (c), or the use of the micro bubble generating device.

(1) Static Mixer Method

Examples of the static mixers encompass: a static mixer configured to mix fluid when the fluid passes an element fixed inside a tube, without having a movable portion: an OHR mixer having a circular tuber having a spiral flow directing section and mushroom-like protrusions, by which a gas-liquid two-phase flow is broken to generate micro bubbles; etc.

(2) Cavitation Method

A gas dispersing device is configured to have a flow path modified to have a cavitation intentionally to generate micro bubbles.

(3) Combinational Use of a Centrifugal Pump and a Swirling Flow Micro Bubble Generating Device The centrifugal pump causes stirring effect of swirling and pressuring so as to dissolve the gas in the solution, and gat not dissolved by this is subjected to a swirling flow micro bubble generating device so as to be converted into micro bubbles.

(4) Venturi Method

By flowing gas and liquid into a straw section (narrow section) concurrently, a sudden change in a liquid flow rate occurs, thereby producing shock waves. The shock waves break large bubbles into micro bubbles.

(5) Stirring Method

Stirring blades are rotated at a high speed, thereby to intake a gas autarchically.

(6) Ultrasonic Wave Method

Micro bubbles are generated by use of ultrasonic waves whose frequency, pressure amplitude, etc. are set as appropriate.

(7) Phase Change Method

When a mixture gas of gas (nitrogen gas) and steam is blown into a liquid via a narrow nozzle, the steam is condensed, thereby leaving bubbles of the gas (nitrogen gas) not condensed.

(8) Electrolysis Method

Water electrolysis is utilized to generate bubbles of micro order.

Among them, it is preferable in terms of effect to further perform shearing treatment to the gas-liquid phase of the monomer aqueous solution and the gas in the step of preparing the acrylic acid-based monomer aqueous solution, wherein the shearing treatment is carried out by (3) combinational use of a centrifugal pump and a swirling flow micro bubble generating device, or the use of a static mixer (typically an OHR mixer) that can provide shearing and swirling.

For generating micro bubbles, one of the methods (a) to (c) and (1) to (8) can be employed. It is preferable to employ (a) or (b). It is more preferable to employ (a). If necessary, sharing force application by use of the micro bubbles generating device may be employed.

(Pressure Releasing Time)

When the method for bubbling is the pressure dissolving method (a) or the use of micro bubble generating device, the gas and the monomer aqueous solution are put under pressure greater than the atmospheric pressure (preferably under pressure in the range later-described, or under pressure in a range of 0.1 MPa to 1 Mpa (absolute pressure)), and then released into the atmospheric pressure (or reduced pressure, especially minutely reduced pressure of −10 mmHg or less), so as to generate the bubbles with controlled quantity and size. It is preferable to control the bubbles by controlling the pressure, temperature, and releasing time, especially the releasing time. By this, it is possible to obtain the water-absorbable resin, in which high water-absorbing rate and as well as a high permeability potential and a high impact resistance are attained as targeted.

One preferable method of bubbling is as follows. In any one of the methods (a) to (c) or inside the micro bubble generating device, pressure application is carried out in preparing the monomer aqueous solution by mixing acrylic acid, its salt, the solvent, the crosslinking agent, and/or the polymer starter, so as to produce a pressure greater than the atmospheric pressure inside the tube or device. Then, the monomer aqueous solution is supplied to a polymerizing device, and released in the atmospheric pressure when the polymerization is started.

That is, in the various micro bubble generating systems, the pressure releasing cause the dispersed bubbles to swell and merge with each other. Depending on how far the swelling and merging occur, the amount and size of the bubbles remained finally in the polymer gel are changed. Herein, a time between the releasing of the pressured monomer aqueous solution into the atmospheric pressure and the start of the polymerization is referred to as T1 (second). It is important to define the time between the pressure releasing of the reaction liquid thus supplied and the gelling of the reaction liquid so as to fix the bubbles. By appropriately controlling the temperature and the starter, it is preferable to control T1 such that 0<T1<T, and it is more preferable to control T1 such that 0<T1<½T.

Here, T1 is the time between the releasing into the atmospheric pressure and the start of the polymerization, and T is a time between the releasing into the atmospheric pressure and when the monomer aqueous solution regains a kaolin turbidity that the monomer aqueous solution had before the gas is dissolved or dispersed in the monomer aqueous solution.

T1 is found by white turbidity of the monomer aqueous solution (due to the generation of the polymer) or temperature increase (1° C. or more) due to polymerization heat. Meanwhile, T is found by measuring a time period (T) from dispersing the gas in the monomer aqueous solution without the starter in a measuring cylinder of 100 ml, and disappearing the bubble-caused white turbidity after letting the monomer aqueous solution stand at room temperature under the atmospheric pressure, as described later. Here, the white turbidity is generally caused due to bubbles larger than the wavelength of visible light. Nano bubbles do not influence the white turbidity substantially. This will be explained later again in the section regarding the turbidity (kaolin turbidity).

A lower limit of T1 is determined as appropriate. Preferably, the lower limit is a defoaming time (preferably 5 seconds or longer, further preferably in a range of 10 to 3600 seconds). An upper limit of T1 is determined depending on the monomer composition including the amount of the surfactant and the method of bubbling.

So far, the method (step) for introducing the gas from outside, which method is employed additionally if necessary, is described. Hereinafter, the step for bubbling by lowering the solubility according to the present invention is further explained.

(2-1-5) Dissolved Gas

In the present invention, the gas may be introduced into the acrylic acid-based monomer aqueous solution from outside if necessary. However, it is important in the present invention that the dissolved gas is turned into bubbles by the step of lowering the solubility of the gas.

In the present invention, the bubbles are dispersed or dissolved in the monomer aqueous solution by lowering the solubility of the gas by heating the acrylic acid-based monomer aqueous solution or by adding the water soluble organic material into the acrylic acid-based monomer aqueous solution. Therefore, a greater dissolved gas content is preferable before the step of lowering the solubility of the gas. The dissolved gas content in the monomer aqueous solution before the step of lowering the solubility of the gas is preferably more than 1 ppm, more preferably in a range of 2 ppm to 50,000 ppm, further preferably in a range of 3 ppm to 30,000 ppm, and most preferably in a range of 3 ppm to 10,000 ppm. The amount of the gas can be determined as appropriate depending on the type of the gas, temperature, the composition of the acrylic acid-based monomer aqueous solution, etc.

(2-1-6) Surfactant and Dispersing Agent

In the present invention, the use of the surfactant and/or the dispersing agent makes it possible to stably suspend the bubbles. Further, by appropriately selecting the kind and amount of the surfactant and/or the dispersing agent, it is possible to obtain the water-absorbable resin powder with desired properties. Preferably, the surfactant is a non-polymer surfactant and the dispersing agent is a polymer dispersing agent.

An amount of the surfactant and/or the dispersing agent to use can be determined as appropriate depending of the type of the surfactant and/or the dispersing agent. Preferably, the amount of the surfactant and/or the dispersing agent to use is such an amount that gives the resultant water-absorbable resin powder a surface tension of 60 [mN/m] or greater. Further preferably the amount of the surfactant and/or the dispersing agent to use is such an amount that gives the resultant water-absorbable resin powder a surface tension in a range later described in "(3-7) surface tension".

It is not preferable that the surface tension of the resultant water-absorbable resin powder is less than 60 [mN/m], because, if so, rewetting in a disposable diaper to which the water-absorbable resin powder is used tends to be greater in amount. In order not to lower the surface tension, it may be preferable to use a surfactant reactive or polymerizable with the water-absorbable resin powder or its monomer(s). For example, it may be preferable to use a surfactant having an unsaturated polymerisable group (especially, $\alpha$, $\beta$-unsaturated double bond) or a reactive group (hydroxyl group or amino group). Moreover, it is preferable to use a hydrophilic surfactant that is highly soluble in water (for example, a surfactant with HLB in a range of 1 to 18, especially preferably in a range of 8 to 15).

(Surfactant)

The surfactant for use in the present invention is not limited to a particular kind. For example, the surfactant may be an anionic surfactant, a non-anionic surfactant, a cationic surfactant, an ampholytic surfactant, a fluorochemical surfactant, an organic metal surfactant or the like. More specifically, the surfactant may be one described in Patent Literature 28 (PCT international publication No. 97/017397 A), or Patent Literature 30 (U.S. Pat. No. 6,107,358 B).

The amount of the surfactant to use is typically more than 0 but 2 wt % or less, preferably 0.03 wt % or less. more preferably more than 0 but not more than 0.015 wt %, further preferably more than 0 but not more than 0.01 wt %, and most preferably more than 0 but not more than 0.008 wt %, while the amount of the surfactant to use may be varied in consideration of the type of the surfactant to use and the desired properties (especially water absorbing rate and the surface tension). The amount of the surfactant can be applied to the water-absorbable resin powder. Further, if necessary, the amount of the surfactant can be applied to the water-absorbable resin powder covered with the surfactant so as to be a final product as described in "(2-7) surface covering step" later.

If the amount of the surfactant was too much, there would be a risk of having a difficulty in controlling the foaming. Moreover, if so, the resultant water-absorbable resin powder would have an excessively low surface tension, thereby resulting in grater rewetting. Therefore, an excessive amount of the surfactant is not preferable in actually applying the water-absorbable resin powder to disposable diapers. On the other hand, if the amount of the surfactant was very small, the resultant water-absorbable resin powder would be improved in transportability an anti-damaging property, thereby consequently improving the properties of the water-absorbable resin powder after the crosslinking or power transportation. Therefore, the surfactant is used in an amount preferably more than 0 ppm, more preferably, 0.1 ppm or more, and further preferably 1 ppm or more.

In the present invention, the surfactant to be used is not limited to particular one and may be one exemplified in Patent Literature 28 or 30. Various kinds of non-ionic surfactants, negative ion surfactants, cationic surfactants, and ampholytic surfactants may be used as the surfactant in the present invention. The surfactants usable in the present invention may have a group polymerizable or reactive with the monomer(s) of the water-absorbable resin powder.

Typical examples of the nonionic surfactant encompass polyoxy alkylene alkyl ethers, such as polyoxyethylene lauryl ether, polyoxyethylene cetyl ether, polyoxyethylene stearylether, and polyoxyethylene oleyl ether; polyoxyalkylene alkyl phenyl ether, such as polyoxyethylene octylphenyl ether, and polyoxyethylene nonylphenyl ether; polyoxyalkylene alkyl aminoethers, such as polyoxyethylene lauryl aminoether, and polyoxyethylene stearylaminoether; sorbitan fatty acid esters, such as sorbitan monolaurate, sorbitan monopalmitate, sorbitan monostearate, and sorbitan monooleate; polyoxy alkylene sorbitan fatty acid esters, such as polyoxyethylene sorbitan monolaurate, polyoxyethylene sorbitan mono-palmitate, polyoxyethylene sorbitan monostearate, and polyoxyethylene sorbitan monooleate; polyalkylene glycol fatty esters, such as polyethylene glycol monolaurate, polyethylene glycol monooleate, polyethylene glycol monostearate, polyethylene glycol dilaurate, and polyethylene glycol distearate; glycerine fatty acid esters, such as monolauric-acid glyceride, monostearate glyceride, and monooleate glyceride; and the like.

Typical examples of negative ionic surfactant encompass sulfuric ester salts, such as sodium polyoxyethylene lauryl ether sulfate, sodium polyoxyethylene octylphenyl ether sulfate, sodium polyoxyethylene nonylphenyl ether sulfate, lauryl sulfate triethanolamine, sodium lauryl sulfate, potassium lauryl sulfate, ammonium lauryl sulfate; sulfonates, such as sodium dodecylbenzenesulfonate, sodium alkyl naphthalenesulfonate, and sodium dialkyl sulfosuccinate; phosphoric acid ester salt, such as alkyl potassium phosphate; and the like.

Typical examples of positive ionic surfactant encompass quarternary ammonium salts, such as lauryl trimethyl ammonium chloride, stearyl trimethyl ammonium chloride, cetyltrimethyl ammonium chloride, and stearyl trimethyl ammonium chloride; and the like.

Furthermore, as a silicone-type surfactant, anion type, non-ionic type, and cationic silicone type surface active agents are exemplified. Furthermore, polyoxy alkylene modified silicone type surfactants are exemplified. More specifically, polyoxyethylene modified dimethylpolysiloxane, dimethyl polysiloxane modified with a block or random copolymer of polyoxyethylene and polyoxypropylene, dimethylpolysiloxane modified with polyoxyethylene having a C1-C12 alkyl group at its end, dimethylpolysiloxane modified with a block or random copolymer of polyoxyethylene and polyoxypropylene having a C1-C12 alkyl group at their ends, polyoxy alkylene-modified dimethylpolysiloxane derivative having an amino group, an epoxy group, etc. at the end or in the molecule of the dimethylpolysiloxane. Preferable are dimethylpolysiloxane modified with polyoxyethylene, and dimethylpolysiloxane modified with a block or random copolymer of polyoxyethylene and polyoxypropylene. Further preferable is dimethylpolysiloxane modified with polyoxyethylene because it can be available at low cost industrially.

These surfactants may be used solely or two or more of them may be used in combination. The surfactants may be used in combination with the dispersing agent (especially polymer dispersing agent). Among these surfactants, for the sake of effect, it is preferable to use an anionic surfactant, a non-ionic surfactant or a silicone surfactant, and is further preferable to use a non-ionic surfactant or a silicone surfactant.

(Dispersing Agent)

In the production process according to the present invention, it is preferable that the pre-polymerization partly- or fully-prepared acrylic acid-based monomer aqueous solution contains a dispersing agent. The dispersing agent is preferably a hydrophilic polymer dispersing agent that is water absorbable. Further preferably the dispersing agent is a polymer dispersing agent that is water-soluble. A weight average molecular weight of the dispersing agent is determined as appropriate depending on the type of the dispersing agent. The weight average molecular weight of the dispersing agent is preferably in a range of 500 to 10,000,000, further preferably in a range of 5,000 to 5,000,000, and especially preferably in a range of 10,000 to 3,000,000, approximately.

The dispersing agent is not limited to a particular kind specifically. For example, hydrophilic polymers such as starch, a starch derivative, cellulose, cellulose derivative, polyvinyl alcohol, carboxymethyl cellulose (sodium), hydroxyethyl cellulose, and polyacrylic acid (salt), crosslinked polyacrylic acid (salt) can be exemplified. Among then, a water soluble polymer dispersing agent selected from starch, cellulose, and PVA is desirable for the sake of the effect of the present invention.

An amount of the dispersing agent is preferably more than 0 part by weight but not more than 50 parts by weight, more preferably in a range of 0.01 parts by weight to 20 parts by weight, further preferably in a range of 0.05 parts by weight to 10 parts by weight, and most preferably in a range of 0.1 parts by weight to 5 parts by weight, with respect to 100 parts by weight of the monomer content.

The amount of the dispersing agent is specified as such taking into consideration the water-absorbable resin powder serving a hydrophilic polymer dispersing agent, wherein the water-absorbable resin powder is used in replacement of a water soluble polymer. If the amount of the dispersing agent was excessively large, there would be a risk of having a difficulty in controlling the foaming. Moreover, if so, the resultant water-absorbable resin powder would become poor in absorbing ability etc. Therefore, an excessive amount of the dispersing agent is not preferable in actually applying the water-absorbable resin powder to disposable diapers.

(2-1-7) Polymerization Inhibitor

In the production process according to the present invention, a polymerization inhibitor is contained in polymerization, preferably. Examples of the polymerization inhibitor encompass N-oxyxyl compounds, manganese compounds, substituted phenol compounds, exemplified in PCT international application No. 2008/096713. The substituted phenol compounds are preferable, and especially, methoxy phenols are preferably.

Specific examples of methoxy phenols usable herein encompass o, m, p-methoxy phenol, and methoxy phenols substituted with one or plural substituents such as methyl group, t-buthyl group, hydroxyl group. In the present invention, p-methoxy phenol is especially preferable. Methoxy phenol content is in a range of 10 ppm to 200 ppm, preferably in a range of 5 ppm to 160 ppm, preferably in a range of 10 ppm to 160 ppm, further preferably in a range of 10 ppm to 100 ppm, especially preferably in a range of 10 ppm to 80 ppm, and most preferably in a range of 10 ppm to 70 ppm.

If p-methoxy phenol content exceeded 200 ppm, coloring (yellowing, yellow color change) of the resultant water-absorbable resin powder would occur. If p-methoxy phenol content was less than 10 ppm, especially less than 5 ppm, that is, if p-methoxy phenol serving as the polymerization inhibitor was removed due to refining such as distillation or the like, there would be a risk that the polymerization unintentionally takes place before the polymerization is intentionally started. Further, the resultant water-absorbable resin powder would become poorer in antiweatherability (later described). That is, in order to further attain the object (especially, coloring prevention, achieving antiweatherability as an anti damaging property) of the present invention, it is preferable that the monomer aqueous solution contains p-methoxy phenol content by 10 to 200 ppm. It is further preferable that the monomer aqueous solution contains p-methoxy phenol content in the aforementioned range.

(2-1-8) Conventional Foaming Polymerization

In the first to third methods according to the present invention, bubbles are generated in the acrylic acid-based monomer aqueous solution by lowering the solubility of the gas, more specifically, by heating, or adding the water soluble organic material so as to lower the solubility of the gas. The present invention, however, does not require a costly raw material (foaming agent, a large amount of surfactant) or a special device, compared with Patent Literatures 18 to 35, etc. Moreover, as described in "[3] the properties of the water-absorbable polyacrylic acid resin powder" later, the water-absorbable resin powder obtainable by the present invention is has no excessive deterioration in bulk specific gravity or apparent density, unlike the commercially-available water-absorbable resin (whose production method is not disclosed and thus unknown) disclosed in Table 5.6 in Non-Patent Literature 1.

Further, in the present invention, the system (which does not particularly limit the present invention) produces very fine bubbles. By further stabilizing the fine bubbles with the surfactant and/or dispersing agent, it is possible to provide white water-absorbable resin powder with a high water absorbing rate and further with an excellent permeability potential. On the other hand, simple degassing (deoxidation) in a monomer aqueous solution by using inert gas as described in Patent Literature 1 or 3 cannot stability the bubbles during the polymerization, thereby being unable to achieve the object of the present invention.

Note that, in the present invention, meaning of the words "lowering the solubility of the gas" indicates lowering solubility of that gas, and is a concept different from degassing to remove the dissolved oxygen (replacing oxygen with inert gas). The present invention provides a utterly novel foaming method in which heating of the aqueous solution or addition of poor solvent (preferably acrylic acid) to the aqueous solution is performed in the presence of the surfactant and/or dispersing agent, so as to lower the solubility of the dissolved gas, thereby generating bubbles in the aqueous solution and causing the aqueous solution to contain the bubble.

Needless to say, in order to facilitate the polymerization, the present invention may be arranged such that degassing (exchanging the dissolved oxygen with inert gas) is carried out in polymerization, as illustrated in FIGS. 5 to 9. In this case, the dissolved oxygen is decreased preferably to 1 ppm or less, and more preferably to 0.5 ppm or less. Moreover, the step of introducing gas as described in "(2-1-3) gas" above may be additionally provided.

In case where a monomer slurry (aqueous dispersion of acrylate) is polymerized as in Patent Literature 35 (Japanese Patent Application Publication, Tokukaihei, No. 1-318021 A), there is a risk that the resultant properties (water absorbing rate, water soluble content, residual monomer, etc.) would be deteriorated. Therefore, it is preferable that if the monomer(s) is an acid group-containing monomer(s), its neutralization rate is not to an extend that a neutralization salt is precipitated out in the monomer aqueous solution. That is, what is preferably polymerized in the present invention is not an aqueous dispersion of the acrylic acid-based monomer, but the acrylic acid-based monomer aqueous solution. Because solubility of the neutralization salt to water is varied depending on monomer content, neutralization rate, temperature, pressure, and neutralization base, and the dispersing agent (surfactant, another monomer, water soluble polymer) used as needed, the precipitation of the neutralization is designed as appropriate and dependent on these conditions.

(2-2) Defoaming Step

In the present invention, the step of defoaming is preferably provided. By having the step of defoaming, large bubbles are removed from the monomer(s), thereby preventing excessive foaming or deterioration in bulk specific gravity. The defoaming time is preferably 5 seconds or longer, more preferably in 10 second to 60 minutes, further preferably in 30 seconds to 30 minutes, and especially preferably in 60 seconds to 20 minutes. The defoaming is adjusted to remain the desired fine bubbles in the monomer aqueous solution.

The size of the bubbles in the monomer aqueous solution after the step of defoaming is, in volume average diameter, preferably 100 μm or less, more preferably 50 μm or less, further preferably 20 μm or less, or especially preferably 5 μm or less. Moreover, an expansion ratio of the monomer aqueous solution after the step of defoaming is preferably 1.1 times or less, more preferably 1.05 or less, further preferably 1.02 or less, especially preferably 1.01 or less, and its lower limit is normally more than 1, with respect to the monomer aqueous solution before the step of bubbling.

The step of defoaming according to the present invention may be carried out by a well-known technique, such as a method described in U.S. Pat. No. 6,667,372, the specification, a method described in "Foaming engineering, 1st edition" pages 759 to 774, published by Technosystem Co. Ltd.

The step of defoaming is preferably carried out by circulating, into a circulating tank, the monomer aqueous solution containing a circulating gas flow. In the step of defoaming, a headspace of the circulating tank preferably contains oxygen by 1 volume % or more. Moreover, the polymerization is performed after the step of circulating the monomer aqueous solution containing the gas flow, and the step of supplying at least part of the monomer aqueous solution to the step of neutralization, or to the step of polymerizing via the step of neutralization. Moreover, the defoaming may be carried out by holding the monomer aqueous solution in a tube or in the polymerizer for a certain period of time, so that the bubbles are gathered.

More specifically, the polymerization may be carried out in such a way that (i) the monomer aqueous solution containing bubbles therein is introduced into a polymerizing device whose upper part is open, (ii) defoaming is then carried out to mainly eliminate large bubbles, (iii) after a certain period of time, the addition of the polymerization starter or ultraviolet irradiation is carried out to the monomer aqueous solution containing predominantly resultant fine bubbles. If a monomer aqueous solution containing excessively large bubbles is used, the water-absorbable resin powder would have a scale-like shape or excessively low bulk specific gravity (for example, 0.5 [g/cm$^3$] or below). Further, the permeability and the impact resistance would be deteriorated.

Any of these defoaming steps are applicable. However, the purpose of defoaming step in the present invention is to obtain the monomer aqueous solution containing the fine bubbles predominantly, but not to attain complete defoaming. From the resultant water-absorbable resin powder obtained via the step of defoaming as such, porous polymer having fine and uniform pores can be produced.

The micro bubbles (fine bubbles) thus generated via the step of defoaming may be produced by such a phenomenon that condensed ions affect boundaries of the bubbles, thereby causing static electrical charge repulsion, and preventing gas dissipation. The micro bubbles may be crushed into nano bubbles by utilizing auto pressuring effect or adiabatic compression effect, A rising speed and internal pressure of the micro bubbles can be calculated out by Stokes' equation and Laplace's equation (Pb=Pf+2 σ/r), respectively. One exemplary calculation is as follow. When the bubble diameter is 100 μm, the rising speeding is 5400 [μm/s], and the internal pressure is $1.04 \times 10^5$ Pa. Moreover, when the bubble diameter is 10 μm, the rising speeding is 54 [μm/s], and the internal pressure is $1.31 \times 10^5$ Pa. Furthermore, when the bubble diameter is 1 μm, the rising speeding is 0.54 [μm/s], and the internal pressure is $3.95 \times 10^5$ Pa.

An expansion ratio of the volume of the monomer aqueous solution in the step of polymerizing is preferably 1.1 times or less, more preferably 1.05 or less, further preferably 1.02 or less, especially preferably 1.01 or less, and most preferably 1.00 (preferably more than 1), with respect to the volume of the monomer aqueous solution before the step of bubbling. Conventionally, a method for polymerizing after dispersing a large amount of bubbles has been known. In the present invention, the above-described technique is used to perform the polymerization without excessively dispersing the bubbles. Thus, the bulk specific gravity deterioration does not occur substantially in the present invention.

That is, the monomer aqueous solution at the step of polymerization contains micro or nano bubbles having a volume average diameter of 100 μm or less. The micro or nano bubbles contained in the monomer aqueous solution have a volume average diameter of preferably 100 μm or less, more preferably 50 μm or less, further preferably 20 μm or less, and especially preferably 5 μm or less.

The size of the bubbles may be measured by (a) laser differential scattering method (also known as static light scattering method), (b) dynamic light scattering method, (c) electric detection band method (Coulter-counter method), (d) particle counter method (light scattering method, light shielding technique), (e) visualizing method by camera imaging, (f) interference imaging using laser beam and CCD camera, and (g) the like.

Particles can be counted by (c) the electrical detection band method or (d) the particle counter method. In order to measure the particles in nano order, (b) the dynamic light scattering method or (a) laser differential scattering method (also known as static light scattering method) is selected. Any of these measuring methods can be used, but the light scattering methods, especially, the dynamic light scattering method is preferable.

(2-3) Step of Polymerizing

The polymerization may be carried out under atmospheric pressure, reduced pressure, or increased pressure. More preferably, the polymerization is carried out under the atmospheric pressure (or approximately under the atmospheric pressure±10 mmHg). In order to promote the polymerization and to improve the properties, the step of degassing the dissolved oxygen (for example, the step of exchanging the dissolved oxygen with inert gas) according to the schematic flow diagrams of FIGS. 7 to 11 may be provided if necessary.

(Polymerization Starter)

The polymerization starter for use in the present invention is selected as appropriate, considering how the polymerization is carried out. Any polymerization starter is applicable. For example, a photolytic polymerization starter, a pyrolysis polymerization starter, a redox polymerization starter, and the like can be exemplified.

Examples of the photolysis polymerization starter encompass benzoin derivative, benzyl derivative, acetophenone derivative, benzophenone derivative, azo compound, etc. Moreover, examples of the pyrolysis polymerization starter encompass persulfates (sodium persulfate, potassium persulfate, ammonium peroxodisulfate) and peroxides (hydrogen peroxide, t-butyl peroxide, methyl-ethyl-ketone peroxide), azo compounds (2,2'-azobis(2-amidino propane)dihydrochloride, 2,2'-azobis[2-(2-imidazolines 2-yl)propane]dihydrochloride, etc.) etc. Furthermore, examples of the redox polymerization starter encompass mixtures having persulfate or peroxide together with a reducible compound, such as L-ascorbic acid or sodium hydrogensulfite in combination. Moreover, it is one preferable embodiment to use the using together the above-mentioned photolytic polymerization starter and pyrolysis polymerization starter in combination. It is possible to use an azo-type polymerization starter for generating $N_2$ by pyrolysis, so as to facilitate the foaming.

An amount of the polymerization starter to use is preferably in a range of 0.0001 mol % to 1 mol %, and more preferably in a range of 0.0005 mol % to 0.5 mol %, with respect to the monomer(s). It is not preferable that the amount of the polymerization starter exceeds 1 mol %, because, if so, the polymerization starter would adversely affect a color tone of the water-absorbable resin. Moreover, it is not preferable that the amount of the polymerization starter is less than 0.0001 mol %, because, if so, this would result in an increase in the residual monomer amount.

(Additive Etc.)

For the polymerization, a chain transfer agent (such as hypophosphorous acid (salt)), chelating agent, or the like may be added in the reaction system before or during the polymerization.

(Polymerization Method)

In view of the properties of the water-absorbable resin such as the permeability potential and water absorbing rate thereof, and in order to easily control the polymerization, the polymerization of the monomer aqueous solution in the present invention is carried out normally by aqueous polymerization, preferably by kneader polymerization or belt polymerization, more preferably by continuous aqueous polymerization, further preferably high-concentration continuous aqueous polymerization, and especially preferably high-concentration high-temperature starting continuous aqueous polymerization.

The polymerization methods can be preferably adopted in a huge-scale manufacturing device whose production amount of the water-absorbable resin per line is large, that is, in continuous polymerization and continuous production (from the step of drying to the step of surface crosslinking). The production amount is preferably 0.5 [t/hr], more preferably 1 [t/hr], further preferably 5 [t/hr], and especially preferably 10 [t/hr].

As some preferably configurations of the aqueous polymerization, continuous belt polymerizations (disclosed in U.S. Pat. Nos. 4,893,999 B and 6,241,928 B, US patent application publication No. 2005/215734 A, etc.), continuous kneader polymerizations, batch kneader polymerization (U.S. Pat. Nos. 6,987,151 and 6,710,141, etc.) can be exemplified. These aqueous polymerizations can produce the water-absorbable resin with high productivity.

Some preferable examples of the aqueous polymerization encompass high-temperature starting continuous aqueous polymerization, high-concentration continuous aqueous polymerization, and high-concentration high-temperature starting continuous aqueous polymerization. The high-temperature starting continuous aqueous polymerization is such that a polymerization starting temperature is 0° C. or higher, preferably 30° C. or higher, more preferably 35° C. or higher, further preferably 40° C. or higher, especially preferably 50° C. or higher (upper limit is boiling point). The high-concentration continuous aqueous polymerization is such that a monomer concentration is 35 wt % or more, more preferably 40 wt % or more, further preferably 45 wt % or more (upper limit is saturation concentration). The high-concentration high-temperature starting continuous aqueous polymerization is the combination of the high-temperature starting continuous aqueous polymerization and high-concentration continuous aqueous polymerization. Even in case of such a polymerization with high concentration or high temperature, the present invention is excellent in monomer stability and can attain water-absorbable resin with a high degree of whiteness. Thus, the effect of the present invention is more remarkable in case where the polymerization is performed with such conditions. Such high-temperature starting polymerization is exemplified in U.S. Pat. Nos. 6,906,159 and 7,091,253, etc. The production process according to the present invention is excellent in the pre-polymerization monomer stability as well. Thus, the production process according to the present invention can be easily applied to industrial-scale production.

Moreover, the polymerization is preferably configured such that polymerization starting time (a time period between the addition of the polymerization starter and the start of polymerization) is more than 0 second but not more than 300 seconds, and more preferably in a range of 1 second to 240 seconds in order to alleviate reduction of the bubbles in the monomer aqueous solution. If the polymerization starting time exceeded 300 seconds, the number of bubbles introduced in the water-absorbable resin powder is reduced, thereby leading to a risk that the effect of the present invention would not be attained.

(Especially Preferable Foaming Polymerization Conditions)

A wide variety of polymerization methods are applicable, such as spraying polymerization, droplet polymerization, aqueous polymerization, reverse-phase suspension polymerization, and the like. In order to attain the object, aqueous polymerization, especially, continuous belt polymerization or continuous kneader polymerization are preferable, for example.

Moreover, the aqueous polymerization is preferably carried out at the following temperature and with the following concentration. For facilitating the foaming, the polymerization is preferably started at a high temperature. More specifically, the polymerization starting temperature in the step of polymerization is preferably 40° C. or higher, more preferably 50° C. or higher, further preferably 60° C. or higher, especially preferably 70° C. or higher, and most preferably 80° C. or higher. Moreover, for facilitating the foaming, a maximum reaching temperature in the polymerization is preferably high. More specifically, the maximum reaching temperature in the polymerization is preferably 100° C. or higher, more preferably in a range of 100° C. and 130° C., and further preferably in a range of 105° C. and 120° C.

The concentration of the monomer aqueous solution in the polymerization is not particularly limited, but is preferably in a range of 20 wt % and the saturated concentration, more preferably in a range of 25 wt % and 80 wt %, and further preferably in a range of 30 wt % and 70 wt %. It is not preferable that the monomer concentration in the polymerization is less than 20 wt %, because, if so, the productivity would low. As described above, polymerization with a monomer slurry (aqueous dispersion of acrylate) as in Patent Literature 35 (Japanese Patent Literature, Tokukaihei, No. 1-318021 A) would result in polymers with poor properties. Thus, the polymerization is preferably carried out with a monomer concentration not more than the saturated concentration.

Moreover, for facilitating the foaming, a higher concentration of acrylic acid-based monomer aqueous solution in the step of polymerization is more preferable. More specifically, the concentration of acrylic acid-based monomer aqueous solution in the step of polymerization is preferably 40 wt % or higher, more preferably 45 wt % or higher, further preferably 50 wt % or higher (upper limit is normally 90 wt % or less, preferably 80 wt % or less, further preferably 70 wt % or less). Such solid content is applied to the hydrogel crosslinked polymer after the polymerization. The polymerization with the monomer concentration 40 wt % or greater, further with 45 wt % or greater can make the fine bubbles more stable, thereby being especially advantageous for the present invention.

(2-4) Step of Finely Grinding the Gel

In the present invention, the gel is finely grinding (or ground) during or after the polymerization. The foamed gel is ground, especially by mixing and kneading, in order to attain both of the water absorbing rate and the permeability potential, and further improve the impact resistance. That is, in order to attain the object, it is preferable to adopt the aqueous polymerization, especially the belt polymerization or kneader polymerization during or after which the gel grinding is carried out, rather than the reverse-phase suspension polymerization in which the gel grinding is not necessary (the gel grinding is carried out during the polymerization especially in the case of the kneader polymerization, and the gel grinding is carried out after the polymerization especially in the case of the belt polymerization, and in some cases of the kneader polymerization where necessary).

Any kinds of gel grinding devices are applicable to the present invention, for example, batch-type or continuous gel grinder having a plurality of rotational stirring blades such as double-armed kneader, a single- or twin-screwed extruders, meat chopper, etc. can be adopted. Among them, a screwed extruder having a porous die at an end is preferable. For example, a screwed extruder disclosed in Japanese Patent Application Publication, Tokukai, No. 2000-63527 A can be adopted.

Gel particle diameter after the fine pulverization is preferably in a range of 0.5 mm to 3 mm, more preferably in a range of 0.6 mm to 2 mm, and further preferably in a range of 0.8 mm to 1.5 mm by weight average particle diameter (defined by sieve classification). Moreover, content of coarse gel particles of 5 mm or greater in particle diameter is preferably 10 wt % or less, more preferably 5 wt % or less, further preferably 1 wt % or less.

For the sake of particle diameter control and properties, temperature (gel temperature) of the hydrogel before the gel grinding is preferably in a range of 60° C. to 120° C., and more preferably in a range of 65° C. to 110° C. A gel temperature lower than 60° C. results in a greater hardness of the resultant hydrogel, thereby making it difficult to control the particle shape and particle diameter distribution in grinding. Moreover, a gel temperature higher than 120° C. results in a greater softness of the resultant hydrogel on the contrary, thereby making it difficult to control the particle shape and particle diameter distribution.

The gel temperature can be controlled appropriately by the polymerization temperature, post-polymerization heating or cooling, etc. That is, in the present invention, it is preferable that the step of polymerization is carried out by continuous kneader polymerization and the hydrogel crosslinked polymer is finely ground during the polymerization. Moreover, in the present invention, it is preferable that the step of polymerization is carried out by continuous belt polymerization and the hydrogel crosslinked polymer is finely ground after the polymerization.

More preferably, gel grinding described in the Japanese Patent Application, Tokugan, No. 2010-088993 A (filed on Apr. 7, 2010), (especially gel grinding with gel grinding energy (GGE) of 18 to 60 [J/g]) and/or gel grinding described in the same application wherein water soluble content in the hydrogel crosslinked polymer is increased in weight average molecular weight by 10,000 to 500,000 [Da]. In the present invention, an upper limit of the gel grinding energy (GGE) for grinding the hydrogel is preferably 60 [J/g] or less, more preferably 50 [J/g] or less, and further preferably 40 [J/g] or less. A lower limit of GGE is preferably 18 [J/g] or more, more preferably 20 [J/g] or more, and more preferably 25 [J/g] or more. The gel grinding method, and method of increasing the weight average molecular weight of the water soluble content in the hydrogel crosslinked polymer described in the Japanese Patent Application, Tokugan, No. 2010-088993 and its family application claiming priority thereon (including foreign application) are incorporated herein by reference.

Here, the "gel grinding energy" in the Japanese Patent Application, Tokugan, No. 2010-088993 is energy per weight, necessary for the gel grinding device for grinding the hydrogel crosslinked polymer. Hereinafter, the gel grinding energy is abbreviated as GGE, which stands for gel grinding energy. GGE is calculated by the following equation 1 in case the gel grinding device is driven by three-phase AC power.

$$GGE[J/g] = (\sqrt{3} \times voltage \times current \times phase\ factor \times motor\ efficiency)/(weight\ of\ hydrogel\ crosslinked\ polymer\ introduced\ in\ gel\ grinding\ device\ per\ second)$$ [Equation 1]

where the unit of the voltage is [V], the unit of the current is [A], the weight of the hydrogel crosslinked polymer introduced in gel grinding device per second is [g/s]. Moreover, the "phase factor" and "motor efficiency" are variables changed according to condition under which the device is operated and which are intrinsic to the device. The phase factor and the motor efficiency are in a range of 0 to 1. These values can be known by making inquiries to a manufacturer of the device, etc.

GGE in driving the gel grinding device by single phase AC power can be calculated from Equation 1 wherein $\sqrt{3}$ is replaced with "1". How to control the gel grinding energy is described in Paragraphs [0172] to [0173] etc. of Japanese Patent Application, Tokugan, No. 2010-088993. The methods described in Japanese Patent Application, Tokugan, No. 2010-088993 are preferably applicable, wherein, for example, the screwed extruder having a porous die at its end is used, the temperature of the hydrogel crosslinked polymer before the gel grinding is in a range of 60° C. and 120° C., the absorbency without pressure (CRC) of the hydrogel crosslinked polymer before the gel grinding is in a range of 10 to 32 [g/g], the temperature of the hydrogel crosslinked polymer before the gel grinding is in a range of 60° C. and 120° C., etc.

Moreover, as described Paragraphs [0175] to [0176] in Japanese Patent Application, Tokugan, No. 2010-088993 A, the increase in the amount of the water soluble content in the hydrogel crosslinked polymer after the gel grinding is preferably 5 wt % or less, more preferably 4 wt % or less, and further preferably 3 wt % or less, as one way to control GGE within 18 to 60 [J/g].

(2-5) Thermal Heating Step

The hydrogel crosslinked polymer thus obtained is ground during the polymerization or after the polymerization. The pulverization during the polymerization is carried out by using a kneader or reverse-phase suspension polymerization. The pulverization after the polymerization is carried out by meat chopper or the like.

If the hydrogel is not ground, there is a risk that the water-absorbable resin powder targeted by the present invention cannot be obtained. Thus, the hydrogel is ground during or after the polymerization. The ground hydrogel is subjected to the step of drying, and then preferably to the step of surface crosslinking. If water-absorbable resin in a sheet form as in Patent Literatures 19 and 22 cannot attain the object of the present invention. Thus, in the present invention, the pulverization is carried out before or after the drying so as to obtain water-absorbable resin in the powder form.

The hydrogel crosslinked polymer is dried to be dried polymer. The dried polymer in the powder form is dried to a resin solid content of preferably 80 wt % or greater, more preferably in a range of 85 wt % to 99 wt %, further preferably in a range of 90 wt % to 98 wt %, especially preferably in a range of 92 wt % to 97 wt %, where the resin solid content is obtained from weight reduction by drying (heating 1 g of powder or particles at 180° C. for 3 hours). Drying temperature is not particularly limited, but is preferably in a range of 100° C. to 300° C., more preferably in a range of 150° C. to 250° C. Coagulated powder or particles may be resulted from the step of drying. The coagulated powder or particles as such may be supplied to the step of crushing. In the present invention, the hydrogel containing the bubbles (especially, closed bubbles) is obtained in the step of polymerizing, and the hydrogel containing the bubbles is preferable because the foaming further proceeds during high-temperature drying. Drying temperature and drying devices are set as appropriate. For example, the drying is carried out, for example, preferably for 1 minute to 5 hours, more preferably for 5 minute to 1 hour. Through-flow band drying, stirring drying, drying by azeotropic dehydration may be used solely or two or more of them may be used in combination.

(Particle Diameter)

In order to attain the object of the present invention, and for the sake of the water absorbing rate, permeability potential, and absorbency against pressure, the weight average particle diameter (D50) of the water-absorbable resin powder before the surface crosslinking is preferably in a range of 200 μm to 600 μm, more preferably in a range of 200 μm to 550 μm, further preferably in a range of 250 μm to 500 μm, and especially preferably in a range of 350 μm to 450 μm. Moreover, for the sake of the permeability potential, etc., it is preferable that the content of particles of less than 150 μm according to JIS standard sieve is less. The content of particles of less than 150 μm according to JIS standard sieve is adjusted normally to be in a range of 0 to 5 wt %, preferably to be in a range of 0 to 3 wt %, especially to be in a range of 0 to 1 wt %. The particle diameter control may be carried out by crushing, classifying, etc. during the polymerization or after the gel grinding or drying. It is especially preferable that the particle diameter control is carried out in classifying after the drying.

Figure 3:
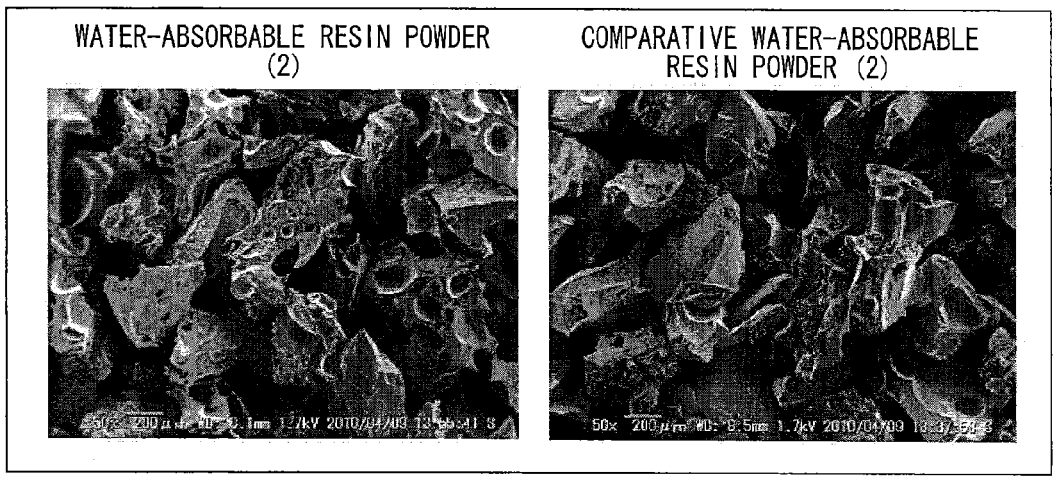
FIG. 3 is an electronic microscopic photograph (×50) of water-absorbable resin powder obtained in Example 2 and Comparative Example 2. Moreover, in Examples and Comparative Examples later described, a grinding step is employed after polymerization and drying. Thus, the water-absorbable resin powder had an irregular broken shape as shown in the picture.
Figure 12:
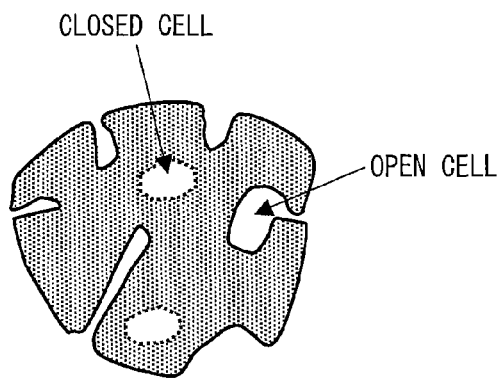
FIG. 12 is a cross sectional view schematically illustrating closed cells and open cells in the water-absorbable resin powder. The water-absorbable resin (later described) in the present invention is characterized in its inner bubble fraction (also known as closed cells) controlled within a particular range.
Figure 13:
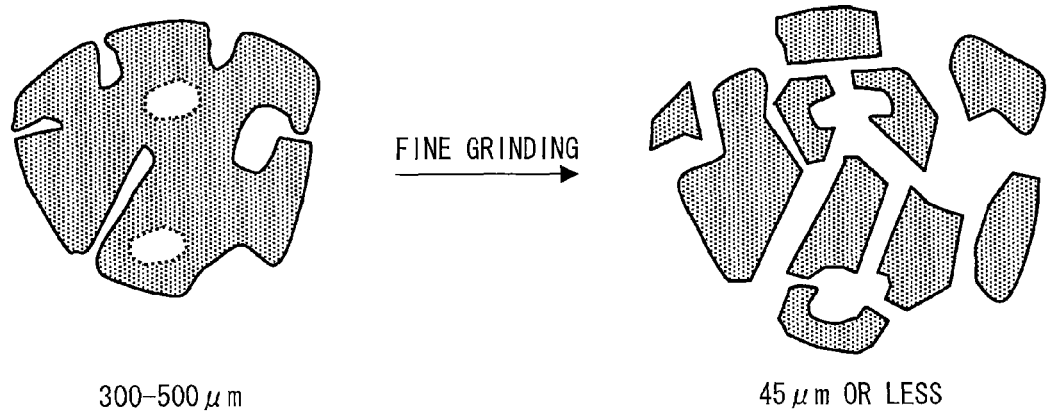
FIG. 13 is a cross sectional view schematically illustrating how to finely grind to less than 45 μm the water-absorbable resin powder (for example, contain particles in particle diameter of 850 to 150 μm by 95 wt %) in order to perform the real density measurement in the present invention. By finely grinding the water-absorbable resin powder, the closed cells are broken or converted into open cells substantially. Then, dry density measurement is carried out with helium gas. Thereby, real density (g/cm$^3$) of the water-absorbable resin powder can be measured.

The shape of the water-absorbable resin powder may be spherical, coagulation of the particles, or in irregular broken shapes obtained via the step of crushing the polymerized gel or the dried polymer (for example, as illustrated in FIGS. 3, 12, and 13). However, for the sake of the water absorbing rate, it is preferable that the shape of the water-absorbable resin powder is in the in irregular broken shapes or in a particle shape ground from the irregular broken shapes.

Further, for the sake of the water absorbing rate, etc., it is preferable that content of particles passing the JIS standard sieve of 850 μm or greater (further, 710 μm or greater) in mesh size is less. The content of particles of 850 μm or greater (further, 710 μm or greater) is adjusted to be normally in a range of 0 to 5 wt %, preferably in a range of 0 to 3 wt %, especially preferably in a range of 0 to 1 wt %. Moreover, in order to further attain the object of the present invention, for the sake of the water absorbing rate, permeability potential, and absorbency under pressure, the present invention is arranged such that the surface crosslinking is carried out with powder in which a ratio of particles of 850 μm (passing the sieve) to 150 μm, preferably of 710 μm (passing the sieve) to 150 μm is 95 wt % or greater, further preferably 98 wt % or greater, and especially preferably 99 wt % or greater (upper limit is 100 wt %).

The particle diameter is carried out by using standard sieves, for example, as described in the pamphlet of PCT international publication No. 2004/69915, or in EDANA-ERT420.2-02. In order to further attain the object of the present invention, the particle diameter before the surface crosslinking is applied preferably to particle diameter after the surface crosslinking, further preferably to the water-absorbable resin particles, which is the final product (or to later-described water-absorbable resin powder of the present invention).

(2-6) Step of Surface Crosslinking

In order to attain better water absorbing rate (or the permeability potential), it is preferably to further include the step of surface crosslinking the water-absorbable polyacrylic acid resin powder after the drying. The surface crosslinking may be carried out with a surface crosslinking agent described later, by polymerizing the monomer(s) on a surface of the water-absorbable resin, or by heating or ultraviolet irradiation in the presence of a radical polymerization starter such as persulfate, UV starter, or the like.

The step of surface crosslinking in the present invention is preferably carried out by using a surface crosslinking agent, further preferably by using a covalent bonding surface crosslinking agent, and especially preferably by using plural kinds of the covalent bonding surface crosslinking agents in combination.

(Crosslinking Agent)

In the present invention, it is preferable to further include the step of surface crosslinking after the drying. In the production process according to the present invention, such a configuration including performing the step of surface crosslinking after the drying is applied to a huge-scale (especially 1 [t/hr]) continuous production for water-absorbable resin powder with high absorbency against pressure (AAP) and high permeability potential (SFC). Especially, it is preferably applied to water-absorbable resin powder obtained via high temperature surface crosslinking.

(Covalent Bonding Surface Crosslinking Agent)

Various organic or inorganic crosslinking agents can be exemplified as the surface crosslinking agent for use in the present invention, but it is preferable that the surface crosslinking agent is an organic surface crosslinking agent.

For the sake of the properties, it is preferable to use a dehydrative crosslinking agent such as a multivalent alcohol compound, an epoxy compound, and a multivalent amine compound, and a condensed product of them with halo epoxy compound, an oxazoline compound, a (mono, di, or poly) oxazolidinone compound, an alkylene carbonate compound. Especially, a dehydrative crosslinking agent such as a multivalent alcohol compound, an alkylene carbonate compound, and oxazolidinone compound, which need high-temperature reaction can be used.

In case where a dehydrative crosslinking agent is not used, more specifically, the compounds described in U.S. Pat. Nos. 6,228,930, 6,071,976, and 6,254,990 etc. can be exemplified. For example, multivalent alcohols, such as mono-, di-, tri-, tetra-propylene glycol, 1,3-propanediol, glycerin, 1,4-butanediol, 1,3-butanediol, 1,5-pentanediol, 1,6-hexanediol and sorbitol; epoxy compounds, such as ethylene glycol diglycidyl ether, and glycidol; alkylene carbonate compounds such as ethylene carbonate; oxetane compounds; cyclic urea compounds, such as 2-imidazolidinone; and the like are exemplified.

(Ionic Bonding Surface Crosslinking Agent or Water Insoluble Fine Particles)

Moreover, a polyamine polymer or a multivalent metal salt is used as an ionic bonding surface crosslinking agent in addition to the organic surface crosslinking agent (for covalent bonding), in order to improve the permeability potential etc. The use of ionic bonding surface crosslinking agent is preferable because it acts as an electrostatic spacer between swollen gel particles, thereby contributing to the improvement in permeability potential. In the present invention, especially in case where the permeability potential, especially SFC is set to 20 [×$10^{-7}$·cm$^3$·sec·g$^{-1}$] or greater, or set to be in the later described range, the permeability potential is preferably improved by using the organic surface crosslinking agent (for covalent bonding surface crosslinking) and the ionic bonding surface crosslinking agent or later-described water insoluble fine particles in combination.

Examples of the multivalent metal salt (inorganic surface crosslinking agent) to be used encompass divalent or greater, preferably trivalent or tetravalent metal salt (organic salt or inorganic salt) or hydroxide, that is, multivalent metal cations. Usable multivalent metals encompass aluminum, zirconium, and the like. Preferable multivalent metal salts are aluminum cations such as aluminum latate, aluminum sulfate, etc.

Examples of the polyamine polymer used herein encompass polyethylene imine, polyvinyl amine, polyallyl amine, etc. A weight average molecular amount of the polyamine polymer is appropriately determined in a range of 1000 to 5,000,000, or in a range of 10,000 to 1,000,000.

Examples of the water insoluble fine particles used herein encompass inorganic fine particles of silicon oxide, aluminum oxide, clay, kaolin, or the like, organic fine particles of aluminum lactate, calcium lactate, metallic soap (multivalent metallic salt of long chain fatty acid), or the like. As for the volume average particle diameter, 10 μm or less are preferable, and its 1 μm or less is more preferable.

That is, it is preferable that the water-absorbable resin powder further contains a permeability potential improving agent in the surface crosslinking, wherein the permeability potential improving agent is selected from among the multivalent metal cations, polyamine polymers, and water insoluble fine particles exemplified in (2-6) above. By containing the permeability potential improving agent of such a kind, both the water absorbing rate and the permeability potential can be attained at high levels. Further, by containing the permeability potential improving agent of such a kind, the water-absorbable resin powder shows excellent anti-caking property when the water-absorbable resin powder is wet. Thus, the configuration in which the water-absorbable resin powder further contains the permeability potential improving agent can be preferably applied to foamed water-absorbable resin which easily uptakes moist.

(Solvent)

An amount of the organic surface crosslinking agent (covalent bonding surface crosslinking agent) to use is determined as appropriate, preferably in arrange of 0.001 parts by weight to 10 parts by weight, and more preferably in arrange of 0.01 parts by weight to 5 parts by weight with respect to 100 parts by weight of the water-absorbable resin powder. The permeability potential improving agent selected from the multivalent metal cation, the polyamine polymers, and the water insoluble fine particles is preferably in a range of 0 part by weight to 5 parts by weight, more preferably in a range of 0.001 parts by weight to 3 parts by weight, further preferably in a range of 0.01 parts by weight to 2 parts by weight, and especially more preferably in a range of 0.05 parts by weight to 1 part by weight.

In addition to the surface crosslinking agent, water is used in combination preferably. An amount of the water used herein is preferably in a range of 0.5 parts by weight to 20 parts by weight, and more preferably in a range of 0.5 parts by weight to 10 parts by weight with respect to 100 parts by weight of the water-absorbable resin powder.

In case where an inorganic surface crosslinking agent and an organic surface crosslinking agents are used in combination, the surface crosslinking agents are respectively used in an amount in a range of 0.001 to 10 parts by weight, more preferably in a range of 0.01 parts by weight to 5 parts by weight with respect to 100 parts by weight of water-absorbable resin powder. In this case, a hydrophilic organic solvent may be used in an amount preferably more than 0 part by weight but not more than 10 parts by weight, more preferably more than 0 part by weight but not more than 5 parts by weight, with respect to 100 parts by weight of the water-absorbable resin powder.

In adding the crosslinking agent to the water-absorbable resin powder, water insoluble fine particle powder or a surfactant may be added as well in an amount not adversely affecting the effect of the present invention, for example, more than 0 part by weight but not more than 10 parts by weight, preferably more than 0 part by weight but not more than 5 parts by weight, and more preferably more than 0 part by weight but not more than 1 part by weight. Examples of usable surfactants and an amount of the surfactant to use are exemplified in U.S. Pat. No. 7,473,739 B.

The water-absorbable resin powder to which the surface crosslinking agent has been added is subjected to heating treatment. Then, if necessary, the water-absorbable resin powder is cooled. The heating is carried out a temperature preferably in a range of 70° C. to 300° C., more preferably in a range of 120° C. to 250° C., further preferably in a range of 150° C. to 250° C., for a heating period of preferably 1 minute to 2 hours.

By using the surface crosslinking, especially the surface crosslinking after particle diameter controlling, the absorbency against pressure (AAP) later described is improved preferable to be 20 [g/g] or greater, further preferably to be in a range of 23 to 30 [g/g]. Especially, in case where SFC is improved to be within the following range (for example, 20 [×10$^{-7}$·cm$^3$·sec·g$^{-1}$] or greater, further preferably within the later described range), the surface crosslinking is performed to the attain CRC in the above range, preferably in a range of 15 [g/g] to 45 [g/g], more preferably in a range of 20 [g/g] to 40 [g/g], further preferably in a range of 25 [g/g] to 35 [g/g], especially preferably in a range of 28 [g/g] to 33 [g/g]. Further preferably, a permeability potential improving agent selected from the multivalent metal cations, polyamine polymers, and water insoluble fine particles is contained, whereby the permeability potential can be further improved.

(2-7) Step of Surface Coating

This step is a step of coating the surface of the water-absorbable resin powder with a/the surfactant in order to attain water-absorbable resin powder with high water absorbing rate and high permeability potential.

The water-absorbable resin powder of the present invention is a foamed product and tends to weak in impact resistance as powder. Especially, there is a risk that the properties are deteriorated by damages during or after the surface crosslinking. Production larger in scale (production amount per time) shows such a tendency more remarkably. For example, the tendency is more remarkable when the production amount is preferably 0.5 [t/hr] or more per line. The tendency is more remarkable when the production amount is 1 [t/hr] or more. The tendency is further remarkable when the production amount is 5 [t/hr] or more. The tendency is further more remarkable when the production amount is 10 [t/hr] or more.

Especially in the case of the huge-scale continuous production, in order to solve this problem and attain water-absorbable resin with high water absorbing rate and high permeability potential, the step of surface crosslinking the water-absorbable resin powder is further provided preferably after the drying, and the step of coating the surface of the water-absorbable resin powder with a surfactant is further provided wherein the step of coating the surface of the water-absorbable resin powder and the step of surface crosslinking the water-absorbable resin powder may be carried out at the same time or separately.

Which kind of the surfactant is used in how much amount is determined as appropriate. The amount of the surfactant is preferably 2 wt % or less, more preferably 0.03 wt % or less, further preferably 0.015 wt % or less, still further preferably 0.01 wt % or less, and yet further preferably 0.008 wt % or less. A lower limit of the amount of the surfactant is 0.1 ppm or more, and more preferably 1 ppm or more. The kind and amount of the surfactant is selected preferably to maintain the surface tension (preferably 60 [mN/m] or more, further preferably within the range described in "(3-7) Surface tension" later). For the sake of the water-absorbing rate or impact resistance, it is preferable that water is also contained in addition with the surfactant. The water is used or contained in the water-absorbable resin in an amount preferably in a range of 0.1 wt % to 10 wt %, further preferably in a range of 1 wt % to 8 wt %, especially preferably in a range of 2 wt % to 7 wt %.

(2-8) Step of Recycling Fine Powder

In order to further attain the object, the process according to the present invention preferably includes the step of classifying after the step of drying, and fine powder separated out in the step of classifying is recycled to be reused in the steps before the drying. That is, after the polymerization, the water-absorbable resin preferably after the step of thermally drying is adjusted in particle diameter by crushing and classifying if necessary. Moreover, coarse particles (for example, of 1 mm or greater) separated out by the classifying may be crushed if necessary. Moreover, fine particles (for example less than 150 μm, further less than 106 μm) separated out by the classifying may be discarded, used for another purposes, or recycled. It was found that the permeability potential (for example, SFC) was improved by removing such fine powder. Further, it was found that the water absorbing rate (for example, FSR) is improved by recycling the fine powder thus removed.

That is, the production process according to the present invention may include the step of recycling the fine powder, preferably. In the step of recycling the fine powder, the fine powder (especially fine powder containing particles of particle diameter of 150 μm or less by 70 wt % or more) produced in the step of drying, and if necessary, the step of crushing and the step of classifying is separated out, then the fine powder as such or being further hydrated and granulated is recycled to be reused in a step before the crushing, preferably in the step of polymerizing, the step of grinding the foamed polymer, or the step of thermally drying. By recycling the fine powder, particle diameter of base polymer can be controlled. Further, the addition of the fine powder further improves the water absorbing rate. The fine powder may be fine powder before or after the surface crosslinking. An amount of the recycled fine powder is preferably in a range of 1 wt % to 40 wt %, and more preferably in a range of 5 wt % to 30 wt % with respect to the dried polymer.

A preferable method for recycling the fine powder in the present invention is arranged such that the fine powder of the water-absorbable resin, which fine powder may be hydrated or granulated, and if necessary, inorganic particles are mixed into the monomer aqueous solution to be polymerized or the hydrogel during the polymerization. The monomer(s) to be polymerized may be increased in viscosity by using the recycled fine powder in order to facilitate the foaming.

Methods for recycling the fine powder into the gel during the polymerization are exemplified in PCT international publications Nos. 2007/074167, 2009/109563, 2009/153196, and 2010/006937. Methods for recycling into the monomer aqueous solution before the polymerization are exemplified in PCT international publications Nos. 92/001008, and 92/020723. Methods for recycling into a dryer are exemplified in U.S. Pat. No. 6,228,930, etc. These fine powder recycling methods can be adopted suitably.

(2-9) Step of Adding Anti-Coloring Agent or Anti-Urine Property Improving Agent

In general, water-absorbable resin with a large surface area is easily colored or deteriorated in properties. Thus, in the present invention, in order to prevent coloring or deterioration, it is preferable to further contain a anti-coloring agent or an anti-urine (antiweatherability) improving agent, selected from the group consisting of a chelating agent (especially, organic phosphor-type chelating agent, amino carboxylic acid chelating agent), α-hydroxy carboxylic acid (especially lactic acid or its salt), inorganic or organic reducing agent (especially, sulfur-type inorganic reducing agent). As to how much they are used, they are used preferably by 0 to 3 parts by weight, more preferably 0.001 to 1 part by weight, and especially preferably 0.05 to 0.5 part by weights, with respect to 100 parts by weight of the water-absorbable resin. They are used by being added in the monomer(s), hydrogel, dried polymer, or powder. An adding step is selected as appropriate, depending on the step of polymerizing and its downstream steps. The reducing agent among them is consumed is the polymerization, thus is added preferably after the polymerization, more preferably after the drying, especially preferably after the surface crosslinking.

As the chelating agent, those exemplified in U.S. Pat. Nos. 6,599,989 and 6,469,080, and EP patent No. 2163302 can be used. Among them, especially, non-polymer chelating agent, furthermore, organic phosphor chelating agent, and amino carboxylic acid chelating agent can be used. As α-hydroxy carboxylic acid, malic acid, succinic acid, lactic acid, and their salt (especially, monovalent salt) mentioned in US Patent Application Publication No. 2009/0312183 can be exemplified. As usable inorganic or organic reducing agents (especially, sulfuring inorganic reducing agents), sulfur-type reducing agent mentioned in US Patent Application Publication No. 2010/0062252, especially, sulfurous acid and hydrogen sulfite can be exemplified.

(2-10) Other Steps

Besides those steps described above, a second step of classifying, a step of recycling evaporated monomer, a step of granulating, a step of removing fine powder, or the like may be provided. Further, an additive may be added to the monomer(s) or the polymer prepared therefrom, in order to attain color stability over time or prevent gel property deterioration, etc.

Furthermore, if required by the purpose thereof, the water-absorbable resin powder may contain an oxidant, anti-oxidant, water, multivalent metal compound, water-insoluble inorganic or organic powder such as silica, metal soap, etc., deodorant, antimicrobial agent, pulps, thermoplastic fiber, or the like in an amount more than 0 wt % but not more than 3 wt %, preferably more than 0 wt % but not more than 1 wt %. It is preferable that the surfactant content in the water-absorbable resin powder is within the aforementioned range.

[3] PROPERTIES OF WATER-ABSORBABLE POLYACRYLIC ACID RESIN POWDER

Novel First Water-Absorbable Resin Powder (See FIGS. 12 and 13)

The water-absorbable resin powder produced by the production process according to the present invention has a predetermined amount of cells inside thereof. The present invention provides novel water-absorbable resin powder having a cell rate (cell rate inside the water-absorbable resin particles; also called porosity) within a particular range.

That is, in order to attain the object, the present invention provides water-absorbable resin powder, which is water-absorbable polyacrylic acid resin powder and which has an internal cell rate (or also called closed cell rate) in a range of 2.8% to 6.6%, wherein the internal cell rate is defined by the following equation.

(Internal cell rate [%])={(real density [g/cm$^3$])−(apparent density [g/cm$^3$])}/(real density [g/cm$^3$])×100

The real density [g/cm$^3$] of the water-absorbable polyacrylic acid resin powder is obtained from water-absorbable resin polyacrylic acid powder sufficiently dried (water content of preferably less than 1 wt %, more preferably less than 0.5 wt %, and especially preferably less than 0.1 wt %), and can be fixedly determined from chemical composition (repeating unit etc. of the polymer, minute raw materials such as the crosslinking agent, and graft component used arbitrarily). Therefore, the real density of the water-absorbable polyacrylic acid resin powder is substantially constant, even though it may vary slightly due to its neutralization rate, the type of the salt of the neutralization (for example, sodium polyacrylate of neutralization rate of 75 mol %), or the minute raw material.

On the contrary to the real density determinable by the chemical composition (mainly, the repeating unit), the "apparent density" of the water-absorbable resin powder is density determined in consideration of the pores (in other words, the cells, especially closed cells) inside the particles. More specifically, the water-absorbable resin thus obtained by the foaming polymerization or the water-absorbable resin having been subjected to the step of granulating has a space (closed pore; void: closed cell) inside, which space is not communicated with its outside, as illustrated in FIG. 12. Thus, when the density of the water-absorbable resin is measured by dry density measurement, the apparent density is obtained from the volume including the closed pore (closed cells) because the introduced gas cannot enter the closed pore.

In this Specification, effective digits for the apparent density and the real density are determined by the measuring devices as appropriate. For example, the effective digits may be three or four digits after the decimal point. More specifically, Example 15 described later discloses an apparent density of 1.588 [g/cm$^3$]. Regarding the apparent density of water-absorbable resin, Non-Patent Literature 1, pages 197 to 199, discloses that water-absorbable resin having been subjected to 40 to 60 mesh-cut is measured by wet measurement in which volume of the water-absorbable resin is measured by use of methanol. The apparent density of the present invention is characterized in being measured by the dry measurement for all particle diameters. The inventors of the present invention found that the internal porosity defined by such apparent density is important for the water-absorbable resin.

The density of water-absorbable resin can be accurately measured by the dry density measurement in which a certain gas is used. The dry density measurement for solid is based on such measurement principle that has been well known in an isovolumetric swelling method in which volume of the solid is measured by use of a certain gas. More specifically, assuming that the volume of cells of a sample, $V_{cell}$, and the volume of the cells expanded, $V_{exp}$, are known, the volume of the sample, $V_{samp}$, can be obtained by measuring pressures (gage pressures) $P_{1g}$ and $P_{2g}$, and the density of the sample can be obtained by dividing the volume of the sample with mass of the sample, which is separately measured. (see the homepage of Shimazu Corporation, http://www.shimadzu.co.jp/powder/lecture/middle/m04.ht ml)

The real density is fixedly determined from the chemical composition (mainly, the repeating unit of the polymer). Thus, a known value may be used as the real density. If there is no known value for the real density of the water-absorbable resin real density because the real density is varied slightly due to the minute raw material of the water-absorbable resin, the real density may be determined by a later-described method.

In the present invention, the real density can be determined by the later-described method (see FIG. 13), in which dry density of water-absorbable resin is measured after the water-absorbable resin is subjected to fine grinding so as to substantially eliminating closed cells in the water-absorbable resin by breaking the closed cells or converting the closed cells into open cells by the fine grinding. Here, the open cells are cells communicating with outside and are not measured into the volume of the powder in measuring the dry density of the power. Thus, the closed cells and the open cells can be easily distinguished from each other by the dry density measurement of powder.

The closed-cell rate of the water-absorbable resin in the present invention is in a range of 2.8% to 6.6%, preferably in a range of 3.0% to 6.5%, further preferably in a range of 3.5% to 6.5%, especially preferably in a range of 3.8% to 6.5%, most preferably in a range of 4.0% to 6.5%, (where the closed-cell rate is defined by measurement method of Example). If the closed-cell rate is less than 2.8%, the improvement on water absorbing rate (FSR) is not large. If the closed-cell rate exceeds 6.6%, the anti-damage property is deteriorated, and the permeability potential (SFC) is also decreased in association with the anti-damage property deterioration. Thus, the closed-cell rate less than 2.8% or exceeding 6.6% is not preferable. The closed-cell rate can be controlled as appropriate by the bubble content in the polymerization or the drying temperature (more swollen by high temperature), etc. in the production process according to the present invention.

Conventionally, the foaming polymerizations of water-absorbable resin for improving the water absorbing rate have been disclosed in Patent Literatures 18 to 35, etc. However, the closed-cell rate is difficult to control in the conventional foaming polymerizations represented by the ones in Patent Literature 31 (U.S. Pat. No. 61,007,358), or in Comparative Example 8 corresponding to Patent Literature 31 in the present application. This results in excessive closed-cell rates exceeding 6.6%, or need of a large amount (for example, 0.1 wt % to 10 wt %) of a surfactant for foaming as described in Patent Literatures 28 and 29. Consequently, the resultant water-absorbable resin powder has poor surface tension (especially, less than 60 [mN/m], further less than 55 [mN/m]), or excessive foaming that generates fine powder (especially, 10 wt % or more).

Moreover, Non-Patent literature 1, pages 197 to 199, and Table 5.6 disclose BET surface areas, water absorbing rates, water absorbencies, bulk specific gravities, and apparent densities of commercially available (polyacrylic acid) water-absorbable resins (5 kinds) having been subjected to 40 to 60 mesh-cut (corresponding to powder in a range of 425 μm to 250 μm).

Non-Patent Literature 1 discloses five (5) commercially available water-absorbable resin with specific apparent densities measured by methanol wet method, namely: 1.500 [g/cm$^3$] for Product Name Arasorb 720 (Arakawa Chemical Industries Ltd.) and Sanwet 1M-1000 (Sanyo Chemical Industries Ltd.); 1.250 [g/cm$^3$] for Aridall 1078 (American Colloid Company), 1.667 [g/cm$^3$] for Aquakeep (Sumitomo Seika Chemicals Co. Ltd.) and Dry Tech 510 (Dow Chemicals Co., Ltd.). That is, Non-Patent Literature 1 discloses five (5) commercially available water-absorbable resin with specific apparent densities in a range of 1.250 to 1.667 [g/cm$^3$].

The apparent density (methanol wet method) having been subjected to 40 to 60 mesh-cut in Non-Patent Literature 1 is different from the dry density measured for the whole particle diameters in the present invention. Further, Non-Patent Literature 1 does not provide the real density nor the chemical composition of each commercially available water-absorbable resins. Assuming that Aquakeep (reverse-phase suspension polymerization, spherical particles) has an apparent density of 1.667 [g/cm$^3$] which is substantially a real density, and all the five (5) commercially available water-absorbable resins listed in Table 5.6 have the same chemical composition, the closed-cell rates of the commercially available water-absorbable resins (Table 5.6) can be divided into a type having closed-cell rates of 0% or close to 0% (Aquakeep, Dry Tech 510) and another type having closed-cell rates approximately in a range of 10% to 25% (Arasorb 720, Sanwet 1M-1000, Aridall 1078). On the other hand, the present invention is characterized in that the closed-cell rate (2.8% to 6.6%) and the particle diameter (the ratio of the particles with particle diameters within 850 μm to 150 μm is 95 wt % or more) are controlled within the particular narrow ranges.

Moreover, Patent Literature 31 (U.S. Pat. No. 5,856,370) does not disclose the particular closed-cell rate and particle diameter of the present invention, while Patent Literature 31 discloses porous water-absorbable resin obtained by using an azo compound so as to attain a density of more than 1.0 [g/cm$^3$] when dry and a density of 1.0 [g/cm$^3$] when swollen (wherein the density when swollen is measured by using a pycnometer).

It was found by the inventor of the present invention that if the closed-cell rate defined in the present invention exceeds 6.6%, the permeability potential (SFC) and the impact resistance are deteriorated as described in Comparative Examples 12 and 14 later described. The present invention is characterized in controlling the closed-cell rate that has not been considered at all in the conventional foaming polymerization.

The water-absorbable resin powder (first water-absorbable resin) according to the present invention is high in impact resistance even if the water-absorbable resin powder is obtained by the foaming polymerization. Thus, the water-absorbable resin powder is low in fine powder content: the ratio of the particles with particle diameters within 850 μm to 150 μm is 95 wt % or more, further preferably the water-absorbable resin powder has the range described in (2-5) above (ranging from 850/710 μm to 150 μm) or the weight average particle diameter (D50). Conventionally, techniques for reducing the particle diameter for improving the water absorbing rate have been known as in Patent Literature 10. Such techniques are associated with an increase in fine powder. The present invention is free from such a problem. See (2-5) above for further preferable particle diameters of the water-absorbable resin powder according to the present invention.

Even if the water-absorbable resin powder (first water-absorbable resin) according to the present invention is obtained by foaming polymerization, but the water-absorbable resin powder according to the present invention does not need a large amount of surfactant (for example, 0.1 wt % to 10 wt %) for foaming, unlike Patent Literatures 28 and 29. Thus, the surface tension in the water-absorbable resin powder according to the present invention is not decreased and is 60 mN/m or more, further preferably within the ranges described in (3-7) described later. The surface tension can be adjusted by type and amount of the surfactant, which are used preferably within the ranges described in (2-1-6) above.

That is, the water-absorbable resin powder, one example of whose production process is a production process according to the present invention (including lowering the solubility of the gas) is water-absorbable polyacrylic acid resin powder such that a ratio of particles having particle diameters in a range of 850 μm to 150 μm is 95 wt % or more, preferably 98 wt % or more, and especially preferably 99 wt % or more, a surface tension is 60 [mN/m] or more, and the closed-cell rate is 2.8% to 6.6%, wherein the closed-cell rate is defined by the following equation:

(Closed-cell rate [%])={(Real density [g/cm$^3$])−(Apparent density [g/cm$^3$])}/(real density [g/cm$^3$])×100

The water-absorbable resin powder according to the present invention is obtained by, for example, a process including the surface crosslinking, especially, the surface crosslinking to attain the CRC within the aforementioned range. Preferably, the water-absorbable resin powder according to the present invention is such that absorbency against pressure (AAP) under load of 50 [g/cm$^2$] is 15 [g/g] or more. The preferable range of AAP has been mentioned above. Disposable diaper with high content of water-absorbable resin with low AAP would not have sufficient water absorbing property.

The water-absorbable resin powder according to the present invention is obtained by, for example, a process including the surface crosslinking, especially, the surface crosslinking to attain the CRC within the aforementioned range. Preferably, the water-absorbable resin powder according to the present invention is such that saline flow conductivity (SFC) is 20 [×10$^{-7}$·cm$^3$·sec·g$^{-1}$] or greater.

The water-absorbable resin powder is preferably configured such that the surface crosslinking is carried out further with a permeability potential improving agent selected from among the multivalent metal cations, polyamine polymers, and water insoluble fine particles exemplified in (2-6). By containing the permeability potential improving agent, the water-absorbable resin powder attains both the water absorbing rate and the permeability potential. Moreover, the water-absorbable resin powder is also improved in anti-caking property at uptaking moist.

The water-absorbable resin powder according to the present invention is preferably configured to further comprise a surfactant by a method exemplified in (2-6) or (2-1-6). By containing the surfactant, the water-absorbable resin powder can be obtained with excellent impact resistance. The amount of the surfactant is preferably within the range described above. It is preferably that the surfactant is added in the form of an aqueous solution.

The water-absorbable resin powder according to the present invention preferably comprises the surfactant within the above range or to the extent that the surface tension is within the range, wherein the surfactant is added at polymerization or before or after the surface crosslinking.

The water-absorbable resin powder according to the present invention may comprise, as described in (2-1-7) above, p-methoxy phenol (MEHQ) preferably by 5 ppm to 60 ppm, more preferably 5 ppm to 40 ppm, further preferably 5 ppm to 30 ppm. Thereby, the water-absorbable resin powder can be excellent in antiweatherability. Coloring would occur in water-absorbable resin powder with an excessive amount of p-methoxy phenyl. But if the amount of p-methoxy phenyl was too small, water-absorbable resin would poor antiweatherability. Non-Patent Literature 1, chapter "2.5.3 Inhibition" (polymerization inhibitor) (pages 39 to 44) discloses in Tables 2.5 that commercially available water-absorbable resins (8 kinds) contain p-methoxy phenol by 16 ppm to 151 ppm. However, Non-Patent Literature 1 does not disclose the effect of the present invention (coloring prevention and light resistance improvement by controlling the p-methoxy phenol content within a particular range).

In the manufacturing steps of the water-absorbable resin (especially, the step of polymerizing and the step of drying), part of p-methoxy phenol is consumed. In view of this, the p-methoxy phenol content may be adjusted in the step of polymerizing or the step of drying, or in the water-absorbable resin as the final product according to the method described for example in PCT/JP2010/067086. More specifically, the step of neutralizing is carried out with a basic material having an iron content of 0 ppm to 7 ppm. The step of polymerizing is carried out by aqueous polymerization or reverse-phase suspension polymerization with a monomer aqueous solution and a radical polymer starter under such conditions that a polymerization maximum temperature is 130° C. or less, and a polymerization time is 0.5 minutes to 3 hours, the monomer aqueous solution containing a monomer(s) by 30 wt % to 55 wt %, wherein the monomer(s) is acrylic acid (salt) by 90 mol % to 100 mol %, the radical polymer starter being in a range of 0.001 mol % to 1 mol %. The step of drying is to dry hydrogel crosslinked polymer in the form of particles thus obtained by the step of polymerizing (including gel fine pulverization step) at a drying temperature in range of 100° C. to 250° C. for a drying time in a range of 10 minutes to 120 minutes until a water content of 20 wt % or lower is attained. The step of surface crosslinking is to add a surfactant by 0.001 parts by weight to 10 parts by weight to 100 parts by weight of the water-absorbable resin powder thus dried, and treating the water-absorbable resin powder thermally at a temperature of 70° C. to 300° C. for 1 minute to 2 hours. Through these steps, it is possible to attain a p-methoxy phenol content of 5 ppm to 60 ppm in the resultant water-absorbable resin powder.

The water-absorbable resin powder according to the present invention is, as illustrated in (2-9) above, preferably configured to comprise an additive selected from chelating agents, α-hydroxy carboxylic acid, inorganic or organic reducing agents. Because of the additive, the water-absorbable resin powder according to the present invention can be improved in terms of coloring or durability, even if the water-absorbable resin powder has a large surface area that would adversely affect in terms of coloring or durability.

Moreover, like the second water-absorbable resin described later, the water-absorbable resin (first water-absorbable resin powder) is water-absorbable polyacrylic acid resin powder internally containing a surfactant and/or a dispersing agent. Further, it is preferable that the water-absorbable resin has a surface tension of 60 [mN/m] or greater, and particle surface of the water-absorbable resin are covered with the surfactant. Similarly, it is preferable that saline flow conductivity (SFC) is 20 [×$10^{-7}$·cm$^3$·sec·g$^{-1}$] or greater, and water absorbing rate (FSR) is 0.25 [g/g/sec] or greater.

Like the second water-absorbable resin described later, the water-absorbable resin (first water-absorbable resin powder) is configured such that water content (defined in Examples) is preferably 15 wt % or less, more preferably in a range of 0.1 to 10 wt %, and further preferably in a range of to 8 wt %. If the water content is too low, the water absorbing rate (for example, FSR) and the impact resistance become poor. If the water content is high, the absorbency without pressure (CRC) and the absorbency against pressure (AAP) are lowered. The water content can be adjusted by the heating temperature or heating time of heating after the polymerization, or adding water.

(Novel Second Water-Absorbable Resin Powder)

The present invention provides water-absorbable resin powder obtainable by the process for production of water-absorbable resin powder, wherein the surfactant and/or the dispersing agent is added in polymerization, and the process preferably further includes the step of further coating the surface of the water-absorbable resin powder with the surfactant, the water-absorbable resin powder being water-absorbable polyacrylic acid resin powder which contains the surfactant and/or the dispersing agent substantially uniformly inside thereof, wherein a surface tension is 60 [mN/m] or greater and particle surface of the water-absorbable resin powder is coated with the surfactant.

The surfactants present on the surface and contained inside can be distinguished by polishing the particle surface or subjecting only the surfaces to solvent extraction, and then determining whether there is a quantitative difference in density of the surfactant along a thickness direction of the particles.

That is, the present invention provides novel water-absorbable resin (second water-absorbable resin powder), which is polyacrylic acid water-absorbable resin containing a surfactant and/or a dispersing agent inside thereof, wherein a surface tension is 60 [mN/m] or more, and particle surface of the water-absorbable resin is coated with the surfactant.

Such novel water-absorbable resin has a high surface tension, whereby Re-Wet in disposable diaper using the same is low, and a high Probe Insertion Distance disclosed in U.S. Pat. No. 7,282,262 can be achieved with a very small amount of the surfactant.

The water-absorbable resin powder (second water-absorbable resin powder) is preferably such that its probe insertion distance (PID) is 13 [mm] or more.

The probe insertion distance (PID) can be controlled by providing the surfactant inside the particles (in the polymerization) or on the particle surface (after the drying; especially surface crosslinking), especially by providing the surfactant inside the particles and on the particle surface (see Examples described later and in Table 6).

Because the surface of the water-absorbable resin powder is coated with the surfactant, the water-absorbable resin powder is improved in anti-damaging property, and property deterioration of the water-absorbable resin powder during or after the production will not occur. The water-absorbable resin attains both the permeability potential and the water absorbing rate, and is preferably configured such that the saline flow conductivity (SFC) is 20 [×$10^{-7}$·cm$^3$·sec·g$^{-1}$] or greater, and water absorbing rate (FSR) is 0.25 [g/g/sec] or greater.

(Other Properties)

The water-absorbable resin powder obtainable by the production process according to the present invention, or the first or second water-absorbable resin powder is preferably configured to satisfy the following properties. When they are to be used in sanitary goods, especially, disposable diapers, they are controlled by the polymerization or surface crosslinking so as to satisfy preferably (i) at least one of (3-1) to (3-7), more preferably (ii) AAP and at least one other of (3-1) to (3-7), or especially preferably (iii) AAP and at least two others of (3-1) to (3-7). If the following properties were not satisfied, the water-absorbable resin powder would not be able to sufficiently perform in a later-described high-concentration disposable diaper.

The production process according to the present invention is applicable to the following process for production of the water-absorbable resin powder. More preferably, the production process according to the present invention is applicable to control and improvement in the permeability potential (SFC) or water absorbing rate (FSR). The following properties and the properties in Example are defined by EDNA, unless otherwise specified.

The water-absorbable polyacrylic acid resin powder according to the present invention is configured such that a water absorbing rate index defined by the following equation is 90 or more, and a bulk specific gravity is preferably in a range of 0.58 to 0.8 [g/cm$^3$] further preferably in a range of 0.6 to 0.8 [g/cm$^3$].

A process for production of such water-absorbable resin powder according to the present invention is characterized in surface crosslinking water-absorbable polyacrylic acid resin powder in which a water absorbing rate index defined by the following equation is 90 or more, and a bulk specific gravity is preferably in a range of 0.58 to 0.8 [g/cm$^3$] further preferably in a range of 0.6 to 0.8 [g/cm$^3$]. The aforementioned methods can be preferably adopted to perform the surface crosslinking or control of the water absorbing rate index. The water-absorbable resin powder according to the present invention is preferably surface-crosslinked and further preferably has a water absorbing rate index within the range mentioned above.

(Water Absorbing Rate Index)=(FSR [g/g/sec])×
(Bulk Specific Gravity [g/cm$^3$])×
(Weight Average Particle Diameter [μm])

where FSR is a water absorbing rate for saline so as to swell 20-fold.

The water absorbing rate index may be 90, 95, 100, 105, 110, 115, or 120, where the higher values are more preferable.

An upper limit of the water absorbing rate index is 150 or may be 140 to be satisfactory. The novel water-absorbable resin powder is excellent in permeability potential and impact resistance, and can be preferably used in absorbing products such as disposable diapers. Water-absorbable resin powder with too low or too high in water absorbing rate index tends to be unsuitable for practical usage.

The water-absorbable resin powder has a foamed structure (also called porous structure). The porous structure can be determined by taking an electromicroscopic picture of the particle surface. An average pore diameter on the particle surface is preferably 100 µm or less, more preferably in a range of 0.1 µm to 90 µm, and further preferably in a range of 1 µm to 50 µm. The water-absorbable resin powder is mainly constituted by porous particles.

(3-1) AAP (Absorbency Against Pressure)

In order to prevent leakage in disposable diapers, absorbency (AAP) for 0.9 wt % sodium chloride aqueous solution under load of 1.9 kPa or 4.8 kPa is controlled to be preferably 20 [g/g] or more, more preferably 22 [g/g] or more, and further preferably 24 [g/g] or more, for example by the surface crosslinking after the polymerization. A higher upper limit of AAP is more preferable. However, considering a balance with the other properties, the upper limit of AAP is normally 40 [g/g], and preferably 35 [g/g]. In case of AAP under load of 4.8 kPa, it is preferable that the upper limit is approximately 30 [g/g].

(3-2) CRC (Absorbency without Pressure)

CRC (Absorbency without pressure) is controlled to be preferably 10 [g/g] or more, more preferably 20 [g/g] or more, further preferably 25 [g/g] or more, and especially preferably 30 [g/g] or more. A higher upper limit of CRC is more preferable. However, considering a balance with the other properties (especially the permeability potential), the upper limit of CRC is preferably 50 [g/g] or less, more preferably 45 [g/g] or less, and further preferably 40 [g/g] or less. CRC can be controlled by crosslinking agent content etc. In Non-Patent Literature 1, Table 5.6 discloses absorbencies of commercially available water-absorbable resin (without details as to how to measure the absorbencies). More specifically, Non-Patent Literature 1 discloses the absorbency of Aquakeep is 65.4 [g/g], and that of Sanwet 1M-1000 is 58.3 [g/g]. In order to further attain the object (both of permeability potential and water absorbing rate) of the present invention, it is preferable in the present invention that the absorbency without pressure (CRC) is controlled within the above range.

(3-3) SFC (Saline Flow Conductivity)

In order to prevent the leakage in disposable diaper, for example by the polymerization and surface-crosslinking of particle-size adjusted particles, the particle diameter control, and further the surface crosslinking, the saline flow conductivity (SFC) (permeability potential of a liquid against pressure) for 0.69 wt % saline is 1 [$\times 10^{-7} \cdot cm^3 \cdot sec \cdot g^{-1}$] or more, and more preferably 20 [$\times 10^{-7} \cdot cm^3 \cdot sec \cdot g^{-1}$] or more, further preferably 50 [$\times 10^{-7} \cdot cm^3 \cdot sec \cdot g^{-1}$] or more, still further preferably 70 [$\times 10^{-7} \cdot cm^3 \cdot sec \cdot g^{-1}$] or more, yet further preferably 100 [$\times 10^{-7} \cdot cm^3 \cdot sec \cdot g^{-1}$] or more, still yet further preferably 120 [$\times 10^{-7} \cdot cm^3 \cdot sec \cdot g^{-1}$] or more, and especially is controlled to be 140 [$\times 10^{-7} \cdot cm^3 \cdot sec \cdot g^{-1}$] or more. SFC is a well-known measuring method, and for example, can be defined by the method described in U.S. Pat. No. 5,562,646. The water-absorbable resin according to the present invention in which the closed cell rate is controlled can attain both the SFC and FSR at high levels. The upper limit of the SFC can be determined as appropriate, but is preferably 1000 [$\times 10^{-7} \cdot cm^3 \cdot sec \cdot g^{-1}$] approximately in consideration of a balance with the other properties.

The present invention is preferably applied to the production of water-absorbable resin powder with a high permeability potential, because the present invention is remarkably effective to attain the permeability potential improvement, especially SFC improvement, especially to attain SFC within the above range, or specifically SFC of 20 [$\times 10^{-7} \cdot cm^3 \cdot sec \cdot g^{-1}$] or more.

The water-absorbable resin of the present invention (especially, the first water-absorbable resin in which the closed cell rate is controlled, or the second water-absorbable resin powder in which the surfactant is contained on the surface and inside of the particles) has such a high permeability potential that SFC is 50 [$\times 10^{-7} \cdot cm^3 \cdot sec \cdot g^{-1}$] or more, and further 100 [$\times 10^{-7} \cdot cm^3 \cdot sec \cdot g^{-1}$] or more, but show a small reduction in SFC such as, preferably 15 [$\times 10^{-7} \cdot cm^3 \cdot sec \cdot g^{-1}$] or less, more preferably 10 [$\times 10^{-7} \cdot cm^3 \cdot sec \cdot g^{-1}$] or less, especially preferably 5 [$\times 10^{-7} \cdot cm^3 \cdot sec \cdot g^{-1}$] or less. Thus, the water-absorbable resin of the present invention is excellent in anti-damaging property.

(3-4) Ext (Water Soluble Content)

The water soluble content is preferably 35 wt % or less, more preferably 25 wt % or less, further preferably 15 wt % or less, and especially preferably 10 wt % or less.

(3-5) FSR (Water Absorbing Rate)

For example by the polymerization (foaming polymerization), the water-absorbable resin of the present invention has a water absorbing rate (FSR) (for 20 g of saline per 1 g of water-absorbable resin powder) of normally 0.05 [g/g/sec] or more, preferably 0.1 [g/g/sec] or more, more preferably 0.15 [g/g/sec] or more, further preferably 0.20 [g/g/sec] or more, especially preferably 0.25 [g/g/sec] or more. As to an upper limit thereof, 0.50 [g/g/sec] or less, and more preferably 1.0 [g/g/sec] or less. The measuring method of FSR is defined in the pamphlet of PCT international publication No. 2009/016055. The water-absorbable resin according to the present invention whose closed-cell rate has been controlled can attain both of the SFC and FRS at high levels.

(3-6) Bulk Specific Gravity

The bulk specific gravity of the water-absorbable resin powder is normally in a range of 0.58 to 0.8 (equivalent to 0.58 to 0.80) [$g/cm^3$], preferably in a range of 0.6 to 0.8 (equivalent to 0.60 to 0.80) [$g/cm^3$], more preferably in a range of 0.63 to 0.77 [$g/cm^3$], and further preferably in a range of 0.66 to 0.74 [$g/cm^3$], The water-absorbable resin powder according to the present invention has a foamed structure (or porous structure) but has a high bulk specific gravity.

In Table 5.6 of Non-Patent Literature 1, bulk specific gravities of commercially available water-absorbable resin are disclosed (without details on measuring method). More specifically, Table 5.6 of Non-Patent Literature 1 discloses that Aquakeep has a bulk specific gravity of 0.4430 [$g/cm^3$], Sanwet 1M-1000 has a bulk specific gravity of 0.5624 [$g/cm^3$], and Dry Tech 510 has a bulk specific gravity of 0.8989 [$g/cm^3$]. In the present invention, it is preferable that the bulk specific gravity is within the above range. The bulk specific gravity can be controlled by the production process according to the present invention.

(3-7) Surface Tension

The surface tension (defined by the measuring method in Example) is preferably 60 [mN/m] or more, more preferably 65 [mN/m] or more, further preferably 67 [mN/m] or more, especially preferably 70 [mN/m] or more, and most preferably 72 [mN/m] or more. In the present invention, no reduction in surface tension occur substantially. An upper limit of the surface tension is normally 75 [mN/m] to be satisfactory.

[4] APPLICATION OF WATER-ABSORBABLE POLYACRYLIC ACID RESIN POWDER

The water-absorbable resin powder according to the present invention is not limited to particular applications, but is preferably applicable to absorbing products such as disposable diaper, sanitary napkins, incontinence pad. The water-absorbable resin powder according to the present invention attains both the permeability potential and water absorbing rate, and further excellent in impact resistance and absorbency against pressure. Thus, the water-absorbable resin powder according to the present invention can be preferably used in absorbing product having high water-absorbable resin content. The absorbing goods, which may contain other absorbing material(s) (such as pulp fibers etc.), has water-absorbable resin powder content (core concentration) of 30 wt % to 100 wt %, preferably 40 wt % to 100 wt %, more preferably 50 wt % to 100 wt %, further preferably 60 wt % to 100 wt %, especially preferably 70 wt % to 100 wt %, most preferably 75 wt % to 95 wt %, in order to exhibit the effect of the present invention.

[5] EXAMPLES

In the following, the present invention is explained based on Examples, which are not to limit the present invention. The properties recited in the Claims and Examples are obtained according to the measurement methods (5-1) to (5-15). The steps described in Examples are performed under substantially atmospheric pressure (atmospheric pressure±5%, further preferably ±1%), unless otherwise specified. Each step is performed without an intentional pressure change to increase or decrease the pressure throughout the step.

(5-1) Weight Average Particle Diameter (D50) and Logarithmic Standard Deviation of Particle Diameter Distribution ($\sigma\xi$)

According to US patent application publication No. 2006/204755, the particles are classified by using standard sieves so as to find weight average particle diameter (D50) and logarithmic standard deviation ($\sigma\xi$).

(5-2) CRC (Absorbency without Pressure)

According to ERT 441.2-0.2, Absorbency without pressure (CRC) for 0.90 wt % sodium chloride aqueous solution (or saline) in 30 minutes was determined.

(5-3) Solid Content

Solid content is a ratio of component not volatile at 180° C. in the water-absorbable resin powder, and has such a relationship with water content that "solid content=100−water content".

The solid content was measured as follows.

In an aluminum cup (weight W3 [g]) with a bottom having about 5 cm diameter, about 1 g of water-absorbable resin powder was weighed (weight W4 [g]). The water-absorbable resin powder was dried by leaving the water-absorbable resin powder in the aluminum cup in a no-air flow drier at 180° C. for 3 hours. The sum weight of the aluminum cup and the water-absorbable resin powder after drying was measured (W5 [g]). From Equation 2, the solid content was measured.

$$\text{Solid content [wt \%]} = \{\{W5-W3\}/W4\} \times 100 \quad \text{Equation 2}$$

(5-4) FSR (Water Absorbing Rate)

Into a 25 ml glass beaker (diameter 32 to 34 mm, height 50 mm), 1.00 g of water-absorbable resin powder was measured. The water-absorbable resin powder put in the beaker was leveled off (if necessary, the beaker might be tapped gently to level the surface off).

Next, 20 g of 0.90 wt % sodium chloride aqueous solution adjusted to 23° C.±0.2° C. was measured in a 50 ml glass beaker. A total weight of the sodium chloride aqueous solution and the glass beaker was measured (weight W6 [g]). The weighed sodium chloride aqueous solution was poured quickly and carefully into the 25 ml beaker containing the water-absorbable resin powder. Timing was started at contact of the poured sodium chloride aqueous solution with the water-absorbable resin powder. The timing (time $t_s$, [sec]) was finished when the surface of the sodium chloride aqueous solution was replaced with the surface of the water-absorbable resin powder absorbing the sodium chloride aqueous solution was observed by visual monitoring, at about 20°, the surface of the sodium chloride aqueous solution in the beaker into which the sodium chloride aqueous solution was poured.

Next, the weight (weight W7 [g]) of the 50 ml glass beaker to which the sodium chloride aqueous solution had been poured. The weight W8 of the sodium chloride aqueous solution thus poured was calculated out from Equation 3. FSR was obtained from Equation 4.

$$W8 \text{ [g]} = W6 - W7 \quad \text{Equation 3}$$

$$\text{FSR [g/g/sec]} = W8/(t_s \times \text{weight of water-absorbable resin powder [g]}) \quad \text{Equation 4}$$

(5-5) Bulk Specific Gravity

The bulk specific gravity was measured according to JIS K3362 using a bulk specific gravity measuring device (made by Kuramochi Kagaku Kiki Seisakusho Co. Ltd.). Into a funnel with a closed dumper, 100.0 g of water-absorbable resin powder having been thoroughly mixed to eliminate deviation due to particle diameter was introduced. Then, the dumper was quickly opened to dump the water-absorbable resin powder into a 100 ml receiver (weight W9 [g]). The water-absorbable resin powder was rubbed with a glass rod so as to rub off a mound of the water-absorbable resin powder over a top of the receiver. Then, weight of the receiver with the water-absorbable resin powder (weight W10 [g]) was measured accurately to one digit after decimal. Then, the bulk specific gravity was calculated according to Equation 5.

$$\text{Bulk specific gravity [g/ml]} = (W10 - W9)/100 \quad \text{[Equation 5]}$$

The measurement was carried out at a temperature of 24.2° C. under relative humidity of 43% RH.

(5-6) Surface Tension

Into a 100 ml beaker thorough washed, 50 ml of saline adjusted to 20° C. was introduced and surface tension thereof was measured by a surface tension measuring device (K11 Auto tensiometer; KRUSS GmBH). The surface tension should be within a range of 71 o 75 [mN/M] by this measurement.

Next, into the beaker with the saline having been adjusted to 20° C. and subjected to the surface tension measurement, a well-washed fluorine resin stirrer of 25 mm and 0.5 g of water-absorbable resin powder was introduced, and stirred for 4 minutes by 500 rpm. Four minutes later, the stirring was stopped, and the water-absorbed water-absorbable resin powder was let precipitated. Then, surface tension of the supernatant was measured by the same way as above. In the present invention, a plate method using a platinum plate was used. The plate was well washed with deionized water and by being heated with gas burner before the measurement.

(5-7) Permeability Potential (SFC)

SFC was measured by a well-known measurement method described in U.S. Pat. No. 5,562,646 B.

(5-8) Degree of Whiteness (Initial Coloring)

As an index indicating initial coloring (coloring right after the production of the water-absorbable resin), degree of whiteness indicates how white the powder is. X, Y, and Z values of the degree of whiteness are calculated out by using L, a, and b values. For comparing the degree of whiteness, WB value of water-absorbable resin powder is useful. The WB value was measured by using a spectral colorimeter. Here, coloring (proceeding) due to aging in a long term storage or coloring (proceeding) inside sanitary goods are referred to as aging coloring, in comparison with the initial coloring.

Spectral colorimeter: Spectrophotometer SE6000 made by Nippon Denshoku Industries Co. Ltd.

Powder sampling cell: φ35 mm, 15 mm in height.

(5-9) Anti-Damaging Test

The water-absorbable resin powder was damaged by vibrating for 10 minutes according to mechanical damaging test described in Patent Literature 38 (U.S. Pat. No. 6,562,879) and its JP family, Japanese Patent Application Publication, Tokukai, No. 2000-302876 A (page 12, paragraphs [0285], [0286]).

(5-10) Apparent Density (See FIG. 12)

After moisture was further eliminated in the water-absorbable resin powder, the apparent density of the powder was measured (the closed cells inside the particles were also considered) by dry density measurement (dry measurement to measure volume of the water-absorbable resin powder with predetermined weight).

That is, 6.0 g of the water-absorbable resin powder was weighed in an aluminum cup of about 5 cm in diameter of bottom surface, and left in a no-air flow dryer at 180° C. for 3 hours or longer until the water-absorbable resin powder was dried to water content of 1% or below. Then, the apparent density (weight g/volume cm$^3$) of 5.00 g of the water-absorbable resin thus dried was measured with helium gas by using dry automatic densimeter; Micromeritics Auto Pycnometer 1320 made by Shimazu Corporation. The measurement was repeated until the same readings were obtained sequentially twice or more.

(5-11) Real Density (See FIGS. 12 and 13)

The real density of the present invention was determined by measuring dry density of water-absorbable resin powder whose closed cells inside have been broken or converted into open cells by finely grinding the water-absorbable resin powder to that extent that it could pass through a 45-μm JIS standard sieve.

Cell diameters (closed cells) contained inside the water-absorbable resin are usually in a range of 1 μm to 300 μm. However, the grinding tends to break the particles at portions close to the cells. Thus, the water-absorbable resin powder having been ground to 45 μm or less has substantially no closed cells. Therefore, the real density of the water-absorbable resin powder was measured by measuring dry density of the water-absorbable resin powder having been ground to 45 μm or less.

The real density of the water-absorbable resin powder having been ground to the extent that it could pass a 45-μm JIS standard sieve. That is, 15.0 g of water-absorbable resin powder was introduced in a ball mill pot (Teraoka Corporation, ceramic ball mill pot-type No. 90, Internal size: 80 mm in diameter, 75 mm in height, Outer size: 90 mm in diameter, 110 mm in height) together with 400 g of circular column-shaped ceramic ball (13 mm in diameter, 13 mm in length). Then, by using the ball mill, the water-absorbable resin powder was finely ground for 2 hours at 60 Hz, thereby obtaining water-absorbable resin powder, 70% wt % or more of which could pass through the 45-μm JIS sieve.

The water-absorbable resin powder was classified by using the 45-μm JIS sieve, thereby obtaining water-absorbable resin powder less than 45 μm. Then, 6.0 g of the water-absorbable resin powder thus obtained was dried for 3 hours at 180° C. and its dry density was measured in the same way as the apparent density in (5-10) above. The real density in the present invention was measured in this way.

(5-12) Internal Cell Rate (or Closed Cell Rate)

By using the apparent density (density $\rho 1$ [g/cm$^3$]) thus measured as described in "(5-10) Apparent density", and the real density (density $\rho 2$ [g/cm$^3$]) thus measured as described in "(5-11) real density", the internal cell rate of the water-absorbable resin powder was calculated out according to Equation 6.

Intenal cell rate [%]=($\rho 2-\rho 1$)/$\rho 2 \times 100$    Equation 6

(5-13) Maximum Probe Insertion Load (PIL) and Probe Insertion Distance (PID)

These two items were measured according to the measuring methods for Maximum probe insertion load (PIL) and Probe insertion distance (PID) disclosed in U.S. Pat. No. 7,282,262.

(5-14) Methoxy Phenol Content

According to soluble content measuring method in ERT 470.2-02, 1.000 g of water-absorbable resin was added in 200 ml of 0.9 wt % sodium chloride aqueous solution and stirred for 1 hour (the stirring time was changed from 16 hours to 1 hour). Then, a resultant solution was filtered to obtained a filtrate. The methoxy phenol content was obtained by analyzing the filtrate.

More specifically, the filtrate obtained by the analysis operation of the ERT 470.2-02 (where the stirring was performed for 1 hour) was analyzed by high-speed liquid chromatography, so as to find p-methoxy phenol (in water-absorbable resin).

(5-15) Antiweatherability Improvement Test (Deterioration Rate)

This is defined according to the method described in PCT/JP2010/067086.

More specifically, 3.0 g of water-absorbable resin powder was put in a silica separable flask of 7.0 cm in inner diameter and 14.0 cm in height. Then, 57.0 g of deionized water was added, thereby 20-fold swelling gel particles (60 g) was obtained. Then, the 20-fold swelling gel particles were irradiated with ultraviolet rays radiation intensity 60 [mW/cm$^2$] for 1 minute at room temperature under stirring in the separable flask, wherein the ultraviolet irradiation was performed by using an ultraviolet ray irradiating device (Ushio Inc.; UV-152/1MNSC3-AA06) provided with a metal halide lamp (Ushio Inc.; UVL-1500M2-N1), and the stirring was performed by a stirring device having four flat blades having a length of 3.0 cm from an axis to a blade end, and a width of 1.0 cm. Thereby, hydrogel absorbing agent having been subjected to antiweatherability improvement test was obtained.

Next, into a plastic vessel of 250 ml in capacity with a lid, 184.3 g of 0.9 wt % sodium chloride aqueous solution and 2.00 g of the hydrogel absorbing agent thus obtained were introduced and stirred with magnetic stirrer for 16 hours, thereby extracting soluble content of the hydrogel absorbing agent. Extract was filtered with a filter paper (ADVANTEC Toyo Roshi Kaisha Ltd.; Product name: JIS P 3801, No. 2, Thickness: 0.26 mm, Retaining Particle Diameter: 5 μm). Then, 5.0 g of filtrate thus obtained and 45.0 g of 0.90 wt % sodium chloride aqueous solution was mixed to prepare a measurement solution.

Next, the measurement solution was titrated with 0.1N NaOH aqueous solution until it reached pH10. Then, the measurement solution was titrated with 0.1 N HCl aqueous solution until it reached pH 2.7. Thereby, titres ([NaOH] ml, and [HCl] ml) were obtained.

The same titrations were performed with 184.3 g of 0.90 wt % sodium chloride aqueous solution in order to obtain control titres ([bNaOH] ml, [bHCl] ml). From these values thus obtained, the soluble content was calculated out.

The deterioration rate was worded out from a difference in the soluble content between the hydrogel absorbing agent (after deterioration) and the water-absorbable resin powder (before deterioration). In the following Examples, the soluble content (wt %) was not described, but it was within a range of 15 wt % or less (10 wt % or less) in all the Examples.

Example 1

Into a polypropylene vessel of 3 L in capacity, 181.1 g of acrylic acid (containing p-methoxy phenol by 70 mg/L), 1727.0 g of 37 wt % sodium acrylate aqueous solution, 4.38 g of polyethylene glycol diacrylate (molecular weight 523) as an internal crosslinking agent, 59.7 g of 13.7 wt % polyoxy ethylene (20) sorbitan monostearate (Kao corporation) aqueous solution as a surfactant were introduced and dissolved (mixed), thereby obtaining a monomer aqueous solution (1). The monomer aqueous solution (1) was adjusted to 24° C.

Next, by using a constant rate pump the monomer aqueous solution (1) was passed at 0.5 [L/min] through a stainless coil-type heat exchanger (independent coil-type exchanger, Product Code: JC-S1; As One Corporation, Research Instrument union catalog) immersed in an oil bath of 100° C. Thereby, the temperature of the monomer aqueous solution (1) was increased to 98.5° C. At the time, the surfactant-containing monomer aqueous solution (1) was whitely turbid due to very fine bubbles. This was caused because solubility of gas was lowered by the heating of the monomer aqueous solution (1).

Then, 986 g of the monomer aqueous solution (1) was measured in a polypropylene vessel of 1 L in capacity, and cooled under stirring. When the temperature of the monomer aqueous solution (1) reached 95° C., 14.0 g of 4 wt % sodium persulfate aqueous solution was added therein. Immediately after that, the monomer aqueous solution (1) was poured into a stainless butt vessel (340 mm×340 mm bottom, 25 mm height with Teflon (registered trademark) coated inner surface) under atmospheric pressure. Note that the butt vessel had been heated to a surface temperature of 80° C. by using a hot plate (Iuchi Seiei Do Ltd.; NEO HOTPLATE HI-1000).

Forty (40) seconds after the monomer aqueous solution (1) was poured into the butt vessel, polymerization was started. The polymerization proceeds with stream generation and foaming and swelling in various directions. Then, the swelling was shrunk to a size slightly larger than the butt vessel. The swelling and shrinking terminated within about 1 minute. Three (3) minutes later from the start of the polymerization, a resultant hydrogel crosslinked polymer (hydrogel) was taken out of the butt vessel. These process was performed under atmospheric pressure. A peak temperature in the polymerization was 110° C.

The hydrogel crosslinked polymer (hydrogel) thus obtained in the polymerization was crushed by using a meat chopper (Iizuka Kogyo Co. Ltd. MEAT-CHOPPER TYPE: 12VR-400KSOX, die pore diameter: 6.4 mm, pore number: 38, die thickness: 8 mm), thereby obtaining crushed hydrogel crosslinked polymer. The crushing was performed by supplying the hydrogel at a rate of 350 [g/min] and 90° C. deionized water a rate of 80 [g/min] concurrently.

The crushed hydrogel crosslinked polymer thus obtained by the crushing was spread on a stainless mesh of 850 μm in mesh size, and dried with hot air of 180° C. for 30 minutes. Then, the dried thus obtained by the drying was ground by using a roll mill (Inoguchi Giken Ltd., WML-type role grinding device), and classified by using JIS standard sieves of 850 μm and 45 μm in mesh size.

In this way, prepared was water-absorbable resin powder (1) with solid content of 97 wt %, weight average particle diameter (D50) of 420 μm, logarithmic standard deviation (σξ) of particle diameter distribution of 0.36, and irregular broken shapes. Properties of the water-absorbable resin powder (1) are listed in Table 1.

Example 2

Into a polypropylene vessel of 2 L in capacity, 351.6 g of acrylic acid, 2.17 g of polyethylene glycol diacrylate (molecular weight 523) as an internal crosslinking agent, 94.6 g of 0.1 wt % diethylentriamine pentaacetate trisodium aqueous solution as a chelating agent, 144.9 g of 48.5 wt % sodium hydroxide aqueous solution, 6.45 g of 1.0 wt % polyoxyethylene (20) sorbitan monostearate (Kao corporation) aqueous solution as a surfactant, 236.0 g of deionized water (ion exchange water) were introduced and dissolved (mixed), thereby obtaining a monomer aqueous solution (2'). Temperature of the aqueous solution (2') was increased to 65° C. due to first-stage neutralization in the process. Solubility of gas was lowered due to the temperature increase, thereby introducing very fine bubbles in the surfactant-containing aqueous solution (2') and so as to cause the aqueous solution (2') to be whitely turbid consequently.

Then, the monomer aqueous solution (2') was cooled under stirring. When the temperature reached 53° C., 148.9 g of 48.5 wt % sodium hydroxide aqueous solution adjusted to 30° C. was added and mixed therein, thereby preparing a monomer aqueous solution (2). Here, the temperature of the monomer aqueous solution (2) was increased to 83.5° C. due to second-stage neutralization heat caused right after the preparation thereof. Owning to the lowering of the solubility of the gas due to the temperature increase, the surfactant-containing monomer aqueous solution (2) was in white turbid with the very fine bubbles introduced therein.

Next, when the temperature of the monomer aqueous solution (2) was cooled to 83° C., 15.3 g of 3.8 wt % sodium persulfate aqueous solution was added therein under stirring. Immediately after that, the monomer aqueous solution (2) was poured into a stainless butt vessel (340 mm×340 mm bottom, 25 mm height with Teflon (registered trademark) coated inner surface) under atmospheric pressure. Note that the butt vessel had been heated to a surface temperature of 40° C. by using a hot plate (Iuchi Seiei Do Ltd.; NEO HOTPLATE HI-1000). Dissolved oxygen content in the monomer aqueous solution (2) before the addition of the sodium persulfate aqueous solution was 6.53 [ml/L].

Fifteen (15) seconds after the monomer aqueous solution (2) was poured into the butt vessel, polymerization was started. The polymerization proceeds with stream generation and foaming and swelling in various directions. Then, the swelling was shrunk to a size slightly larger than the butt vessel. The swelling and shrinking terminated within about 1 minute. Three (3) minutes later from the start of the polymerization, a resultant hydrogel crosslinked polymer (hydrogel)

was taken out of the butt vessel. These process was performed under atmospheric pressure. A peak temperature in the polymerization was 108° C.

After that, the resultant hydrogel crosslinked polymer (hydrogel) was subjected to crushing, drying, grinding, and classifying in the same was as in Example 1.

In this way, prepared was water-absorbable resin powder (2) with solid content of 97 wt %, weight average particle diameter (D50) of 460 μm, logarithmic standard deviation (σξ) of particle diameter distribution of 0.40, and irregular broken shapes. Properties of the water-absorbable resin powder (2) are listed in Table 1. Further, a degree of whiteness of the water-absorbable resin powder (2) is shown in Table 2.

Example 3

Into a polypropylene vessel of 1 L in capacity, 379.07 g of 37 wt % sodium acrylate aqueous solution, 0.995 g of polyethylene glycol diacrylate (molecular weight 523) as an internal cross linking agent, 176.31 g of deionized water (ion exchanged water), 0.04 g of polyoxyethylene (20) sorbitan monostearate (Kao Corporation) as a surfactant were introduced and dissolved (mixed), thereby obtaining a monomer aqueous solution (3). The monomer aqueous solution (3) was subjected to degassing process with nitrogen gas for 5 minutes, while being adjusted to 25° C.

Then, into the monomer aqueous solution (3), 39.75 g of acrylic acid, 2.45 g of 10 wt % sodium persulfate aqueous solution, 1.02 g of 0.1 wt % L-ascorbic acid aqueous solution, and 0.41 g of 0.1 wt % hydrogen peroxide solution were added therein in this order under stirring.

The addition of the acrylic acid (a water soluble organic material and a poor solvent for the gas) into the monomer aqueous solution (3) lowered the solubility of the gas, thereby resulting in white turbidity of the surfactant-containing monomer aqueous solution (3) by introducing very fine bubbles. Moreover, about four minutes after the addition of hydrogen peroxide solution, polymerization started. Initial temperature of the polymerization was 25.2° C., and a peak temperature of the polymerization was 90° C.

One (1) hour after the start of the polymerization, a resultant hydrogel crosslinked polymer was taken out of the polypropylene vessel, and then subjected to crushing, drying, grinding, and classifying in the same way as in Example 1.

In this way, prepared was water-absorbable resin powder (3) with solid content of 96 wt %, weight average particle diameter (D50) of 442 μm, logarithmic standard deviation (σξ) of particle diameter distribution of 0.39, and irregular broken shapes. Properties of the water-absorbable resin powder (3) are listed in Table 1.

Example 4

By using a line mixing, 595.4 [g/min] of 37 wt % of sodium acrylate aqueous solution, 198.6 [g/min] of 48 wt % sodium hydroxide aqueous solution, 300.1 [g/min] of 100 wt % acrylic acid, 2.71 [g/min] of a polyethylene glycol diacrylate (molecular weight 523) as an internal crosslinking agent, 204.7 [g/min] of deionized water (ion exchanged water), 0.42 [g/min] of 31 wt % diethylene triamin pentaacetate trisodium aqueous solution, 0.29 [g/min] of polyoxyethylene (20) sorbitan monostearate (Kao Corporation) aqueous solution as a surfactant were mixed, thereby preparing a monomer aqueous solution (4). Continuously, the monomer aqueous solution (4) was passed through a stainless, coil-type heat exchanger (independent coil-type exchanger, Product Code: JC-S1; As One Corporation, Research Instrument union catalog, see FIG. 1) immersed in an oil bath of 95° C.

Into the monomer aqueous solution (4) having passed through the heat exchanger, 26.0 [g/min] of 3 wt % sodium persulfate aqueous solution was added by line mixing, and continuously supplied to a continuous kneader (Dulton Co. Ltd., CKDJS-40), which served as a polymerizer having double stirrers. The monomer aqueous solution (4) to be supplied to the polymerizer had a temperature of 92° C. and a dissolved oxygen content of 4.26 [ml/L].

At the time, the surfactant-containing monomer aqueous solution (4) was whitely turbid due to very fine bubbles caused by lowering the solubility of the gas. Here, a jacket temperature of the polymerizer was set to 95° C., and nitrogen gas was blown in the polymerizer at a rate of 20 [L/min] (see FIG. 6).

Right after the monomer aqueous solution (4) was supplied in the polymerizer, the polymerization started. The polymerization and shearing of a resultant hydrogel crosslinked polymer were performed concurrently, and the hydrogel crosslinked polymer thus crushed was continuously discharged out of the polymerizer. After that, the hydrogel crosslinked polymer was then subjected to crushing, drying, grinding, and classifying in the same way as in Example 1.

In this way, prepared was water-absorbable resin powder (4) with solid content of 97 wt %, weight average particle diameter (D50) of 448 μm, logarithmic standard deviation (σξ) of particle diameter distribution of 0.41, and irregular broken shapes. Properties of the water-absorbable resin powder (4) are listed in Table 1.

Example 5

Production Additionally with Cell Introduction (for Example, Micro Bubble Introduction)

Into a polypropylene vessel of 2 L in capacity, 421.9 g of acrylic acid, 2.60 g of polyethylene glycol diacrylate (molecular weight 523) as an internal crosslinking agent, 113.5 g of 0.1 wt % diethylene triamine pentaacetate trisodium aqueous solution, 173.8 g of 48.5 wt % sodium hydroxide aqueous solution, and 0.44 g of 10.0 wt % polyoxyethylene (20) sorbitan monostearate (Kao Corporation) aqueous solution as a surfactant, 290.4 g of deionized water (ion exchanged water) were introduced and dissolved (mixed), thereby obtaining a monomer aqueous solution (5').

Temperature of the aqueous solution (5') was increased to 64° C. due to first-stage neutralization heat caused right after the preparation of the monomer aqueous solution (5'). Into the aqueous solution (5'), adjusted to 55° C., micro bubbles of nitrogen gas were introduced under absolute pressure of 0.30 to 0.35 MPa for 1 minute by using a micro bubble generating device (Aura Tech, Product code: OM4-GP-040), thereby preparing monomer aqueous solution (5') in which the micro bubbles were introduced. Note that the surfactant-containing aqueous solution (5') was whitely turbid due to the very fine bubbles introduced by the micro bubble generating device.

Next, 835 g of the monomer aqueous solution (5') was measured in a polypropylene vessel of 1 L in capacity, and cooled under stirring. When the temperature of the monomer aqueous solution (5') was cooled to 53° C., 148.9 g of 48.5 wt % sodium hydroxide aqueous solution adjusted to 30° C. was added and mixed therein, thereby preparing a monomer aqueous solution (5). Here, the monomer aqueous solution (5) had a temperature increased to 83.1° C. due to second-stage neutralization heat caused right after the preparation of the monomer aqueous solution (5). The temperature increase lowered the solubility of the gas, thereby resulting in white turbidity of the surfactant-containing monomer aqueous solution (5) due to the very fine bubbles thus introduced.

Next, when the temperature of the monomer aqueous solution (5) was lowered to 83° C., 15.3 g of 3.8 wt % sodium persulfate aqueous solution was added therein under stirring. Right after that, the monomer aqueous solution (5) was poured into a stainless butt vessel (340 mm×340 mm bottom, 25 mm height with Teflon (registered trademark) coated inner surface) under atmospheric pressure. Note that the butt vessel had been heated to a surface temperature of 40° C. by using a hot plate (Iuchi Seiei Do Ltd.; NEO HOTPLATE HI-1000).

Ten (10) seconds after the monomer aqueous solution (5) was poured into the butt vessel, polymerization was started. The polymerization proceeds with stream generation and foaming and swelling in various directions. Then, the swelling was shrunk to a size slightly larger than the butt vessel. The swelling and shrinking terminated within about 1 minute. Three (3) minutes later from the start of the polymerization, a resultant hydrogel crosslinked polymer (hydrogel) was taken out of the butt vessel. These process was performed under atmospheric pressure. A peak temperature in the polymerization was 111° C.

After that, the resultant hydrogel crosslinked polymer (hydrogel) was subjected to crushing, drying, grinding, and classifying in the same was as in Example 1. In this way, prepared was water-absorbable resin powder (5) with solid content of 97 wt %, weight average particle diameter (D50) of 451 µm, logarithmic standard deviation (σξ) of particle diameter distribution of 0.36, and irregular broken shapes. Properties of the water-absorbable resin powder (5) are listed in Table 1.

Example 6

Process Additionally with Bubble Introduction (for Example, Micro Bubble Introduction)

Process performed in Example 5 was carried out except that the addition of 10.0 wt % polyoxyethylene (20) sorbitan monostearate (Kao Corporation) aqueous solution as the surfactant was carried out right after the micro bubble introduction.

In this way, prepared was water-absorbable resin powder (6) with solid content of 97 wt %, weight average particle diameter (D50) of 448 µm, logarithmic standard deviation (σξ) of particle diameter distribution of 0.45, and irregular broken shapes. Properties of the water-absorbable resin powder (6) are listed in Table 1.

Example 7

Process performed in Example 2 was carried out except that 1.0 wt % sorbitan monolaurate (Kao Corporation) aqueous solution was used as a surfactant instead of 1.0 wt % polyoxyethylene (20) sorbitan monostearate (Kao Corporation) aqueous solution. In this way, a monomer aqueous solution (7) was prepared. The monomer aqueous solution (7) had a temperature increased to 63° C. due to neutralization heat caused right after the preparation of the monomer aqueous solution (7).

After that, the monomer aqueous solution (7) was processed as in Example 2, thereby obtaining water-absorbable resin powder (7) with solid content of 96 wt %, weight average particle diameter (D50) of 439 µm, logarithmic standard deviation (σξ) of particle diameter distribution of 0.44, and irregular broken shapes. Properties of the water-absorbable resin powder (7) are listed in Table 1.

Example 8

Process performed in Example 2 was carried out except that 1.0 wt % polyether modified silicone (side-chain modification with OH terminal) (Dow Corning Toray) aqueous solution was used as a surfactant instead of 1.0 wt % polyoxyethylene (20) sorbitan monostearate (Kao Corporation) aqueous solution. In this way, a monomer aqueous solution (8) was prepared. The monomer aqueous solution (8) had a temperature increased to 63° C. due to neutralization heat caused right after the preparation of the monomer aqueous solution (8).

Then, the same process as in Example 2 was carried out. In this way, prepared was water-absorbable resin powder (8) with solid content of 97 wt %, weight average particle diameter (D50) of 427 µm, logarithmic standard deviation (σξ) of particle diameter distribution of 0.39, and irregular broken shapes. Properties of the water-absorbable resin powder (8) are listed in Table 1.

Example 9

Process performed in Example 2 was carried out except that 14.3 g of 3.0 wt % sodium carboxymethylcellulose (Sigma-Aldrich Japan) aqueous solution as a surfactant was used instead of 6.45 g of 1.0 wt % polyoxyethylene (20) sorbitan monostearate (Kao Corporation) aqueous solution. In this way, a monomer aqueous solution (9) was prepared. The monomer aqueous solution (9) had a temperature increased to 64° C. due to neutralization heat caused right after the preparation of the monomer aqueous solution (9).

Then, the same process as in Example 2 was carried out. In this way, prepared was water-absorbable resin powder (9) with solid content of 96 wt %, weight average particle diameter (D50) of 463 µm, logarithmic standard deviation (σξ) of particle diameter distribution of 0.39, and irregular broken shapes. Properties of the water-absorbable resin powder (9) are listed in Table 1.

Comparative Example 1

Process performed in Example 1 was carried out except that 59.7 g of 13.7 wt % polyoxyethylene (20) sorbitan monostearate (Kao Corporation) aqueous solution was replaced with an equiamount of 59.7 g of deionized water (ion exchange water). In this way, prepared was comparative water-absorbable resin powder (1) with solid content of 97 wt %, weight average particle diameter (D50) of 432 µm, logarithmic standard deviation (σξ) of particle diameter distribution of 0.44, and irregular broken shapes. Properties of the comparative water-absorbable resin powder (1) are listed in Table 1.

A comparative monomer aqueous solution (1) prepared in Comparative Example 1 was heated, by using a heat exchanger (FIG. 1), to 98.5° C. substantially identically with Example 1. However, the lack of surfactant caused instability of the bubbles thus generated, thereby failing to introduce fine bubbles in the comparative monomer aqueous solution (1), which was substantially colorless and transparent.

Comparative Example 2

Process performed in Example 2 was carried out except that 6.45 g of 1.0 wt % polyoxyethylene (20) sorbitan monostearate (Kao Corporation) aqueous solution was replaced with an equiamount of 6.45 g of deionized water (ion exchange water). In this way, prepared was comparative water-absorbable resin powder (2) with solid content of 96 wt %, weight average particle diameter (D50) of 455 μm, logarithmic standard deviation (σξ) of particle diameter distribution of 0.37, and irregular broken shapes. Properties of the comparative water-absorbable resin powder (3) are listed in Table 1. Further, a degree of whiteness of the comparative water-absorbable resin powder (3) is shown in Table 2.

In a comparative monomer aqueous solution (2) prepared in Comparative Example 2, the lack of surfactant caused instability of the bubbles thus generated, thereby failing to introduce fine bubbles (white turbidity) in the comparative monomer aqueous solution (2), which was substantially colorless and transparent after the heating.

Comparative Example 3

Process performed in Example 2 was carried out except that 1.0 wt % polyoxyethylene [20] sorbitan monostearate (Kao Corporation) aqueous solution as a surfactant was not mixed into the monomer aqueous solution (2'), but into the monomer aqueous solution (2) after mixing the monomer aqueous solution (2') and the 48.5 wt % sodium hydroxide aqueous solution (at 83° C.). In this way, prepared was comparative water-absorbable resin powder (3) with solid content of 97 wt %, weight average particle diameter (D50) of 444 μm, logarithmic standard deviation (σξ) of particle diameter distribution of 0.43, and irregular broken shapes. Properties of the comparative water-absorbable resin powder (3) are listed in Table 1.

In a monomer aqueous solution prepared in Comparative Example 3, the lack of surfactant caused instability of the bubbles thus generated, whereby fine bubble introduction (white turbidity), which was observed in Example 2, was not observed monomer aqueous solution prepared in Comparative Example 3 even after adding the surfactant after the heating. Consequently, the monomer aqueous solution in Comparative Example 3 after the heating was substantially colorless and transparent.

Comparative Example 4

Process performed in Example 3 was carried out except that 0.04 g of polyoxyethylene (20) sorbitan monostearate (Kao Corporation) used as a surfactant in Example 3 was not used, thereby obtaining comparative water-absorbable resin powder (4) with solid content of 96 wt %, weight average particle diameter (D50) of 458 μm, logarithmic standard deviation (σξ) of particle diameter distribution of 0.40, and irregular broken shapes. Properties of the comparative water-absorbable resin powder (4) are listed in Table 1.

In a monomer aqueous solution prepared in Comparative Example 4, the lack of surfactant caused instability of the bubbles thus generated, whereby fine bubble introduction, which was observed in Example 3 after the addition of acrylic acid, was not observed in the monomer aqueous solution prepared in Comparative Example 4. Consequently, the monomer aqueous solution in Comparative Example 4 after the heating was substantially colorless and transparent.

Comparative Example 5

Process performed in Example 4 was carried out except that 10 wt % polyoxyethylene (20) sorbitan monostearate (Kao Corporation) aqueous solution used as the surfactant in Example 4 was not used, thereby obtaining comparative water-absorbable resin powder (5) with solid content of 97 wt %, weight average particle diameter (D50) of 450 μm, logarithmic standard deviation (σξ) of particle diameter distribution of 0.37, and irregular broken shapes. Properties of the comparative water-absorbable resin powder (5) are listed in Table 1.

In a monomer aqueous solution prepared in Comparative Example 5, the lack of surfactant caused instability of the bubbles thus generated, whereby fine bubble introduction, which was observed in Example 4, was not observed in the monomer aqueous solution prepared in Comparative Example 5. Consequently, the monomer aqueous solution in Comparative Example 5 after the heating was substantially colorless and transparent.

Comparative Example 6

Foaming polymerization was carried out with carbonate according to Patent Literatures 18 to 25. That is, into a polypropylene vessel of 1 L in capacity, 421.7 g of acrylic acid, 2.754 g of polyethylene glycol diacrylate (molecular weight 523) as an internal surfactant, 113.43 g of 0.1 wt % diethylene triamine pentaacetate trisodium aqueous solution, 140.4 g of 48.5 wt % sodium hydroxide aqueous solution, 292.3 g of deionized water (ion exchange water) were introduced and dissolved (mixed), thereby obtaining a comparative monomer aqueous solution (6').

Then, 211.9 g of 48.5 wt % sodium hydroxide aqueous solution adjusted to 40° C. was quickly added and mixed in the comparative monomer aqueous solution (6'), thereby preparing a comparative monomer aqueous solution (6). Here, the comparative monomer aqueous solution (6) thus had a temperature of 85° C.

When the temperature of the comparative monomer aqueous solution (6) was then cooled to 82° C., 5.2 g of sodium hydrogen carbonate (Wako Pure Chemical Industries Ltd.) was added therein. Then, 17.55 g of 4 wt % sodium persulfate aqueous solution was added therein under stirring. Right after that, the comparative monomer aqueous solution (6) was poured into a stainless butt vessel (340 mm×340 mm bottom, 25 mm height with Teflon (registered trademark) coated inner surface) under atmospheric pressure. In association with the addition of sodium hydrogen carbonate, generation of bubbles (believed to be bubbles of carbon dioxide gas) was observed, but the bubbles were very large in bubble diameter and foaming due to the bubbles had been disappeared and the comparative monomer aqueous solution (6) had been turned into a substantially colorless and transparent solution when the comparative monomer aqueous solution (6) was poured in the butt vessel. Note that the butt vessel had been heated to a surface temperature of 80° C. by using a hot plate (Iuchi Seiei Do Ltd.; NEO HOTPLATE HI-1000).

Soon after the comparative monomer aqueous solution (6) was poured into the butt vessel, the polymerization started. The polymerization proceeds with stream generation and foaming and swelling in various directions. Then, the swelling was shrunk to a size slightly larger than the butt vessel. The swelling and shrinking terminated within about 1 minute. Three (3) minutes later from the start of the polymerization, a resultant hydrogel crosslinked polymer (hydrogel) was taken out of the butt vessel. These process was performed under atmospheric pressure.

The hydrogel crosslinked polymer (hydrogel) thus obtained in the polymerization was crushed by using a meat chopper (Iizuka Kogyo Co. Ltd. MEAT-CHOPPER TYPE: 12VR-400KSOX, die pore diameter: 6.4 mm, pore number:

38, die thickness: 8 mm), thereby obtaining crushed hydrogel crosslinked polymer. The crushing was performed by supplying the hydrogel at a rate of 350 [g/min] and 90° C. deionized water a rate of 80 [g/min] concurrently.

The crushed hydrogel crosslinked polymer thus obtained by crushing was spread on a stainless mesh of 850 μm in mesh size, and dried with hot air of 180° C. for 30 minutes. Then, the dried thus obtained by the drying was ground by using a roll mill (Inoguchi Giken Ltd., WML-type role grinding device), and classified by using JIS standard sieves of 850 μm and 45 μm in mesh size.

In this way, prepared was comparative water-absorbable resin powder (6) with solid content of 96 wt %, weight average particle diameter (D50) of 436 μm, logarithmic standard deviation (σξ) of particle diameter distribution of 0.37, and irregular broken shapes. Properties of the comparative water-absorbable resin powder (6) are listed in Table 1.

Reference Example 1

The water-absorbable resin powder (2) thus obtained in comparative example 2 was classified by using JIS standard sieves of 150 μm and 45 μm in mesh size, thereby obtaining reference water-absorbable resin powder (1) in which particles passing the sieve of 150 μm not passing the sieve of 45 μm accounted for 92 wt % thereof and particles passing the sieve of 45 μm accounted for 8 wt % thereof.

Comparative Example 7

According to Patent Literature 34 (US patent Application Publication No. 2007/0225422), polymerization was carried out in the presence of the water-absorbable resin powder. That is, process same in Comparative Example 6 except that 5.2 g of sodium hydrogen carbonate (Wako Pure Chemicals industries Ltd.) added in Comparative Example 6 was not added and 25.8 g of the reference water-absorbable resin powder (1) obtained in Reference Example 1 right after the addition of 17.55 g of 4% wt sodium persulfate aqueous solution. In this way, prepared was comparative water-absorbable resin powder (7) with solid content of 97 wt %, weight average particle diameter (D50) of 446 μm, logarithmic standard deviation (σξ) of particle diameter distribution of 0.36, and irregular broken shapes. Properties of the comparative water-absorbable resin powder (7) are listed in Table 1.

Comparative Example 8

According to Patent Literature 30 (U.S. Pat. No. 6,107, 358), foaming polymerization by bubble dispersion was carried out. That is, a hydrogel crosslinked polymer thus obtained by the foaming polymerization was crushed by using a meat chopper (Iizuka Kogyo Co. Ltd. MEAT-CHOPPER TYPE: 12VR-400KSOX, die pore diameter: 6.4 mm, pore number: 38, die thickness: 8 mm), dried, ground, and classified, thereby obtaining comparative water-absorbable resin powder (8) with solid content of 95 wt %, weight average particle diameter (D50) of 450 μm, logarithmic standard deviation (σξ) of particle diameter distribution of 0.39, and irregular broken shapes. Properties of the comparative water-absorbable resin powder (8) are listed in Table 1. Note that the bubbles were dispersed in the monomer aqueous solution but the bubbles were very large in bubble diameter.

Comparative Example 9

The comparative water-absorbable resin powder (2) thus obtained in Comparative Example 2 was classified by using a JIS standard sieve of 600 μm in mesh size, thereby obtaining comparative water-absorbable resin powder (9) with solid content of 97 wt %, weight average particle diameter (D50) of 336 μm, logarithmic standard deviation (σξ) of particle diameter distribution of 0.39, and irregular broken shapes. Properties of the comparative water-absorbable resin powder (9) are listed in Table 1.

Example 10

Process performed in Example 4 was carried out except that the reference water-absorbable resin powder (1) was continuously supplied (recycled in the form of fine powder) at a rate of 57 [g/min] about when the polymerization was started right after the supply of the monomer aqueous solution (4) to the polymerizer, thereby obtaining water-absorbable resin powder (10) with solid content of 96 wt %, weight average particle diameter (D50) of 437 μm, logarithmic standard deviation (σξ) of particle diameter distribution of 0.43, and irregular broken shapes. Properties of the water-absorbable resin powder (10) are listed in Table 1.

TABLE 1

| | Properties after polymerization and drying | | | | | | | |
|---|---|---|---|---|---|---|---|---|
| | CRC [g/g] | FSR [g/g/sec] | BSG [g/cm³] | D50 [μm] | SC [wt %] | ST [mN/m] | DW [WB value] | ARI |
| Ex. 1 | 33.6 | 0.33 | 0.65 | 420 | 97 | | | 90 |
| Ex. 2 | 35.2 | 0.38 | 0.63 | 460 | 97 | 68.2 | 69.18 | 110 |
| Ex. 3 | 34.8 | 0.30 | 0.66 | 460 | 96 | 63.8 | | 91 |
| Ex. 4 | 35.3 | 0.36 | 0.65 | 448 | 97 | 72.5 | 69.32 | 105 |
| Ex. 5 | 34.9 | 0.39 | 0.63 | 451 | 97 | | | 111 |
| Ex. 6 | 33.8 | 0.43 | 0.62 | 448 | 97 | | | 119 |
| Ex. 7 | 36.5 | 0.35 | 0.64 | 439 | 96 | | | 98 |
| Ex. 8 | 34.0 | 0.45 | 0.58 | 427 | 97 | | | 111 |
| Ex. 9 | 33.2 | 0.32 | 0.66 | 463 | 96 | | | 98 |
| Ex. 10 | 33.1 | 0.40 | 0.61 | 437 | 96 | | 70.53 | 107 |
| CEx. 1 | 33.2 | 0.25 | 0.65 | 432 | 97 | | | 70 |
| CEx. 2 | 34.0 | 0.27 | 0.66 | 455 | 96 | 71.9 | 66.99 | 81 |
| CEx. 3 | 35.1 | 0.26 | 0.68 | 444 | 97 | | | 78 |
| CEx. 4 | 33.5 | 0.23 | 0.68 | 458 | 96 | | | 72 |
| CEx. 5 | 35.0 | 0.27 | 0.65 | 450 | 97 | | | 79 |
| CEx. 6 | 36.0 | 0.28 | 0.67 | 436 | 96 | | | 82 |
| CEx. 7 | 33.6 | 0.29 | 0.65 | 446 | 97 | | | 84 |

TABLE 1-continued

| | Properties after polymerization and drying | | | | | | | |
|---|---|---|---|---|---|---|---|---|
| | CRC [g/g] | FSR [g/g/sec] | BSG [g/cm³] | D50 [μm] | SC [wt %] | ST [mN/m] | DW [WB value] | ARI |
| CEx. 8 | 37.8 | 0.48 | 0.53 | 450 | 95 | | | 114 |
| CEx. 9 | 34.4 | 0.33 | 0.69 | 336 | 97 | | | 77 |

Abbreviations:
Ex. stands for Example.
CEx. stands for Comparative Example.
BSG stands for Bulk Specific Gravity.
SC stands for Solid Content.
ST stands for Surface Tension.
DE stands for Degree of Whiteness.
ARI stands for water Absorbing Rate Index.

TABLE 2

| | Excellency in Degree of Whiteness | | | |
|---|---|---|---|---|
| | Degree of Whiteness [WB value] | X value | Y value | Z value |
| Example 2 | 69.18 | 76.68 | 78.82 | 81.79 |
| Comparative Example 2 | 66.99 | 74.81 | 76.88 | 79.20 |

(Summary)

From Table 1, it can be understood that the production process according to the present invention can provide water-absorbable resin powder whose water absorbing rate (FSR) is improved without sacrificing the other properties, and without requiring expensive sub materials (a large amount of surfactant or foaming agent) or special equipment.

From the comparison between Examples 1 to 4 and Comparative Examples 1 to 5, it can be understand that the presence of the surfactant at lowering the solubility, heating, and mixing the aqueous organic material (acrylic acid) can improve the water absorbing rate (FSR) very much.

The conventional foaming polymerizations demonstrated in Comparative Examples 6 to 8 could not attain sufficient improvement in the water absorbing rate (FSR) (FSR in the order of 0.2 in Comparative Example 6 and 7), or resulted in a large degrease in the bulk specific gravity (in Comparative Example 8). The technique in which the average particle diameter is reduced as in Comparative Example 9 was not only insufficient in the improvement of the water absorbing rate (FSR), but also was associated with a large decrease in permeability potential (for example SFC) and a large increase in the amount of the fine powder (for example, the amount of the fine powder passing the sieve of 150 μm in mesh size) due to the particle size reduction.

The comparison between Example 4 (FSR; 0.36) and Example 10 (FSR; 0.40) shows that the recycling the fine powder can improve the water absorbing rate (FSR). It can be understood that the process additionally with the bubble introduction (micro bubble introduction in advance) demonstrated in Examples 5 and 6 can attain excellent results.

Further, Table 2 explains that the water-absorbable resin powder (2) according to the present invention was more white (larger in WB, X, Y, and Z) even though the amount of the chelating agent (serving as an anti-coloring agent or an anti-property deterioration agent) is equal in Example 2 and Comparative Example 2. The water-absorbable resin powder according to the present invention can attain not only a higher water absorbing rate (FSR) but also a higher degree of whiteness with the same amount of anti-coloring agent (chelating agent).

Example 11

Into the water-absorbable resin powder (2) obtained in Example 2, a surface crosslinking agent solution containing 0.48 parts by weight of 1,4-butanediol, 0.75 parts by weight of propylene glycol, and 4.0 parts by weight of deionized water with respect to 100 parts by weight of the water-absorbable resin powder (2) was uniformly sprayed and mixed. The particles of the water-absorbable resin mixed with the surface crosslinking agent solution was subjected to thermal crosslinking treatment of 45 minutes by using a hot-air dryer (temperature: 180° C.). After the heat treatment, the resultant particles of the water-absorbable resin was ground until the particles became small enough to pass the JIS standard sieve of 850 μm in mesh size, thereby obtaining surface-crosslinked particles of the water-absorbable resin.

Into 100 parts by weight of the surface-crosslinked particles of the water-absorbable resin thus obtained, a mixture solution containing 0.80 parts by weight of 27 wt % of aluminum sulfate aqueous solution (8 wt % based on aluminum oxide) as a multivalent metal cation, 0.134 parts by weight of 60 wt % of sodium lactic acid aqueous solution as α-hydroxycarboxylic acid aqueous solution, and 0.016 parts by weight of propylene glycol was added. After the addition, the particles were dried at 60° C. for 1 hour with no air flow. Then, the resultant particles was sieved with the JIS standard sieve of 850 μm in mesh size, thereby obtaining water-absorbable resin powder (11), whose properties are listed in Table 3.

Example 12

Process performed in Example 11 was carried out except that, into the water-absorbable resin powder (2) obtained in Example 2, a surface crosslinking agent solution containing 0.48 parts by weight of 1,4-butanediol, 0.75 parts by weight of propylene glycol, 0.001 parts by weight (10 ppm to the water-absorbable resin powder) of polyoxyethylene (20) sorbitan monostearate (Kao Corporation) and 4.0 parts by weight of deionized water with respect to 100 parts by weight of the water-absorbable resin powder (2) was uniformly sprayed and mixed. In this way, water-absorbable resin powder (12) was obtained, whose properties are listed in Table 3.

The water-absorbable resin powder (12) obtained in Example 12 was water-absorbable resin powder (2) further modified such that particles in which 150 ppm of the surfactant was substantially uniformly contained were coated with 10 ppm of the surfactant on their surface. The water-absorbable resin powder (12) had a surface tension of 67.4 [mN/m].

Comparative Example 10

The comparative water-absorbable resin powder (2) thus obtained in Comparative Example 2 was subjected to process performed in Example 11, thereby obtaining comparative water-absorbable resin powder (10), whose property are listed in Table 3.

Comparative Example 11

The comparative water-absorbable resin powder (9) thus obtained in Comparative Example 9 was subjected to process performed in Example 11, thereby obtaining comparative water-absorbable resin powder (11), whose property are listed in Table 3.

Comparative Example 12

The comparative water-absorbable resin powder (8) thus obtained in Comparative Example 8 was subjected to process performed in Example 11, thereby obtaining comparative water-absorbable resin powder (12), whose property are listed in Table 3.

TABLE 3

Properties after surface crosslinking

|  | CRC [g/g] | FSR [g/g/sec] | SFC*[1] | D50 [μm] | BSG [g/cm$^3$] | AAP [g/g] | ICC [%] |
|---|---|---|---|---|---|---|---|
| Ex. 11 | 27.1 | 0.39 | 134 | 449 | 0.65 | 24.6 | 3.93 |
| Ex. 12 | 27.2 | 0.39 | 145 | 462 | 0.66 | 24.4 | 6.42 |
| CEx. 10 | 26.6 | 0.26 | 150 | 450 | 0.66 | 24.6 | 2.60 |
| CEx. 11 | 26.1 | 0.33 | 92 | 322 | 0.69 | 22.0 |  |
| CEx. 12 | 27.6 | 0.50 | 48 | 411 | 0.55 | 20.1 | 6.83 |

*[1]Unit of SFC: [×10$^{-7}$ · cm$^3$ · sec · g$^{-1}$]
Abbreviations:
Ex. stands for Example.
CEx. stands for Comparative Example.
BSG stands for Bulk Specific Gravity.
ICC stands for Closed-cell rate.

(Summary)

Table 3 shows that the water-absorbable resin powder obtained by the production process according to the present invention can attain both of high water absorbing rate (FSR) and high permeability potential (SFC), which are both dependent on the surface area and have been incompatibles with each other. Moreover, by controlling the closed-cell rate (see later described Example 15 etc. and Table 5 for details) of the water-absorbable resin powder in a range of 2.8% to 6.6%, the water absorbing rate (FSR) and permeability potential (SFC) can be attained at high levels. Moreover, it can be also understood that the user of the multivalent metal cation serving as a permeability improving agent can improve SFC significantly.

Example 13

The water-absorbable resin powder (11) (with closed-cell rate of 3.93%) thus obtained in Example 11 was subjected to the anti-damaging test described in "(5-9) Anti-damaging test", thereby obtaining water-absorbable resin powder (13) having been damaged. Properties of the water-absorbable resin powder (13) before and after the anti-damaging test are listed in Table 4. Note that "PS test" means "Anti-damaging test" in Table 4.

Example 14

The water-absorbable resin powder (12) (with closed-cell rate of 6.42%) thus obtained in Example 12 was subjected to the anti-damaging test described in "(5-9) Anti-damaging test", thereby obtaining water-absorbable resin powder (14) having been damaged. Properties of the water-absorbable resin powder (14) before and after the anti-damaging test are listed in Table 4.

Comparative Example 13

The comparative water-absorbable resin powder (10) (with closed-cell rate of 2.60%) thus obtained in Comparative Example 10 was subjected to the anti-damaging test described in "(5-9) Anti-damaging test", thereby obtaining comparative water-absorbable resin powder (13) having been damaged. Properties of the comparative water-absorbable resin powder (13) before and after the anti-damaging test are listed in Table 4.

Comparative Example 14

The comparative water-absorbable resin powder (12) (with closed-cell rate of 6.83%) thus obtained in Comparative Example 12 was subjected to the anti-damaging test described in "(5-9) Anti-damaging test", thereby obtaining comparative water-absorbable resin powder (14) having been damaged. Properties of the comparative water-absorbable resin powder (14) before and after the anti-damaging test are listed in Table 4.

TABLE 4

Anti-damaging property of surface-crosslinked powder

|  |  | CRC [g/g] | FSR [g/g/sec] | SFC*[1] | D50 [μm] | BSG [g/cm$^3$] | Red. of SFC | Red. of FSR [g/g/sec] |
|---|---|---|---|---|---|---|---|---|
| Ex. 13 | B | 27.1 | 0.39 | 134 | 449 | 0.65 | −8 | −0.01 |
|  | A | 26.9 | 0.38 | 126 | 431 | 0.66 |  |  |
| Ex. 14 | B | 27.2 | 0.39 | 145 | 462 | 0.66 | −3 | 0 |
|  | A | 26.9 | 0.39 | 142 | 460 | 0.67 |  |  |
| CEx. 13 | B | 26.6 | 0.26 | 150 | 450 | 0.66 | −22 | −0.03 |
|  | A | 26.5 | 0.23 | 128 | 423 | 0.67 |  |  |
| CEx. 14 | B | 27.6 | 0.50 | 48 | 411 | 0.55 | −19 | −0.11 |
|  | A | 27.2 | 0.39 | 29 | 372 | 0.60 |  |  |

*[1]Unit of SFC: [×10$^{-7}$ · cm$^3$ · sec · g$^{-1}$]
Abbreviations:
Ex. stands for Example.
CEx. stands for Comparative Example.
B stands for Before PS test.
A stands for After PS test.
BSG stands for Bulk Specific Gravity.
Red. stands for Reduction amount (Summary)

It can be understood from Table 4 that the property deterioration (in SFC and FSR, especially in SFC) in the water-absorbable resin powder according the present invention was small, and therefore the water-absorbable resin powder according the present invention is excellent in anti-damaging property. Moreover, it can be understood that by controlling the closed-cell rate of the water-absorbable resin powder within the range of 2.8% to 6.6%, the water-absorbable resin powder can be excellent in anti-damaging property. The water-absorbable resin powder is not damaged and deteriorated in property during pneumatic transportation or disposable diaper production, thereby being capable of maintaining high property after the diaper production, especially production of high-concentration diaper.

Examples 15 and 16

The water-absorbable resin powder (11) and (12) obtained respectively in Examples 11 and 12 was subjected to the apparent density measurement and the real density measurement described respectively in "(5-10) Apparent density" and "(5-11) Real density", and closed-cell rate described in "(5-12) Closed-cell rate" was calculated out for the water-absorbable resin powder (11) and (12). The results are shown in Table 5.

Comparative Examples 15 and 16

The comparative water-absorbable resin powder (10) and (11) obtained respectively in Comparative Examples 10 and 11 was subjected to the apparent density measurement and the real density measurement described respectively in "(5-10) Apparent density" and "(5-11) Real density", and closed-cell rate described in "(5-12) Closed-cell rate" was calculated out for the comparative water-absorbable resin powder (10) and (11). The results are shown in Table 5.

Comparative Examples 17 and 18

In addition to Non-Patent Literature (1998), commercially-available disposable diapers were purchased in order to find out closed-cell rates of water-absorbable resins commercially available as of filing the present application in 2010. Water-absorbable resin powder used in the disposable diapers were taken out and analyzed.

As comparative water-absorbable resin powder (17) and (18), water-absorbable resins, which were taken out respectively from a disposable diaper purchased in Indonesia in July, 2010 (commercially available under the product name of "Mamy Poko" (Registered Trademark) made by Unicharm Corporation) and from a disposal diaper purchased in Germany in June, 2010 (commercially available under the product name of "babylove aktiv plus" (Registered Trademark) from dm), were subjected to the apparent density measurement and the real density measurement described respectively in "(5-10) Apparent density" and "(5-11) Real density", and closed-cell rate described in "(5-12) Closed-cell rate" was calculated out for the comparative water-absorbable resin powder (17) and (18). The results are shown in Table 5.

TABLE 5

| | Cell rate | | | | |
|---|---|---|---|---|---|
| | Apparent Density [g/cm$^3$] | Real Density [g/cm$^3$] | Closed-cell rate [%] | Ratio of particles with particle diameter in a range of 850 μm to 150 μm [%] | Surface tension [mN/m] |
| Ex. 15 | 1.588 | 1.655 | 4.05 | 99.1 | 68.2 |
| Ex. 16 | 1.546 | 1.652 | 6.42 | 98.5 | |
| CEx. 15 | 1.613 | 1.656 | 2.60 | 99.2 | 71.9 |
| CEx. 16 | 1.542 | 1.655 | 6.83 | 97.9 | |
| CEx. 17 | 1.636 | 1.656 | 1.21 | 97.8 | 63.5 |
| CEx. 18 | 1.645 | 1.655 | 0.60 | 98.5 | |

Abbreviations:
Ex. stands for Example.
CEx. stands for Comparative Example.

(Summary)

It can be understood from Table 5 that, regardless of the measurement samples, fine particles of the water-absorbable resin after dried at 180° C. for three hours or longer and crushed to less than 45 μm had substantially same readings for the real density (1.652 to 1.656). Thus, it can be understood that the real density can be fixedly determined from the chemical composition (repeating unit of the polymer, or the other minute raw materials), and the measurement method adopted herein accurately measured the real density of the water-absorbable resin powder.

As explained above in [3] Properties of water-absorbable polyacrylic acid resin powder, Table 5.6 (p. 197 to 199) in Non-Patent Literature 1 (published in 1998) shows the BET surface area, water absorbing rate, water absorbency, bulk specific gravity, and apparent density of the commercially-available water-absorbable resins (5 kinds) having been subjected to 40 to 60 mesh-cut (corresponding powder sized in a range of 425 μm to 250 μm). However, Non-Patent Literature 1 does not disclose the details of the measurement method, thereby presenting the data incomparable directly with those of the product of the present invention, and does not suggest water-absorbable resin powder, which can satisfy the closed-cell rate or particle diameter of the present invention.

For example, five (5) kinds of commercially-available water-absorbable resins having apparent densities in a range of 1.250 to 1.667 [g/cm$^3$] are disclosed, regarding commercially-available (polyacrylic acid) water-absorbable resins disclosed in Table 5.6 in Non-Patent Literature 1. Assuming that the real densities (chemical compositions) of the water-absorbable resins are equal, the internal cell rates of the water-absorbable resins can be divided into a type having closed-cell rates of 0% or close to 0% (Aquakeep, Dry Tech 510 whose apparent density was 1.667 [g/cm$^3$] after 40-60 mesh-cut) and another type having closed-cell rates approximately in a range of 10% to 25% (Arasorb 720, Sanwet 1M-1000 whose apparent density was 1.500 [g/cm$^3$], and Aridall 1078 whose apparent density was 1.250 [g/cm$^3$]). The five kinds of the commercially-available water-absorbable resins are different from the water-absorbable resin according to the present invention also in terms of the bulk specific gravity and water absorbency.

In addition to the commercially-available water-absorbable resins disclosed in Non-Patent Literature 1 (1998), the closed-cell rates of the commercially-available water-absorbable resin as of filing of the present application (2010) are shown in Comparative Examples 17 and 18. As of 2010, the commercially-available water-absorbable resins (water-absorbable resin taken out of the commercially-available deposable diaper) had the closed-cell rates of 0.60% or 1.21%. This result of the analysis explains that there is no water-absorbable resin on the market, which has the particular closed-cell rate (in a range of 2.8% to 6.6%) in the present invention.

As explained in the summaries for Tables 4 and 5, it can be understood that the water-absorbable resin according to the present invention is a novel polyacrylic acid (salt)-based water-absorbable resin powder having an closed-cell rate in a range of 2.8% to 6.6%, or more preferably in a range of 3.0% to 6.5%, and can solve the conventional problems (difficulty in attaining both the permeability potential and water absorbing rate, and attaining anti-damaging property). Even after receiving process damages in the pneumatic transportation or in the disposable diaper production, such water-absorbable resin can keep high levels of both of the FSR and SFC, which are normally incompatible.

Example 17

The water-absorbable resin powder (11) obtained in Example 11 (closed-cell rate 3.93%) (150 ppm of the surfactant was added in the monomer(s)) was measured in terms of maximum probe insertion load (PIL) and probe insertion distance (PID) described in the above "(5-13) Maximum probe insertion load (PIL) and Probe insertion distance (PID)". Results of the measurement are shown in Table 6.

Example 18

The water-absorbable resin powder (2) obtained in Example 2 was subjected to surface crosslinking treatment as in Example 12 (using 10 ppm of the surfactant), thereby obtaining water-absorbable resin powder (18).

Like the water-absorbable resin powder (12) obtained in Example 12, the water-absorbable resin powder (18) was water-absorbable resin powder (2) further modified such that particles in which 150 ppm of the surfactant was substantially uniformly contained were coated with 10 ppm of the surfactant on their surface. The water-absorbable resin powder (18) has a surface tension of 67.4 [mN/m].

As in Example 17, the water-absorbable resin powder (18) was measured in terms of maximum probe insertion load (PIL) and probe insertion distance (PID). Results of the measurement are shown in Table 6.

Comparative 19

The comparative water-absorbable resin powder (10) obtained in Comparative Example 10 (closed-cell rate 2.60%) (without using the surfactant) measured in terms of maximum probe insertion load (PIL) and probe insertion distance (PID). Results of the measurement are shown in Table 6.

Comparative Example 20

The comparative water-absorbable resin powder (2) obtained in Comparative Example 2 was subjected to surface crosslinking treatment as in Example 12, thereby obtaining comparative water-absorbable resin powder (20). The comparative water-absorbable resin powder (20) contained no surfactant inside their particles (core portion) but was coated with 10 ppm of the surfactant on the surface of the particles. The comparative water-absorbable resin powder (20) was measured in terms of maximum probe insertion load (PIL) and probe insertion distance (PID). Results of the measurement are shown in Table 6.

TABLE 6

| | Probe insertion work | |
| --- | --- | --- |
| | PID [mm] | PIL [g weight] |
| Example 17 | 13.4 | >10000 |
| Example 18 | 16.3 | >10000 |
| Comparative Example 19 | 10.8 | >10000 |
| Comparative Example 20 | 12.8 | >10000 |

(Summary)

It can be understood from Table 6 that the probe insertion distance (PID) becomes dramatically larger in the water-absorbable resin particles containing the surfactant uniformly inside thereof and being coated with the surfactant on the surface thereof (Example 18) than those containing no surfactant or those having the surfactant only inside or on the surface thereof. The arrangement in which the water-absorbable resin particles containing the surfactant uniformly inside thereof and being coated with the surfactant on the surface thereof makes it possible to reduce the amount of the surfactant necessary to attain the same effect. Thus, this arrangement makes it possible to obtain the water-absorbable resin high in slidability and excellent in handling property and anti-damaging property substantially without surface tension reduction.

Hereinafter, the effect of p-methoxy phenol in attaining the object (especially, coloring, and anti-damaging property) of the present invention is demonstrated in Examples 19 to 22.

Example 19

The water-absorbable resin powder (1) obtained in Example 1 was measured in terms of p-methoxy phenol content. The p-methoxy phenol content was 12 ppm.

Example 20

Water-absorbable resin powder (20) was prepared in the same way as in Example 1 except that the polymerization was carried out with the p-methoxy phenol amount of 1 ppm. The resultant water-absorbable resin powder (20) was measured in terms of p-methoxy phenol content, but only to find that the p-methoxy phenol content was ND (less than 1 ppm). The water-absorbable resin powder (20) with such non-detectable p-methoxy phenol content (less than 1 ppm) showed anti-weatherability (light deterioration; described in (5-15) above) worse by about 10% than the water-absorbable resin powder (1) with p-methoxy phenol content of 12 ppm. This explains that the p-methoxy phenol improves the antiweatherability of the water-absorbable resin. As described above, the p-methoxy phenol content in the monomer(s) and/or the water-absorbable resin plays an important role in antiweatherability (anti-damaging property against light).

Example 21

Water-absorbable resin powder (21) was prepared in the same way as in Example 1 except that the polymerization was carried out with p-methoxy phenol content of 230 ppm. The resultant water-absorbable resin powder (21) was measured in p-methoxy phenol content. The p-methoxy phenol content was 82 ppm. The water-absorbable resin powder (21) showed initial coloring (coloring right after the production) worse than the water-absorbable resin powder (1) with p-methoxy phenol content of 12 ppm. The initial coloring of the water-absorbable resin powder (21) was such that L value was 88.3, a value was −1.8, and b value was 10.2. From this, it can be understood that the p-methoxy phenol content in the monomer(s) and/or the water-absorbable resin plays an important role in coloring.

Example 22

Water-absorbable resin powder (22) having the same property as that in Example 11 was prepared in the same way as in Example 2 except that the polymerization was carried out with p-methoxy phenol content of 70 ppm, and the surface crosslinking treatment as in Example 11 was carried out. The resultant water-absorbable resin powder (22) was measured in p-methoxy phenol content. The p-methoxy phenol content was 10 ppm.

In the following, Examples 23 to 25 demonstrates embodiments in which post-polymerization gel grinding according to Japanese Patent Application, Tokugan, No. 2010-088993 was additionally carried out.

Example 23

Figure 14:
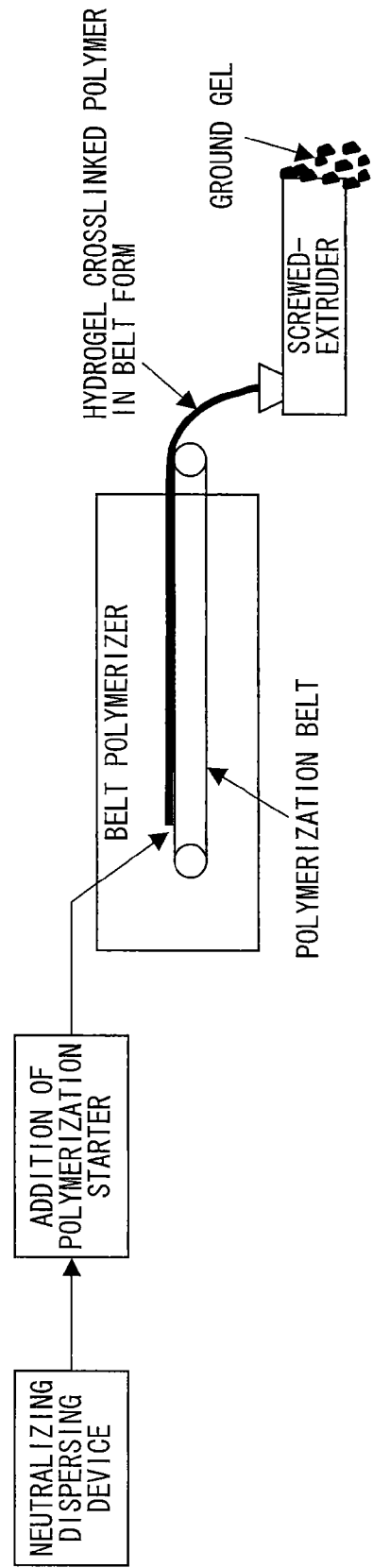
FIG. 14 is a cross sectional view schematically illustrating a step of preparing ground gel by introducing a hydrogel crosslinked polymer into a screwed extruder by using a belt polymerizer, as one preferable embodiment of the present invention, which can be applied to the first method and the second method of the present invention.
Figure 15:
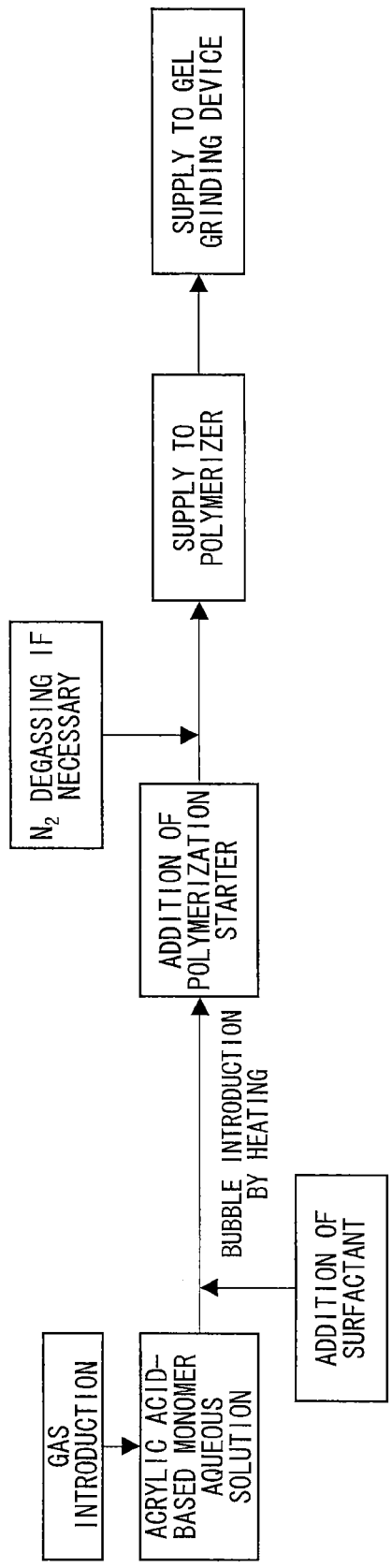
FIG. 15 is a flow diagram schematically illustrating one embodiment in which a thermal bubbling method for the acrylic acid-based monomer aqueous solution is arranged to include introducing a gas (especially micro bubbles) if necessary, and further include performing pre-polymerization deoxidation of the monomer aqueous solution by inert gas (for example, nitrogen) before the polymerization, and performing gel pulverization of the resultant hydrogel crosslinked polymer, as one preferable embodiment of the present invention, which can be applied to the first method and the second method of the present invention.

By using a dispersing device, 595.4 [g/min] of 37 wt % sodium acrylic acid aqueous solution, 198.6 [g/min] of 48 wt % sodium hydroxide aqueous solution, 300.1 [g/min] of 100 wt % acrylic acid, 2.71 [g/min] of polyethylene glycol diacrylate (molecular weight 523) as an internal crosslinking agent, 203.9 [g/min] of deionized water (ion exchanged water), 0.42 [g/min] of 31 wt % diethylene triamin pentaacetate trisodium aqueous solution, and 0.46 [g/min] of 10 wt % polyoxy ethylene [20] sorbitan monostearate (Kao Corporation) aqueous solution as a surfactant were continuously mixed, thereby obtaining a monomer aqueous solution having passed through the dispersing device. Into the monomer aqueous solution, 26.0 [g/min] of 3 wt % sodium persulfate aqueous solution was mixed in by line mixing. Then, the monomer aqueous solution was supplied to a belt polymerizer. The belt polymerizer was configured to include an endless belt of 3.8 m in length and 60 cm in width with a surface coated with fluorine resin coating. A bottom surface of the belt and an environment of the polymerizer were heated and kept at about 90° C. In a center portion thereof, the belt polymerizer had an inhalation piping for collecting steam. Moreover, temperature of the monomer aqueous solution to be supplied onto the belt was controlled to 92° C. by passing water through the dispersing device (see FIG. 14).

The temperature of the monomer aqueous solution (23) was 92° C. supplied to the polymerizer and a dissolved oxygen content of 4.30 [ml/l].

Here, the surfactant-containing monomer aqueous solution (23) was whitely turbid due to very fine bubbles introduced therein because the solubility of the gas was lowered. Right after the surfactant-containing monomer aqueous solution (23) being continuously supplied was supplied to the belt polymerizer, the polymerization started. The surfactant-containing monomer aqueous solution (23) was polymerized for 2 minutes in the polymerizing device, and then continuously discharged out of an outlet of the polymerizer, thereby hydrogel polymer (hydrogel) in the form of a belt. The resultant gel had a water soluble content of 3.2 wt % and a solid content of 53 wt %. The water soluble content had a weight average molecular weight of 228521 [Da].

Next, after cutting the hydrogen gel in a length of 200 mm, the resultant hydrogen gel was treated with the following screwed extruder (meat chopper), thereby performing gel grinding. The screwed extruder had a porous die at its end. The die had a diameter of 100 mm, and a pore diameter of 7.5 mm. The number of pores in the die was 55 and the die was 6 mm in thickness. The gel grinding was carried out with a hydrogel supplying rate of 1600 [g/min]. Further, hot water of 90° C. (at a supplying rate of 50 [g/min]) and steam (at a supplying rate of 70 [g/min]) were concurrently supplied to the meat chopper. A screw rotation speed of the meat chopper was 412 rpm. The hydrogel before the gel grinding had a temperature of 94° C. The hydrogel after the gel crushing (hereinafter, referred to as "ground hydrogel") had a temperature of 103° C.

The resultant ground gel (23) had a weight average particle diameter (D50) of 897 μm, a logarithmic standard deviation (σξ) of particle size distribution of 0.98. Further, the resultant ground gel (23) had a water soluble content of 3.8 wt % and a solid content of 49.4 wt %. A weight average molecular weight of the water soluble content was 263330 [Da].

Next, the resultant ground gel (23) was subjected to the crushing, drying, grinding, and classifying as in Example 1.

In this way, prepared was water-absorbable resin powder (23) with solid content of 96 wt %, weight average particle diameter (D50) of 445 μm, logarithmic standard deviation (σξ) of particle diameter distribution of 0.36, and irregular broken shapes. Properties of the water-absorbable resin powder (23) are listed in Table 7. Note that the water soluble content and the weight average molecular weight of the water soluble content were measured according to Japanese Patent Application, Tokugan, No. 2010-088993.

Example 24

Ground gel (24) was prepared in the same way as in Example 23 except that the gel grinding was carried out with a meat chopper provided with a 10.5 mm-thick die having 10 pores of 19.0 mm in pore diameter, wherein the supplying rate of the hydrogen gel was 1600 [g/min], hot water of 90° C. (at a supplying rate of 63 [g/min]) and steam (at a supplying rate of 95 [g/min]) were concurrently supplied to the meat chopper, and the screw rotation speed was 257 rpm.

The resultant ground gel (24) had a weight average particle diameter (D50) of 1232 μm, a logarithmic standard deviation (σξ) of particle size distribution of 1.88. Further, the resultant ground gel (24) had a water soluble content 3.8 wt % and a solid content of 51.1 wt %. A weight average molecular weight of the water soluble content was 229121 [Da].

Next, the resultant ground gel (24) was subjected to the crushing, drying, grinding, and classifying as in Example 1.

In this way, prepared was water-absorbable resin powder (24) with solid content of 95 wt %, weight average particle diameter (D50) of 433 μm, logarithmic standard deviation (σξ) of particle diameter distribution of 0.39, and irregular broken shapes. Properties of the water-absorbable resin powder (24) are listed in Table 7.

Example 25

Gel was prepared in the same way as in Example 23 except that, by using a micro bubble generating device (Aura Tech, Product code: OM4-GP-040), introduced gas (nitrogen gas) was introduced into 37 wt % sodium acrylic acid aqueous solution and the deionized water (ion exchanged water) used as the monomer aqueous solution. The gel thus obtained had a water soluble content 3.0 wt % and a solid content of 53 wt %. A weight average molecular weight of the water soluble content was 236521 [Da].

The gel was crushed in the same way as in Example 23. The resultant ground gel (25) had a weight average particle diameter (D50) of 879 μm, a logarithmic standard deviation (σξ) of particle size distribution of 0.97. Further, the resultant ground gel (25) had a water soluble content 3.6 wt % and a solid content of 48.8 wt %. A weight average molecular weight of the water soluble content was 269981 [Da].

Next, the resultant ground gel (25) was subjected to the crushing, drying, grinding, and classifying as in Example 1.

In this way, prepared was water-absorbable resin powder (25) with solid content of 95 wt %, weight average particle diameter (D50) of 446 μm, logarithmic standard deviation (σξ) of particle diameter distribution of 0.35, and irregular broken shapes. Properties of the water-absorbable resin powder (25) are listed in Table 7.

TABLE 7

Increases in water soluble content and weight average molecular weight of water soluble content

| | Hydrogel in belt form | | Crushed Hydrogel | | |
|---|---|---|---|---|---|
| | WSC [wt %] | WAMW of WSC [Da] | WSC [wt %] | WAMW of WSC [Da] | D50 [μm] |
| Example 23 | 3.2 | 228,521 | 3.8 | 263,330 | 897 |
| Example 24 | 3.2 | 228,521 | 3.8 | 229,121 | 1232 |
| Example 25 | 3.0 | 236,555 | 3.8 | 269,981 | 879 |

| | Water-Absorbable Resin Powder | | | | |
|---|---|---|---|---|---|
| | CRC [g/g] | FSR [g/g/sec] | BSG [g/cm$^3$] | D50 [μm] | SC [wt %] |
| Example 23 | 34.0 | 0.38 | 0.62 | 445 | 96 |
| Example 24 | 33.7 | 0.35 | 0.64 | 433 | 95 |
| Example 25 | 34.1 | 0.40 | 0.60 | 446 | 95 |

Abbreviations:
WSC stands for Water Soluble Content.
WAMW stands for Weight Average Molecular Weight.
BSG stands for Bulk Specific Gravity.
SC stands for Solid Content.

INDUSTRIAL APPLICABILITY

The use of water-absorbable resin powder according to the present invention in sanitary products such as disposable diapers etc. makes it possible to attain both the permeability potential and water absorbing rate and provide excellent impact resistance (anti-damaging property) and the degree of whiteness. Thus, the present invention can provide sanitary products more excellent in absorbing performance (water absorbing rate) than conventional sanitary products.

The invention claimed is:

1. Water-absorbable resin powder being water-absorbable polyacrylic acid resin powder in which particles having a particle diameter of 850 μm to 150 μm accounts for 95 wt % or more, and having an internal cell rate of 2.8% to 6.6%, the internal cell rate being defined by the following equation:

(internal cell rate [%]={(Real Density [g/cm$^3$])−(Apparent Density [g/cm$^3$])}/(Real Density [g/cm$^3$])×100, the water-absorbable resin powder having a degree of whiteness of 68 or more [WB value] as measured with use of a spectral colorimeter.

2. The water-absorbable resin powder as set forth in claim 1, containing a surfactant and/or a dispersing agent inside thereof, wherein:
the water-absorbable resin powder has a surface tension of 60 [mN/m] or greater, and a particle surface being coated with a/the surfactant.

3. The water-absorbable resin powder as set forth in claim 1, wherein a saline flow conductivity thereof is 20 [×10$^{-7}$·cm$^3$·sec·g$^{-1}$] or greater, and a water absorbing rate (FSR) thereof is 0.25 [g/g/sec] or greater.

4. The water-absorbable resin powder as set forth in claim 1, wherein an absorbency without pressure (CRC) thereof is 25 [g/g] or more, and an absorbency against pressure (AAP) under load of 50 [g/cm$^2$] thereof is 15 [g/g] or more.

5. The water-absorbable resin powder as set forth in claim 1, wherein an absorbency without pressure (CRC) thereof is 25 [g/g] or more, and a saline flow conductivity thereof is 20 [×10$^{-7}$·cm$^3$·sec·g$^{-1}$] or greater.

6. The water-absorbable resin powder as set forth in claim 1, further comprising:
one or more kinds of permeability improving agents selected from the group consisting of multivalent metal cations, polyamine polymers and water insoluble fine particles.

7. The water-absorbable resin powder as set forth in claim 1, further comprising a surfactant.

8. The water-absorbable resin powder as set forth in claim 1, further comprising p-methoxy phenol by 5 ppm to 60 ppm.

9. The water-absorbable resin powder as set forth in claim 1, further comprising one or more kinds of additives selected from the group consisting of chelating agents, α-hydroxy carboxylic acids, and inorganic or organic reducing agents.

10. The water-absorbable resin powder as set forth in claim 1, wherein
a water absorbing rate index there of is 90 or more, water absorbing rate index being defined by the following equation:

(Water Absorbing Rate Index)=(FSR [g/g/sec])×(Bulk Specific Gravity [g/cm$^3$])×(Weight Average Particle Diameter [μm]), where FSR is a water absorbing rate for saline so as to swell 20-fold, and
a bulk specific gravity thereof is in a range of 0.6 to 0.8 [g/cm$^3$].

11. The water-absorbable resin powder as set forth in claim 1, wherein a surface tension thereof is 60 [mN/m] or greater.

12. The water-absorbable resin powder as set forth in claim 1, wherein a bulk specific gravity thereof is in a range of 0.58 to 0.80 [g/cm$^3$].

* * * * *